United States Patent
Albrecht et al.

(10) Patent No.: US 8,262,568 B2
(45) Date of Patent: Sep. 11, 2012

(54) SINGLE PORT ACCESS SYSTEM

(75) Inventors: Jeremy J. Albrecht, Rancho Santa Margarita, CA (US); Matthew M. Becerra, Foothill Ranch, CA (US); John R. Brustad, Dana Point, CA (US); Juan Lechuga, Santa Ana, CA (US); Donald L. Gadberry, Capistrano Beach, CA (US); Gary M. Johnson, Mission Viejo, CA (US); Aries E. Gatus, Mission Viejo, CA (US); Kennii Pravongviengkham, Garden Grove, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 388 days.

(21) Appl. No.: 12/578,422

(22) Filed: Oct. 13, 2009

(65) Prior Publication Data
US 2010/0094227 A1 Apr. 15, 2010

Related U.S. Application Data

(60) Provisional application No. 61/104,963, filed on Oct. 13, 2008.

(51) Int. Cl.
*A61B 1/32* (2006.01)
(52) U.S. Cl. ..................................... 600/206
(58) Field of Classification Search .......... 604/264, 604/178; 600/206
See application file for complete search history.

(56) References Cited

U.S. PATENT DOCUMENTS

| | | | |
|---|---|---|---|
| 558,364 A | 4/1896 | Doolittle |
| 1,157,202 A | 10/1915 | Bates et al. |
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |

(Continued)

FOREIGN PATENT DOCUMENTS

DE 26 05 148 A1 8/1977

(Continued)

OTHER PUBLICATIONS

U.S. Appl. No. 10/381,220, filed Mar. 20, 2003; Title: Surgical Access Apparatus and Method, now USPN 7,473,221 issued Jan. 6, 2009.

(Continued)

*Primary Examiner* — Kevin T Truong
*Assistant Examiner* — Sameh Boles
(74) *Attorney, Agent, or Firm* — Patrick Y. Ikehara; Pui Tong Ho

(57) ABSTRACT

Embodiments of a surgical access system useful for single or limited port procedures comprise a trocar comprising a fixation cannula, a retractor, and a gel cap removably coupled to the retractor. The gel cap comprises a gel pad that acts as an artificial body wall, through which instruments may be inserted into a body cavity, either directly or through one or more trocars. The fixation cannula comprises a retainer and a bolster, which together, capture the artificial body wall therebetween, thereby fixing the trocar thereto. The gel pad permits flexible instrument placement, as well as translational and angular degrees of freedom for the instruments while maintaining a gas tight seal.

23 Claims, 26 Drawing Sheets

U.S. PATENT DOCUMENTS

| | | |
|---|---|---|
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Benjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |

| Patent No. | Date | Inventor |
|---|---|---|
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,201,714 A | 4/1993 | Gentelia et al. |
| 5,207,656 A | 5/1993 | Kranys |
| 5,209,737 A | 5/1993 | Ritchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Blake, III et al. |
| 5,242,409 A | 9/1993 | Buelna |
| 5,242,412 A | 9/1993 | Blake, III |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Dubrul et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |

| | | | | | |
|---|---|---|---|---|---|
| 5,651,771 A | 7/1997 | Tangherlini et al. | 5,951,588 A | 9/1999 | Moenning |
| 5,653,705 A | 8/1997 | de la Torre et al. | 5,957,888 A | 9/1999 | Hinchliffe et al. |
| 5,657,963 A | 8/1997 | Hinchliffe et al. | 5,957,913 A | 9/1999 | de la Torre et al. |
| 5,658,272 A | 8/1997 | Hasson | 5,962,572 A | 10/1999 | Chen |
| 5,658,306 A | 8/1997 | Kieturakis | 5,964,781 A | 10/1999 | Mollenauer et al. |
| 5,662,615 A | 9/1997 | Blake, III | 5,976,174 A | 11/1999 | Ruiz |
| 5,672,168 A | 9/1997 | de la Torre et al. | 5,989,232 A | 11/1999 | Yoon |
| 5,681,341 A | 10/1997 | Lunsford et al. | 5,989,233 A | 11/1999 | Yoon |
| 5,683,378 A | 11/1997 | Christy | 5,989,266 A | 11/1999 | Foster |
| 5,685,854 A | 11/1997 | Green et al. | 5,993,471 A | 11/1999 | Riza et al. |
| 5,685,857 A | 11/1997 | Negus et al. | 5,993,485 A | 11/1999 | Beckers |
| 5,697,914 A | 12/1997 | Brimhall | 5,994,450 A | 11/1999 | Pearce |
| 5,707,703 A | 1/1998 | Rothrum et al. | 5,997,515 A | 12/1999 | de la Torre et al. |
| 5,709,664 A | 1/1998 | Vandenbroek et al. | 6,004,303 A | 12/1999 | Peterson |
| 5,713,858 A | 2/1998 | Heruth et al. | 6,010,494 A | 1/2000 | Schafer et al. |
| 5,713,869 A | 2/1998 | Morejon | 6,017,355 A | 1/2000 | Hessel et al. |
| 5,720,730 A | 2/1998 | Blake, III | 6,018,094 A | 1/2000 | Fox |
| 5,725,536 A | 3/1998 | Oberlin et al. | 6,024,736 A | 2/2000 | de la Torre et al. |
| 5,728,103 A | 3/1998 | Picha et al. | 6,025,067 A | 2/2000 | Fay |
| 5,730,748 A | 3/1998 | Fogarty et al. | 6,033,426 A | 3/2000 | Kaji |
| 5,735,791 A | 4/1998 | Alexander et al. | 6,033,428 A | 3/2000 | Sardella |
| 5,738,628 A | 4/1998 | Sierocuk et al. | 6,035,559 A | 3/2000 | Freed et al. |
| 5,741,234 A | 4/1998 | Aboul-Hosn | 6,042,573 A | 3/2000 | Lucey |
| 5,741,298 A | 4/1998 | MacLeod | 6,045,535 A | 4/2000 | Ben Nun |
| 5,743,884 A | 4/1998 | Hasson et al. | 6,048,309 A | 4/2000 | Flom et al. |
| 5,749,882 A | 5/1998 | Hart et al. | 6,050,871 A | 4/2000 | Chen |
| 5,755,660 A | 5/1998 | Tyagi | 6,053,934 A | 4/2000 | Andrews et al. |
| 5,760,117 A | 6/1998 | Chen | 6,059,816 A | 5/2000 | Moenning |
| 5,769,783 A | 6/1998 | Fowler | 6,066,117 A | 5/2000 | Fox et al. |
| 5,782,812 A | 7/1998 | Hart et al. | 6,068,639 A | 5/2000 | Fogarty et al. |
| 5,782,817 A | 7/1998 | Franzel et al. | 6,077,288 A | 6/2000 | Shimomura et al. |
| 5,782,859 A | 7/1998 | Nicholas et al. | 6,086,603 A | 7/2000 | Termin et al. |
| 5,788,676 A | 8/1998 | Yoon | 6,090,043 A | 7/2000 | Austin et al. |
| 5,792,119 A | 8/1998 | Marx | 6,099,506 A | 8/2000 | Macoviak et al. |
| 5,795,290 A | 8/1998 | Bridges | 6,110,154 A | 8/2000 | Shimomura et al. |
| 5,803,919 A | 9/1998 | Hart et al. | 6,123,689 A | 9/2000 | To |
| 5,803,921 A | 9/1998 | Bonadio | 6,142,935 A | 11/2000 | Flom et al. |
| 5,803,923 A | 9/1998 | Singh-Derewa et al. | 6,142,936 A | 11/2000 | Beane et al. |
| 5,807,350 A | 9/1998 | Diaz | 6,149,642 A | 11/2000 | Gerhart et al. |
| 5,810,712 A | 9/1998 | Dunn | 6,150,608 A | 11/2000 | Wambeke et al. |
| 5,810,721 A | 9/1998 | Mueller et al. | 6,159,182 A | 12/2000 | Davis |
| 5,813,409 A | 9/1998 | Leahy et al. | 6,162,172 A | 12/2000 | Cosgrove et al. |
| 5,814,026 A | 9/1998 | Yoon | 6,162,196 A | 12/2000 | Hart et al. |
| 5,817,062 A | 10/1998 | Flom et al. | 6,162,206 A | 12/2000 | Bindokas |
| 5,819,375 A | 10/1998 | Kastner | 6,163,949 A | 12/2000 | Neuenschwander |
| 5,820,555 A | 10/1998 | Watkins, III et al. | 6,164,279 A | 12/2000 | Tweedle |
| 5,820,600 A | 10/1998 | Carlson et al. | 6,171,282 B1 | 1/2001 | Ragsdale |
| 5,830,191 A | 11/1998 | Hildwein et al. | 6,183,486 B1 | 2/2001 | Snow et al. |
| 5,832,925 A | 11/1998 | Rothrum | 6,197,002 B1 | 3/2001 | Peterson |
| 5,836,871 A | 11/1998 | Wallace et al. | 6,217,555 B1 | 4/2001 | Hart et al. |
| 5,841,298 A | 11/1998 | Huang | 6,217,590 B1 | 4/2001 | Levinson |
| 5,842,971 A | 12/1998 | Yoon | 6,224,612 B1 | 5/2001 | Bates et al. |
| 5,848,992 A | 12/1998 | Hart et al. | 6,228,063 B1 | 5/2001 | Aboul-Hosn |
| 5,853,395 A | 12/1998 | Crook et al. | 6,238,373 B1 | 5/2001 | de la Torre et al. |
| 5,853,417 A | 12/1998 | Fogarty et al. | 6,241,768 B1 | 6/2001 | Agarwal et al. |
| 5,857,461 A | 1/1999 | Levitsky et al. | 6,254,533 B1 | 7/2001 | Fadem et al. |
| 5,860,995 A | 1/1999 | Berkelaar | 6,254,534 B1 | 7/2001 | Butler et al. |
| 5,865,728 A | 2/1999 | Moll et al. | 6,258,065 B1 | 7/2001 | Dennis et al. |
| 5,865,729 A | 2/1999 | Meehan et al. | 6,264,604 B1 | 7/2001 | Kieturakis et al. |
| 5,865,807 A | 2/1999 | Blake, III | 6,267,751 B1 | 7/2001 | Mangosong |
| 5,865,817 A | 2/1999 | Moenning et al. | 6,276,661 B1 | 8/2001 | Laird |
| 5,871,474 A | 2/1999 | Hermann et al. | 6,287,280 B1 | 9/2001 | Lampropoulos et al. |
| 5,876,413 A | 3/1999 | Fogarty et al. | 6,315,770 B1 | 11/2001 | de la Torre et al. |
| 5,879,368 A | 3/1999 | Hoskin et al. | 6,319,246 B1 | 11/2001 | de la Torre et al. |
| 5,882,344 A | 3/1999 | Stouder, Jr. | 6,322,541 B2 | 11/2001 | West |
| 5,884,639 A | 3/1999 | Chen | 6,325,384 B1 | 12/2001 | Berry, Sr. et al. |
| 5,894,843 A | 4/1999 | Benetti et al. | 6,346,074 B1 | 2/2002 | Roth |
| 5,895,377 A | 4/1999 | Smith et al. | 6,371,968 B1 | 4/2002 | Kogasaka et al. |
| 5,899,208 A | 5/1999 | Bonadio | 6,382,211 B1 | 5/2002 | Crook |
| 5,899,913 A | 5/1999 | Fogarty et al. | 6,383,162 B1 | 5/2002 | Sugarbaker |
| 5,904,703 A | 5/1999 | Gilson | 6,391,043 B1 | 5/2002 | Moll et al. |
| 5,906,577 A | 5/1999 | Beane et al. | 6,413,244 B1 | 7/2002 | Bestetti et al. |
| 5,913,847 A | 6/1999 | Yoon | 6,413,458 B1 | 7/2002 | Pearce |
| 5,916,198 A | 6/1999 | Dillow | 6,420,475 B1 | 7/2002 | Chen |
| 5,916,232 A | 6/1999 | Hart | 6,423,036 B1 | 7/2002 | Van Huizen |
| 5,919,476 A | 7/1999 | Fischer et al. | 6,440,061 B1 | 8/2002 | Wenner et al. |
| 5,931,832 A | 8/1999 | Jensen | 6,440,063 B1 | 8/2002 | Beane et al. |
| 5,947,922 A | 9/1999 | MacLeod | 6,443,957 B1 | 9/2002 | Addis |
| 5,951,467 A | 9/1999 | Picha et al. | 6,447,489 B1 | 9/2002 | Peterson |

| | | |
|---|---|---|
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Pasqualucci et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Lui et al. |
| 7,105,009 B2 | 9/2006 | Johnson |
| 7,105,607 B2 | 9/2006 | Chen |
| 7,108,009 B2 | 9/2006 | Ishida |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,850,667 B2 | 12/2010 | Gresham |
| 7,867,164 B2 | 1/2011 | Butler et al. |
| 7,878,974 B2 | 2/2011 | Brustad et al. |
| 7,896,889 B2 | 3/2011 | Mazzocchi et al. |
| 7,909,760 B2 | 3/2011 | Albrecht et al. |
| 7,930,782 B2 | 4/2011 | Chen |
| 2001/0037053 A1 | 11/2001 | Bonadio et al. |
| 2001/0047188 A1 | 11/2001 | Bonadio et al. |
| 2002/0002324 A1 | 1/2002 | McManus |

| | | | | | | |
|---|---|---|---|---|---|---|
| 2002/0010389 A1 | 1/2002 | Butler et al. | 2006/0047284 A1 | 3/2006 | Gresham | |
| 2002/0013542 A1 | 1/2002 | Bonadio et al. | 2006/0047293 A1 | 3/2006 | Haberland et al. | |
| 2002/0016607 A1 | 2/2002 | Bonadio et al. | 2006/0052669 A1 | 3/2006 | Hart | |
| 2002/0026230 A1 | 2/2002 | Moll et al. | 2006/0084842 A1 | 4/2006 | Hart et al. | |
| 2002/0038077 A1 | 3/2002 | de la Torre et al. | 2006/0106402 A1 | 5/2006 | McLucas | |
| 2002/0072762 A1 | 6/2002 | Bonadio et al. | 2006/0129165 A1 | 6/2006 | Edoga et al. | |
| 2002/0111536 A1 | 8/2002 | Cuschieri et al. | 2006/0149137 A1 | 7/2006 | Pingleton et al. | |
| 2003/0004253 A1 | 1/2003 | Chen | 2006/0149306 A1 | 7/2006 | Hart et al. | |
| 2003/0028179 A1 | 2/2003 | Piskun | 2006/0161049 A1 | 7/2006 | Beane et al. | |
| 2003/0040711 A1 | 2/2003 | Racenet et al. | 2006/0161050 A1 | 7/2006 | Butler et al. | |
| 2003/0078478 A1 | 4/2003 | Bonadio et al. | 2006/0241651 A1 | 10/2006 | Wilk | |
| 2003/0139756 A1 | 7/2003 | Brustad | 2006/0247498 A1 | 11/2006 | Bonadio et al. | |
| 2003/0167040 A1 | 9/2003 | Bacher et al. | 2006/0247499 A1 | 11/2006 | Butler et al. | |
| 2003/0187376 A1 | 10/2003 | Rambo | 2006/0247500 A1 | 11/2006 | Voegele et al. | |
| 2003/0192553 A1 | 10/2003 | Rambo | 2006/0247516 A1 | 11/2006 | Hess et al. | |
| 2003/0225392 A1 | 12/2003 | McMichael et al. | 2006/0247586 A1 | 11/2006 | Voegele et al. | |
| 2003/0236505 A1 | 12/2003 | Bonadio et al. | 2006/0247673 A1 | 11/2006 | Voegele et al. | |
| 2003/0236549 A1 | 12/2003 | Bonadio et al. | 2006/0247678 A1 | 11/2006 | Weisenburgh, II et al. | |
| 2004/0015185 A1 | 1/2004 | Ewers et al. | 2006/0258899 A1 | 11/2006 | Gill et al. | |
| 2004/0024363 A1 | 2/2004 | Goldberg | 2006/0264706 A1 | 11/2006 | Piskun | |
| 2004/0049099 A1 | 3/2004 | Ewers et al. | 2006/0270911 A1 | 11/2006 | Voegele et al. | |
| 2004/0049100 A1 | 3/2004 | Butler | 2007/0004968 A1 | 1/2007 | Bonadio et al. | |
| 2004/0054353 A1 | 3/2004 | Taylor | 2007/0049966 A1 | 3/2007 | Bonadio et al. | |
| 2004/0063833 A1 | 4/2004 | Chen | 2007/0093695 A1 | 4/2007 | Bonadio et al. | |
| 2004/0068232 A1 | 4/2004 | Hart et al. | 2007/0097793 A1 | 5/2007 | Nguy et al. | |
| 2004/0070187 A1 | 4/2004 | Chen | 2007/0118175 A1 | 5/2007 | Butler et al. | |
| 2004/0072942 A1 | 4/2004 | Chen | 2007/0151566 A1 | 7/2007 | Kahle et al. | |
| 2004/0073090 A1 | 4/2004 | Butler | 2007/0156023 A1 | 7/2007 | Frasier et al. | |
| 2004/0092795 A1 | 5/2004 | Bonadio et al. | 2007/0203398 A1 | 8/2007 | Bonadio et al. | |
| 2004/0092796 A1 | 5/2004 | Butler et al. | 2007/0208312 A1 | 9/2007 | Norton et al. | |
| 2004/0093018 A1 | 5/2004 | Johnson | 2007/0239108 A1* | 10/2007 | Albrecht et al. | 604/96.01 |
| 2004/0097793 A1 | 5/2004 | Butler et al. | 2007/0255219 A1 | 11/2007 | Vaugh et al. | |
| 2004/0106942 A1 | 6/2004 | Taylor | 2007/0299387 A1 | 12/2007 | Williams et al. | |
| 2004/0111061 A1 | 6/2004 | Curran | 2008/0027476 A1 | 1/2008 | Piskun | |
| 2004/0127772 A1 | 7/2004 | Ewers et al. | 2008/0048011 A1 | 2/2008 | Weller | |
| 2004/0138529 A1 | 7/2004 | Wiltshire et al. | 2008/0097162 A1 | 4/2008 | Bonadio et al. | |
| 2004/0143158 A1 | 7/2004 | Hart et al. | 2008/0097163 A1 | 4/2008 | Butler et al. | |
| 2004/0154624 A1 | 8/2004 | Bonadio et al. | 2008/0200767 A1 | 8/2008 | Ewers et al. | |
| 2004/0167559 A1 | 8/2004 | Taylor et al. | 2008/0255519 A1 | 10/2008 | Piskun et al. | |
| 2004/0173218 A1 | 9/2004 | Yamada et al. | 2008/0281161 A1 | 11/2008 | Albrecht et al. | |
| 2004/0215063 A1 | 10/2004 | Bonadio et al. | 2008/0281162 A1 | 11/2008 | Albrecht et al. | |
| 2004/0230161 A1 | 11/2004 | Zeiner | 2009/0012477 A1 | 1/2009 | Norton et al. | |
| 2004/0243144 A1 | 12/2004 | Bonadio et al. | 2009/0036745 A1 | 2/2009 | Bonadio et al. | |
| 2004/0249248 A1 | 12/2004 | Bonadio et al. | 2009/0069837 A1 | 3/2009 | Bonadio et al. | |
| 2004/0254426 A1 | 12/2004 | Wenchell | 2009/0093683 A1 | 4/2009 | Richard et al. | |
| 2004/0260244 A1 | 12/2004 | Piechowicz et al. | 2009/0093752 A1 | 4/2009 | Richard et al. | |
| 2004/0267096 A1 | 12/2004 | Caldwell et al. | 2009/0131754 A1 | 5/2009 | Ewers et al. | |
| 2005/0020884 A1 | 1/2005 | Hart et al. | 2009/0137879 A1 | 5/2009 | Ewers et al. | |
| 2005/0033246 A1 | 2/2005 | Ahlberg et al. | 2009/0149714 A1 | 6/2009 | Bonadio | |
| 2005/0059865 A1 | 3/2005 | Kahle et al. | 2009/0182279 A1 | 7/2009 | Wenchell et al. | |
| 2005/0065475 A1 | 3/2005 | Hart et al. | 2009/0187079 A1 | 7/2009 | Albrecht et al. | |
| 2005/0065543 A1 | 3/2005 | Kahle et al. | 2009/0227843 A1 | 9/2009 | Smith et al. | |
| 2005/0090713 A1 | 4/2005 | Gonzales et al. | 2009/0292176 A1 | 11/2009 | Bonadio et al. | |
| 2005/0090716 A1 | 4/2005 | Bonadio et al. | 2009/0326330 A1 | 12/2009 | Bonadio et al. | |
| 2005/0090717 A1 | 4/2005 | Bonadio et al. | 2010/0063362 A1 | 3/2010 | Bonadio et al. | |
| 2005/0096695 A1 | 5/2005 | Olich | 2010/0063364 A1 | 3/2010 | Bonadio et al. | |
| 2005/0131349 A1 | 6/2005 | Albrecht et al. | 2010/0081880 A1 | 4/2010 | Widenhouse et al. | |
| 2005/0148823 A1 | 7/2005 | Vaugh et al. | 2010/0081881 A1 | 4/2010 | Murray et al. | |
| 2005/0155611 A1 | 7/2005 | Vaugh et al. | 2010/0081995 A1 | 4/2010 | Widenhouse et al. | |
| 2005/0159647 A1 | 7/2005 | Hart et al. | 2010/0100043 A1 | 4/2010 | Racenet | |
| 2005/0192483 A1 | 9/2005 | Bonadio et al. | 2010/0113882 A1 | 5/2010 | Widenhouse et al. | |
| 2005/0192598 A1 | 9/2005 | Johnson et al. | 2010/0217087 A1 | 8/2010 | Bonadio et al. | |
| 2005/0197537 A1 | 9/2005 | Bonadio et al. | 2010/0228091 A1 | 9/2010 | Widenhouse et al. | |
| 2005/0203346 A1 | 9/2005 | Bonadio et al. | 2010/0228092 A1 | 9/2010 | Ortiz et al. | |
| 2005/0209510 A1 | 9/2005 | Bonadio et al. | 2010/0228094 A1 | 9/2010 | Ortiz et al. | |
| 2005/0222582 A1 | 10/2005 | Wenchell | 2010/0240960 A1 | 9/2010 | Richard | |
| 2005/0240082 A1 | 10/2005 | Bonadio et al. | 2010/0249523 A1 | 9/2010 | Spiegal et al. | |
| 2005/0241647 A1 | 11/2005 | Nguyen | 2010/0249524 A1 | 9/2010 | Ransden et al. | |
| 2005/0251124 A1 | 11/2005 | Zvuloni et al. | 2010/0249525 A1 | 9/2010 | Shelton, IV et al. | |
| 2005/0261720 A1 | 11/2005 | Caldwell et al. | 2010/0249694 A1 | 9/2010 | Choi et al. | |
| 2005/0267419 A1 | 12/2005 | Smith | 2010/0261972 A1 | 10/2010 | Widenhouse et al. | |
| 2005/0277946 A1 | 12/2005 | Greenhalgh | 2010/0261975 A1 | 10/2010 | Huey et al. | |
| 2005/0283050 A1 | 12/2005 | Gundlapalli et al. | 2010/0286484 A1 | 11/2010 | Stellon et al. | |
| 2005/0288558 A1 | 12/2005 | Ewers et al. | 2010/0298646 A1 | 11/2010 | Stellon et al. | |
| 2005/0288634 A1 | 12/2005 | O'Heeron et al. | 2011/0021877 A1 | 1/2011 | Fortier et al. | |
| 2006/0020164 A1 | 1/2006 | Butler et al. | 2011/0028891 A1 | 2/2011 | Okoniewski | |
| 2006/0020241 A1 | 1/2006 | Piskun et al. | 2011/0034935 A1 | 2/2011 | Kleyman | |
| 2006/0030755 A1 | 2/2006 | Ewers et al. | 2011/0034946 A1 | 2/2011 | Kleyman | |
| 2006/0041270 A1 | 2/2006 | Lenker | | | | |

| | | | |
|---|---|---|---|
| 2011/0034947 A1 | 2/2011 | Kleyman | |
| 2011/0071462 A1 | 3/2011 | Ewers et al. | |
| 2011/0071463 A1 | 3/2011 | Ewers et al. | |

FOREIGN PATENT DOCUMENTS

| | | |
|---|---|---|
| DE | 33 36 279 C2 | 1/1986 |
| DE | 37 39 532 | 12/1988 |
| DE | 37 37 121 | 5/1989 |
| DE | 296 00 939 | 6/1996 |
| DE | 19828009 | 12/1999 |
| EP | 0113520 | 7/1984 |
| EP | 0142262 | 5/1985 |
| EP | 0 517 248 | 12/1992 |
| EP | 0537768 | 4/1993 |
| EP | 0 807 416 | 11/1997 |
| EP | 0 849 517 | 6/1998 |
| EP | 0950376 | 10/1999 |
| EP | 1118657 | 7/2001 |
| EP | 1 125 552 | 8/2001 |
| EP | 1312318 | 5/2003 |
| EP | 1 407 715 | 4/2004 |
| EP | 2044889 | 4/2009 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| SU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO95/07056 | 3/1995 |
| WO | WO 95/22289 | 8/1995 |
| WO | WO95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO97/11642 | 4/1997 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO98/19853 | 5/1998 |
| WO | WO 98/35614 | 8/1998 |
| WO | WO98/35614 | 8/1998 |
| WO | WO 98/48724 | 11/1998 |
| WO | WO98/48724 | 11/1998 |
| WO | WO 99/03416 | 1/1999 |
| WO | WO 99/15068 | 4/1999 |
| WO | WO99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO00/32116 | 6/2000 |
| WO | WO 00/32119 | 6/2000 |
| WO | WO00/32120 | 6/2000 |
| WO | WO 00/32120 | 6/2000 |
| WO | WO00/35356 | 6/2000 |
| WO | WO 00/35356 | 6/2000 |
| WO | WO 00/54675 | 9/2000 |
| WO | WO00/54675 | 9/2000 |
| WO | WO 00/54676 | 9/2000 |
| WO | WO00/54676 | 9/2000 |
| WO | WO 00/54677 | 9/2000 |
| WO | WO00/54677 | 9/2000 |
| WO | WO 01/08563 | 2/2001 |
| WO | WO01/08581 | 2/2001 |
| WO | WO 01/08581 | 2/2001 |
| WO | WO 01/26558 | 4/2001 |
| WO | WO01/26559 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO02/34108 | 5/2002 |
| WO | WO 03/011153 | 2/2003 |
| WO | WO 03/011551 | 2/2003 |
| WO | WO 03/026512 | 4/2003 |
| WO | WO03/032819 | 4/2003 |
| WO | WO 03/032819 | 4/2003 |
| WO | WO 03/034908 | 5/2003 |
| WO | WO03/034908 | 5/2003 |
| WO | WO 03/061480 | 7/2003 |
| WO | WO03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2008/015566 | 2/2008 |
| WO | WO 2008/093313 | 8/2008 |
| WO | WO 2008/121294 | 10/2008 |
| WO | WO 2010/082722 | 7/2010 |
| WO | WO 2010/104259 | 9/2010 |

OTHER PUBLICATIONS

U.S. Appl. No. 10/436,522, filed May 13, 2003; Title: Laparoscopic Illumination Apparatus and Method, now USPN 6,939,296 issued Sep. 6, 2005.

U.S. Appl. No. 10/399,209, filed Aug. 22, 2003; Title: Wound Retraction Apparatus and Method, now USPN 6,958,037 issued Oct. 25, 2005.

U.S. Appl. No. 11/218,412, filed Sep. 1, 2005; Title: Wound Retraction Apparatus and Method, now USPN 7,238,154 issued Jul. 3, 2007.

U.S. Appl. No. 10/399,057, filed Apr. 11, 2003; Title: Sealed Surgical Access Device, now USPN 7,052,454 issued May 30, 2006.
U.S. Appl. No. 10/666,579; filed Sep. 17, 2003; Title: Surgical Instrument Access Device, now USPN 7,163,510 issued Jan. 16, 2007.
U.S. Appl. No. 10/052,297, filed Jan. 18, 2002; Title: Hand Access Port Device, now USPN 6,908,430 issued Jun. 21, 2005.
U.S. Appl. No. 08/015,765, filed Feb. 10, 1993; Title: Gas-Tight Seal Accomodating Surgical Instruments With a Wide Range of Diameters, now USPN 5,407,433 issued Apr. 18, 1995.
U.S. Appl. No. 08/040,373, filed Mar. 30, 1993; Title: Gas-Tight Seal Accomodating Surgical Instruments With a Wide Range of Diameters, now USPN 5,411,483 issued May 2, 1995.
U.S. Appl. No. 10/902,756, filed Jul. 29, 2004; Title: Hand Access Port Device, now abandoned.
U.S. Appl. No. 10/802,125, filed Mar. 15, 2004; Title: Surgical Guide Valve, now abandoned.
U.S. Appl. No. 10/516,198, filed Nov. 30, 2004; Title: Wound Retractor, now USPN 7,650,887 issued Jan. 26, 2010.
U.S. Appl. No. 10/927,551, filed Aug. 25, 2004; Title: Surgical Access System, now abandoned.
U.S. Appl. No. 11/244,647, filed Oct. 5, 2005; Title: Surgical Access Apparatus and Method, now USPN 7,481,765 issued Jan. 27, 2009.
U.S. Appl. No. 11/548,746, filed Oct. 12, 2006; Title: Method of Making a Hand Access Laparoscopic Device, now USPN 7,749,415 issued Jul. 6, 2010.
U.S. Appl. No. 11/548,765, filed Oct. 12, 2006; Title: Split Hoop Wound Retractor, now USPN 7,815,567 issued Oct. 26, 2010.
U.S. Appl. No. 11/548,767, filed Oct. 12, 2006; Title: Circular Surgical Retractor now USPN 7,704,207 issued Apr. 27, 2010.
U.S. Appl. No. 11/548,781, filed Oct. 12, 2006; Title: Wound Retractor With Gel Cap, now USPN 7,727,146 issued Jun. 1, 2010.
U.S. Appl. No. 11/548,955, filed Oct. 12, 2006; Title: Hand Access Laparoscopic Device, now USPN 7,736,306 issued Jun. 15, 2010.
U.S. Appl. No. 11/755,305, filed May 30, 2007; Title: Wound Retraction Apparatus and Method, now USPN 7,377,898 issued May 27, 2008.
U.S. Appl. No. 11/548,758, filed Oct. 12, 2007; Title: Split Hoop Wound Retractor With Gel Pad, now USPN 7,909,760 issued Mar. 22, 2011.
U.S. Appl. No. 12/693,242, filed Jan. 1, 2010; Title: Wound Retractor, now USPN 7,913,697 issued Mar. 29, 2011.
U.S. Appl. No. 12/768,328, filed Apr. 27, 2010; Title: Circular Surgical Retractor, now USPN 7,892,172 issued Feb. 22, 2011.
U.S. Appl. No. 12/791,666, filed Jun. 1, 2010; Title: Wound Retractor With Gel Cap, now USPN 7,883,461 issued Feb. 8, 2011.
U.S. Appl. No. 12/815,986, filed Jun. 15, 2010; Title: Hand Access Laparoscopic Device, now USPN 7,878,974 issued Feb. 1, 2011.
U.S. Appl. No. 10/695,295, filed Oct. 28, 2003; Title: Surgical Gel Seal.
U.S. Appl. No. 11/132,741, filed May 18, 2005; Title: Gas-Tight Seal Accomodating Surgical Instruments With a Wide Range of Diameters.
U.S. Appl. No. 11/245,709, filed Oct. 7, 2005; Title: Surgical Access System.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832; filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".

European Patent Office, European Search Report for European Application No. EP 04 00 2889, dated Sep. 13, 2004, entitled "Hand Access Port Device".
European Patent Office, International Search Report and The Written Opinion of the International Searching Authority for International Application No. PCT/US2006/040154, mailed Jan. 30, 2007.
European Patent Office, International Search Report and The Written Opinion of the International Searching Authority for International Application No. PCT/US2006/040073, mailed Jan. 26, 2007.
European Patent Office, International Search Report and The Written Opinion of the International Searching Authority for International Application No. PCT/US2006/039905, mailed Jan. 17, 2007.
European Patent Office, International Search Report and The Written Opinion of the International Searching Authority for International Application No. PCT/US2006/039883, mailed Jan. 31, 2007.
European Patent Office, International Search Report and The Written Opinion of the International Searching Authority for International Application No. PCT/US2006/039800, mailed Apr. 16, 2007.
European Patent Office, International Search Report and The Written Opinion of the International Searching Authority for International Application No. PCT/US2006/039799, mailed Mar. 27, 2007.
European Search Report for corresponding EP 08253236 date of mailing is Feb. 10, 2009 (6 pages).
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484.
International Searching Authority/US, International Search Report and the Written Opinion of the International Searching Authority for International Application No. PCT/US01/29682.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan.
The International Bureau of WIPO, International Preliminary Report on Patentability, dated Aug. 29, 2006, for International Application No. PCT/US2004/028250.
The International Bureau of WIPO, International Preliminary Report on Patentability, dated Apr. 16, 2008, for International Application No. PCT/US2006/039799.
The International Bureau of WIPO, International Preliminary Report on Patentability for International Application No. PCT/US2006/039800 dated Apr. 16, 2008.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.
Kagaya, Laparascopic cholecystecomy via two ports, using the "Twin-Port" system, J. Hepatobiliary Pancreat Surg (2001) 8:76-80.
International Search Report and Written Opinion in PCT/IE2005/000113 mailed on Feb. 22, 2006.
International Search Report and Written Opinion in PCT/IE2007/000050 mailed on Aug. 13, 2007.
Declaration of John R. Brustad dated Dec. 10, 2009, submitted in U.S. Appl. No. 11/548,955, including Appendices A-D regarding product sales brochures and production drawings from 2001 and 2005.

The International Searching Authority, The International Search Report and Written Opinion of the International Searching Authority for International Application No. PCT/US08/63445, mailed Sep. 29, 2008.
The International Searching Authority, The International Search Report and Written Opinion of the International Searching Authority for International Application No. PCT/US08/063463 mailed Sep. 10, 2008.
The International Bureau of WIPO, International Preliminary Report on Patentability for International Application No. PCT/US2008/063463, dated Nov. 17, 2009, entitled "Surgical Retractor".
The International Bureau of WIPO, International Preliminary Report on Patentability for International Application No. PCT/US08/63445, issued Nov. 17, 2009, entitled "Surgical Retractor with Gel Pad".
International Searching Authority—US, International Search Report and Written Opinion of the International Searching Authority for International Application No. PCT/US04/25511, mailed Nov. 7, 2007.
International Bureau of WIPO, International Report on Patentability for International Application No. PCT/US04/25511, mailed Dec. 6, 2007.
European Patent Office, European Search Report for European Patent No. 11172709.5, dated Aug. 16, 2011.
European Patent Office, European Search Report for European Patent No. 11172706.1, dated Aug. 16, 2011.
European Patent Office, International Search Report and The Written Opinion of the International Searching Authority for International Application No. PCT/2006/039799 mailed Mar. 27, 2007.
The International Bureau of WIPO, International Preliminary Report on Patentability dated Apr. 16, 2008 for PCT Application No. PCT/US2006/039799.
European Patent Office, International Search Report and The Written Opinion of the International Searching Authority for International Application No. PCT/2006/040073 mailed Jan. 26, 2007.
European Patent Office, International Search Report and The Written Opinion of the International Searching Authority for International Application No. PCT/2006/039905 mailed Jan. 17, 2007.
European Patent Office, International Search Report and The Written Opinion of the International Searching Authority for International Application No. PCT/2006/039883, mailed Jan. 31, 2007.
European Patent Office, International Search Report and The Written Opinion of the International Searching Authority for International Application No. PCT/2006/039800, mailed Apr. 16, 2007.
US 5,344,646, Chen (withdrawn).
Neil Sheehan, Supplemental Expert Report of Neil Sheehan, Re: U.S. Patent No. 5,741,298, United States District Court for the Central District of California, Civil Action No. SACV 3-1322 JVS, Aug. 9, 2005.
Horigane, et al., Technical Note: Development of a Duodoenal Cannula for Sheep, Journal of Animal Science, Apr. 1992, vol. 70, Issue 4, pp. 1216-1219.
Horigane, et al., Silicone Rumen Cannula with a Soft Cylindrical Part and a Hard Flange, Journal of Dairy Science, Nov. 1989, vol. 72, No. 11, pp. 3230-3232.
McSweeney, Cannullation of the Rumen in Cattle and Buffaloes, Australian Veterinary Journal, Aug. 1989, vol. 66, No. 8, pp. 266-268.
Yamazaki et al., Diurnal Changes in the Composition of Abomasal Digesta in Fasted and Fed Sheep, The Tohoku Journal of Argircultural Research, Mar. 1987, vol. 37, No. 3-4, pp. 49-58.
Co-Pending U.S. Appl. No. 10/381,220, filed Mar. 20, 2003; Title: Surgical Access Apparatus and Method.
Co-Pending U.S. Appl. No. 10/516,198, filed Nov. 30, 2004; Title: Wound Retractor.
Co-Pending U.S. Appl. No. 10/927,551; filed Aug. 25, 2004; Title: Surgical Access System.
Co-Pending U.S. Appl. No. 11/244,647, filed Oct. 5, 2005; Title: Surgical Access Apparatus and Method.
Co-Pending U.S. Appl. No. 11/245,709, filed Oct. 7, 2005; Title: Surgical Access System.
Co-Pending U.S. Appl. No. 11/330,661, filed Jan. 12, 2006; Title: Sealed Surgical Access Device.
Co-Pending U.S. Appl. No. 11/548,746, filed Oct. 12, 2006; Title: Method of Making a Hand Access Laparoscopic Device.

Co-Pending U.S. Appl. No. 11/548,758, filed Oct. 12, 2006; Title: Split Hoop Wound Retractor With Gel Pad.
Co-Pending U.S. Appl. No. 11/548,765, filed Oct. 12, 2006; Title: Split Hoop Wound Retractor.
Co-Pending U.S. Appl. No. 11/548,767; filed Oct. 12, 2006; Title: Circular Surgical Retractor.
Co-Pending U.S. Appl. No. 11/548,781, filed Oct. 12, 2006; Title: Wound Retractor With Gel Cap.
Co-Pending U.S. Appl. No. 11/548,955, filed Oct. 12, 2006; Title: Hand Access Laparoscopic Device.
Co-Pending U.S. Appl. No. 11/564,409; filed Nov. 29, 2006; Title: Surgical Instrument Access Device.
Co-Pending U.S. Appl. No. 11/755,305, filed May 30, 2007; Title: Wound Retraction Apparatus and Method.
Co-Pending U.S. Appl. No. 12/108,400, filed Apr. 23, 2008; Title: Wound Retraction Apparatus and Method.
Co-Pending U.S. Appl. No. 12/358,080, filed Jan. 22, 2009; Title: Surgical Instrument Access Device.
The International Bureau of WIPO, The International Report on Patentability for International Application No. PCT/US2009/060540, dated Apr. 19, 2011.
European Patent Office, The International Search Report and Written Opinion of the International Searching Authority for International Application No. PCT/US09/060540 mailed Feb. 4, 2010, titled "Single Port Access System".

* cited by examiner

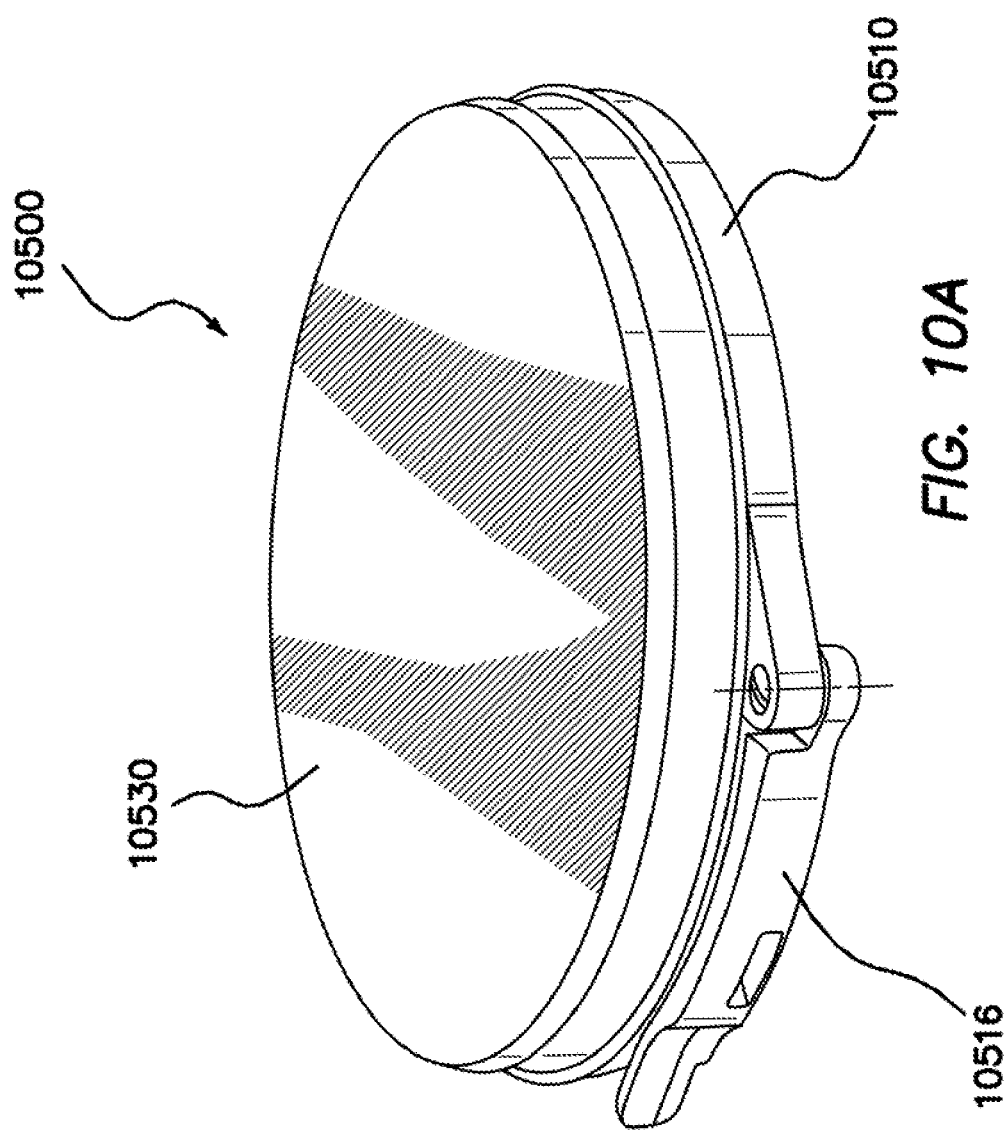

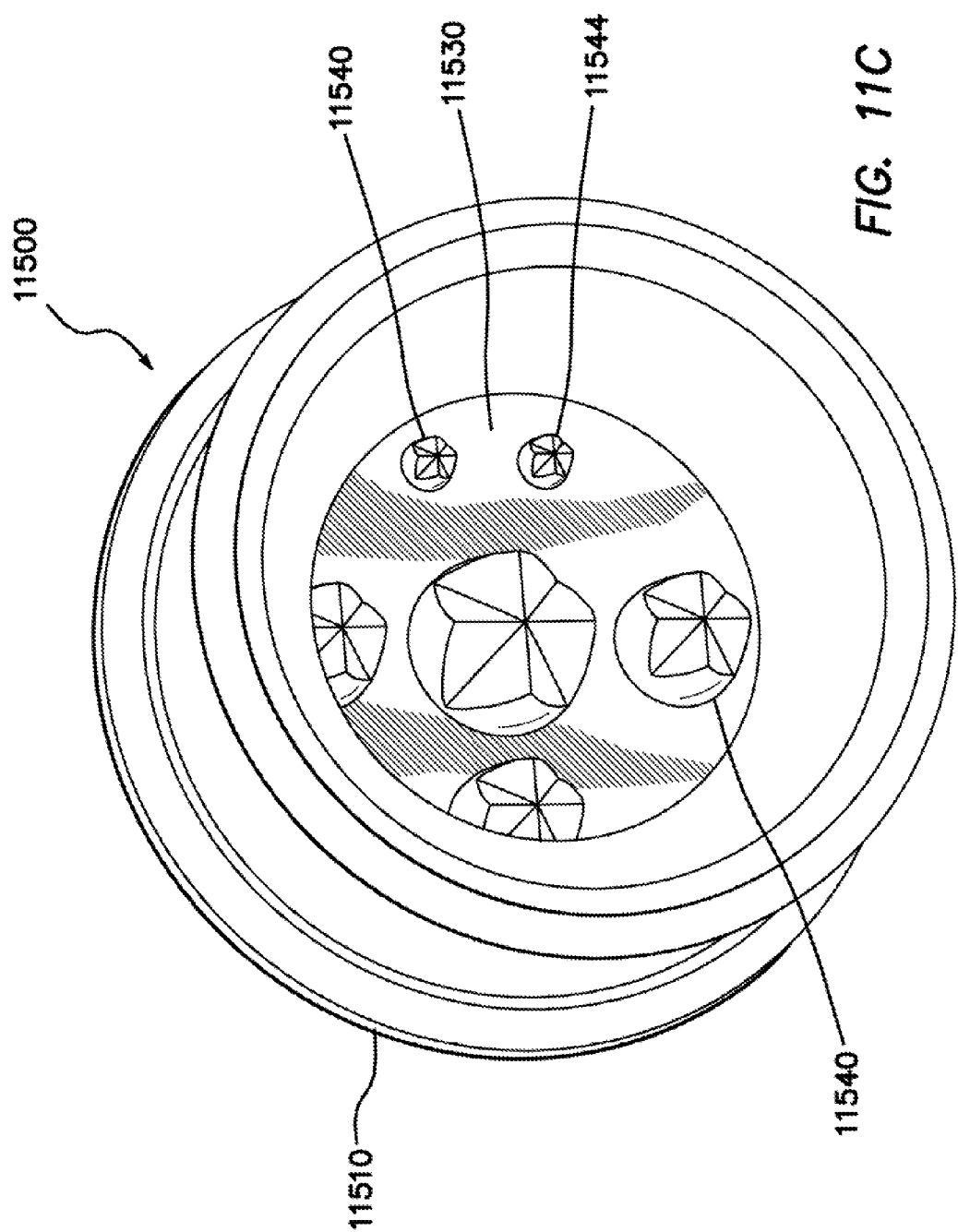

SINGLE PORT ACCESS SYSTEM

CROSS-REFERENCE TO RELATED APPLICATION

This application claims the benefit of U.S. Application No. 61/104,963, filed Oct. 13, 2008, the entire disclosure of which is incorporated by reference.

BACKGROUND

1. Technical Field

This application is generally directed to surgical devices, and more particularly, to a single-port laparoscopic access system.

2. Description of the Related Art

Access devices are commonly used in surgery to facilitate the introduction of various surgical instruments into natural biological vessels, conduits, orifices, cavities, and other interior regions of the body. These access devices include, for example, devices that facilitate the introduction of a needle into a vessel, and trocars that facilitate the introduction of laparoscopic instruments into the abdomen of the body.

Some of these access devices are introduced into regions that include a fluid or gas under pressure. In the case of a needle access device, the pressure may be from a liquid, such as blood. In the case of a trocar, the pressure may be from a gas, such as an insufflation gas. In either case, it is desirable to provide for the introduction of the surgical instrument into the cavity without permitting the escape of the pressurized fluid or gas.

In the case of trocars, a cannula at the distal end of the trocar is typically connected to a seal housing at the proximal end of the trocar. Together the cannula and housing form a working channel through which various instruments can be inserted to access the cavity. Seal mechanisms are commonly disposed in the housing and include a septum valve that seals the working channel when an instrument is in place, and a zero closure valve that seals the working channel when the instrument is removed.

Current surgical access ports allow for single instrument access through each port, or allow for multiple instrument access through a rigid cannula. Some devices, such as transanal endoscopic microsurgery (TEMS) units, require that instruments be placed through fixed points located on the device, and also require that the device be attached to the surgical table to support the weight of the device, as well as to locate the position of the device respective to the patient. These devices do not provide flexibility to the surgeon in selecting instrument size, and they restrict instrument movement with their rigid cannulas. Additionally, surgeons are performing laparoscopic surgical procedures through a single or a limited number of access ports. In these procedures, the surgeon to places multiple instruments through a single or a limited number of access ports. The procedures may be performed through a single two (2) centimeter incision at the umbilicus, or in certain cases, trans-vaginally or trans-anally. What is needed is a system that meets the needs of these new procedures and allows more options for the surgeons.

SUMMARY OF THE INVENTION

Embodiments of a surgical access system useful for single or limited port procedures comprise a trocar comprising a fixation cannula, a retractor, and a gel cap removably coupled to the retractor. The gel cap comprises a gel pad that acts as an artificial body wall, through which instruments may be inserted into a body cavity, either directly or through one or more trocars. The fixation cannula comprises a retainer and a bolster, which together, capture the artificial body wall therebetween, thereby fixing the trocar thereto. The gel pad permits flexible instrument placement, as well as translational and angular degrees of freedom for the instruments while maintaining a gas tight seal.

Some embodiments provide a surgical access system and a method for using the same. Embodiments of the access system comprise a trocar comprising: a fixation cannula comprising a tubular cannula body comprising a proximal end, a distal end, a longitudinal axis extending from the proximal end to the distal end; and a cannula wall defining a cannula lumen; a seal assembly coupled to the proximal end of the cannula body; a retainer extending from the cannula body; a locking component disposed on the cannula body and spaced from the retainer; and a bolster engagable to the locking component. The trocar has an insertion configuration in which the bolster is not engaged to the locking component, the trocar has a fixation configuration in which the bolster is engaged to the locking component, and in the fixation configuration, the retainer and the bolster are dimensioned and configured to capture an artificial body wall therebetween, thereby fixing the cannula to the artificial body wall.

In some embodiments, the trocar is a 5-mm trocar.

In some embodiments, the cannula comprises at least one of polycarbonate and polyester.

In some embodiments, the seal assembly comprises a septum valve and a duckbill valve.

In some embodiments, the retainer is disposed at the distal end of the cannula body and the locking component is proximal of the retainer. In some embodiments, the retainer comprises a radially extending flange. In some embodiments, a diameter of the retainer flange is from about 1.5 to about 2.5 times wider than an outer diameter of the cannula body. In some embodiments, a distal end of the retainer tapers.

In some embodiments, the locking component comprises an enlarged section.

In some embodiments, the locking component comprises a circumferential lip. In some embodiments, the locking component comprises screw threads. In some embodiments, the locking component comprises a plurality of circumferential slots. In some embodiments, the locking component comprises a ratchet.

In some embodiments, the bolster comprises an elastomeric material. In some embodiments, the bolster comprises a torus comprising an opening through with the cannula body extends. In some embodiments, the bolster comprises screw threads. In some embodiments, the bolster comprises at least one pawl dimensioned to engage a ratchet on the locking component. In some embodiments, the bolster comprises a clip dimensioned for engaging the locking component. In some embodiments, a diameter of the bolster is from about 0.8 to about 2 times a diameter of a flange.

In some embodiments, in the fixation configuration, the locking component resists disengagement of the bolster. In some embodiments, in the fixation configuration, a distance between the retainer and the bolster is adjustable.

Some embodiments further comprise an obturator.

Some embodiments further comprise an artificial body wall. In some embodiments, the artificial body wall comprises a gel pad. In some embodiments, the gel pad is coupled to a cap ring, thereby defining a gel cap. Some embodiments further comprise an adjustable wound retractor, wherein the adjustable wound retractor is couplable to the gel cap.

Some embodiments of the method comprise a method for fixing a trocar comprising a fixation cannula to an artificial body wall. The method comprises: converting the trocar into the insertion configuration; inserting the distal end of the cannula body through an artificial body wall; transforming the trocar to the fixation configuration by engaging the bolster to the locking component, thereby capturing the artificial body wall between the retainer and the bolster.

Some embodiments further comprise inserting an obturator through the trocar.

Some embodiments further comprise adjusting a distance between the bolster and the retainer in the fixation configuration.

Some embodiments provide a surgical access system comprising: an adjustable wound retractor comprising: an proximal ring, distal ring, and a flexible, tubular retraction sheath extending between the proximal ring and the distal ring, wherein the proximal ring is rotatable around an annular axis thereof, thereby adjusting a length of the retraction sheath between the proximal ring and the distal ring; a gel cap comprising a cap ring and a gel pad coupled with the cap ring, wherein the cap ring is engagable with the proximal ring; and a trocar comprising: a fixation cannula comprising a tubular cannula body comprising a proximal end, a distal end, a longitudinal axis extending from the proximal end to the distal end; and a cannula wall defining a cannula lumen; a seal assembly coupled to the proximal end of the cannula body; a retainer extending from the cannula body; a locking component disposed on the cannula body and spaced from the retainer; and a bolster engagable to the locking component. The trocar has an insertion configuration in which the bolster is not engaged to the locking component, the trocar has a fixation configuration in which the bolster is engaged to the locking component, and in the fixation configuration, the retainer and the bolster are dimensioned and configured to capture the gel pad therebetween, thereby fixing the cannula to the gel pad.

Accordingly, some embodiments provide a surgical access port adapted for performing laparoscopic surgical procedures at a single access site wherein an incision is made in the abdominal wall of a patient and the abdominal cavity is pressurized with an insufflation gas, the access port adapted to provide access to the abdominal cavity for surgical procedures while maintaining insufflation pressure in the abdominal cavity, the surgical access port comprising: an adjustable wound retractor comprising: a proximal ring, wherein the proximal ring is configured to be disposed proximate the outer surface of the abdominal wall of the patient and substantially surround the incision; a retraction sheath comprising a tubular wall, a proximal portion coupled to the proximal ring during use, and a distal portion, wherein the retraction sheath is configured to be disposed through the incision and line the incision, and wherein the retraction sheath is adjustable to retract the incision; and a distal ring coupled to the distal portion of the retraction sheath, wherein the distal ring is configured to be disposed proximate the inner surface of the abdominal wall and substantially surround the incision; and a gel cap configured to be coupled to the proximal ring, comprising: a cap ring, wherein the cap ring is configured to substantially surround the incision; a gel pad disposed within the cap ring; and a plurality of sealing valves operatively attached to the gel pad, wherein the plurality of sealing valves at least partially form a plurality of access channels through the gel pad, and wherein the plurality of sealing valves are configured to form seals with instruments extending through the sealing valves and form seals in the absence of any instruments extending through the sealing valves.

In some embodiments, at least a portion of at least one of the sealing valves defines an orifice. In some embodiments, at least a portion of at least one of the sealing valves comprises a septum seal. In some embodiments, at least a portion of at least one of the sealing valves comprises a duck bill valve. In some embodiments, at least one of the sealing valves has a low profile. In some embodiments, at least one of the sealing valves has a first size to accommodate an instrument of the first size, and at least another of the sealing valves has a second size to accommodate an instrument of the second size.

In some embodiments, at least one of the sealing valves is configured such that the sealing valve is repositionable relative to the cap ring during use. In some embodiments, at least one of the sealing valves is configured such that the sealing valve is translatable relative to the cap ring during use. In some embodiments, at least one of the sealing valves is configured such that the sealing valve is pivotable relative to the cap ring during use. In some embodiments, at least one of the sealing valves is configured such that the sealing valve is held generally stationary relative to the cap ring during use.

In some embodiments, the gel cap is configured to be removably coupled to the proximal ring during use. In some embodiments, the gel cap is fixed to the proximal ring.

In some embodiments, the proximal ring of the wound retractor is rotatable to adjustably retract the incision during use. In some embodiments, the retraction sheath is stretchable to adjustably retract the incision during use.

Some embodiments additionally comprise a tether coupled to the distal ring. In some embodiments, at least a portion of the distal ring has a non-circular cross section that facilitates folding the distal ring and insertion through the incision. In some embodiments, the distal ring has a tear-drop-shaped cross section that facilitates folding the distal ring and insertion through the incision. In some embodiments, the distal ring comprises at least one notch that facilitates folding of the distal ring and insertion through the incision.

Some embodiments provide a surgical access port adapted for performing a surgical procedure at an access site wherein a body cavity of a patient is pressurized with an insufflation gas, the access port adapted to provide access to the body cavity for surgical procedures while maintaining insufflation pressure in the body cavity, the surgical access port comprising: an adjustable retractor comprising: a proximal ring, wherein the proximal ring is configured to be disposed proximate the outer surface of the body wall of the patient; a retraction sheath comprising a tubular wall, a proximal portion coupled to the proximal ring during use, and a distal portion, wherein the retraction sheath is configured to be disposed through an opening in the body wall of the patient, and wherein the retraction sheath is adjustable to retract the opening in the body wall; and a distal ring coupled to the distal portion of the retraction sheath, wherein the distal ring is configured to be disposed proximate the inner surface of the body wall of the patient; and a sealing cap configured to be coupled to the proximal ring, comprising: a cap ring substantially surrounding a flexible material disposed within the cap ring; and a sealing valve positioned within the cap ring and substantially surrounded by and operatively attached to the flexible material, wherein the sealing valve at least partially forms an access channel through the flexible material, and wherein the sealing valve is configured to form a seal with an instrument extending through the sealing valve and form a seal in the absence of any instrument extending through the sealing valve.

In some embodiments, the flexible material comprises a gel.

In some embodiments, the sealing valve is repositionable relative to the cap ring during use. In some embodiments, the sealing valve is translatable relative to the cap ring during use. In some embodiments, the sealing valve is pivotable relative to the cap ring during use.

In some embodiments, the sealing cap comprises a plurality of sealing valves positioned within the cap ring and substantially surrounded by the flexible material, wherein the plurality of sealing valves at least partially form a plurality of access channels through the flexible material, and wherein the plurality of sealing valves are configured to form seals with instruments extending through the sealing valves and form seals in the absence of any instruments extending through the sealing valves.

Some embodiments additionally comprise a tether coupled to the distal ring. In some embodiments, at least a portion of the distal ring has a non-circular cross section that facilitates folding the distal ring and insertion through the incision.

Some embodiments provide a surgical access port adapted for performing laparoscopic surgical procedures at an access site wherein an incision is made in the abdominal wall of a patient and the abdominal cavity is pressurized with an insufflation gas, the access port adapted to provide access to the abdominal cavity for surgical procedures while maintaining insufflation pressure in the abdominal cavity, the surgical access port comprising: an adjustable wound retractor having a proximal ring, a distal ring, and a retraction sheath extending between the proximal ring and the distal ring, the proximal ring being configured to be disposed proximate the outer surface of the abdominal wall of the patient, the distal ring being configured to be disposed proximate the inner surface of the abdominal wall of the patient, and the a retraction sheath comprising a tubular wall having a proximal portion coupled to the proximal ring during use and a distal portion coupled to the distal ring during use, wherein the retraction sheath is configured to be disposed through the incision and line the incision, and wherein the retraction sheath is adjustable to retract the incision; and a sealing cap configured to be coupled to the proximal ring during use, the sealing cap comprising a plurality of sealing valves, wherein the plurality of sealing valves at least partially form a plurality of access channels through the sealing cap, wherein the plurality of sealing valves are configured to form seals with instruments extending through the sealing valves and form seals in the absence of any instruments extending through the sealing valves, and wherein at least one of the sealing valves is repositionable relative to at least another one of the sealing valves during use.

In some embodiments, the sealing cap comprises a gel.

In some embodiments, the at least one repositionable sealing valve is translatable relative to the at least another one of the sealing valves. In some embodiments, the at least one repositionable sealing valve is pivotable relative to the at least another one of the sealing valves.

Some embodiments additionally comprise a tether coupled to the distal ring. In some embodiments, at least a portion of the distal ring has a non-circular cross section that facilitates folding the distal ring and insertion through the incision.

Some embodiments provide an access device system comprising: a retractor and a gel cap. The retractor comprises an inner ring, an outer ring, and a flexible sleeve extending between the inner ring and the outer ring. The outer ring comprises an outer component and an inner component, wherein the inner component defines an annular axis around which the outer component is rotatable, thereby winding and unwinding the flexible sleeve therearound. The gel cap comprises an annular cap ring coupled to the outer ring of the retractor and a gel pad disposed in and coupled to the annular cap ring. The gel pad does not comprise a preformed access channel therethrough.

Some embodiments provide an access device system comprising: a retractor and a gel cap. The retractor comprises an inner ring, an outer ring, and a flexible sleeve extending between the inner ring and the outer ring. The outer ring comprises an outer component and an inner component, wherein the inner component defines an annular axis around which the outer component is rotatable, thereby winding and unwinding the flexible sleeve therearound. The gel cap comprises an annular cap ring coupled to the outer ring of the retractor and a gel pad disposed in and coupled to the annular cap ring. At least one access port comprising a first seal and a second seal is at least partially embedded in the gel pad, wherein the first seal comprises an instrument seal and the second seal comprises a zero seal.

Some embodiments of the access device system further comprise a trocar comprising a longitudinal axis defining an access channel; a proximal end; a distal end; a tubular cannula; a seal assembly disposed at the proximal end of the cannula; and a retainer disposed at the distal end of the cannula. The seal assembly comprises an instrument seal and a zero seal. The proximal end of the retainer comprises a face that is substantially perpendicular to the longitudinal axis. A diameter of the retainer convergently tapers from the proximal end to the distal end thereof.

Some embodiments provide a single port access device system comprising a retractor and an artificial body wall couplable to the retractor, wherein the artificial body wall comprises a plurality of access channels dimensioned and configured for instrument access therethrough, and wherein instruments inserted through the access channels are relatively translatable and relatively pivotable.

BRIEF DESCRIPTION OF THE DRAWINGS

FIG. 10A is a top perspective view of an embodiment of a gel cap.

FIG. 11C is a bottom perspective view of the gel cap illustrated in FIG. 11A.

Similar components have similar reference numbers throughout.

DETAILED DESCRIPTION OF CERTAIN EMBODIMENTS

Figure 1:
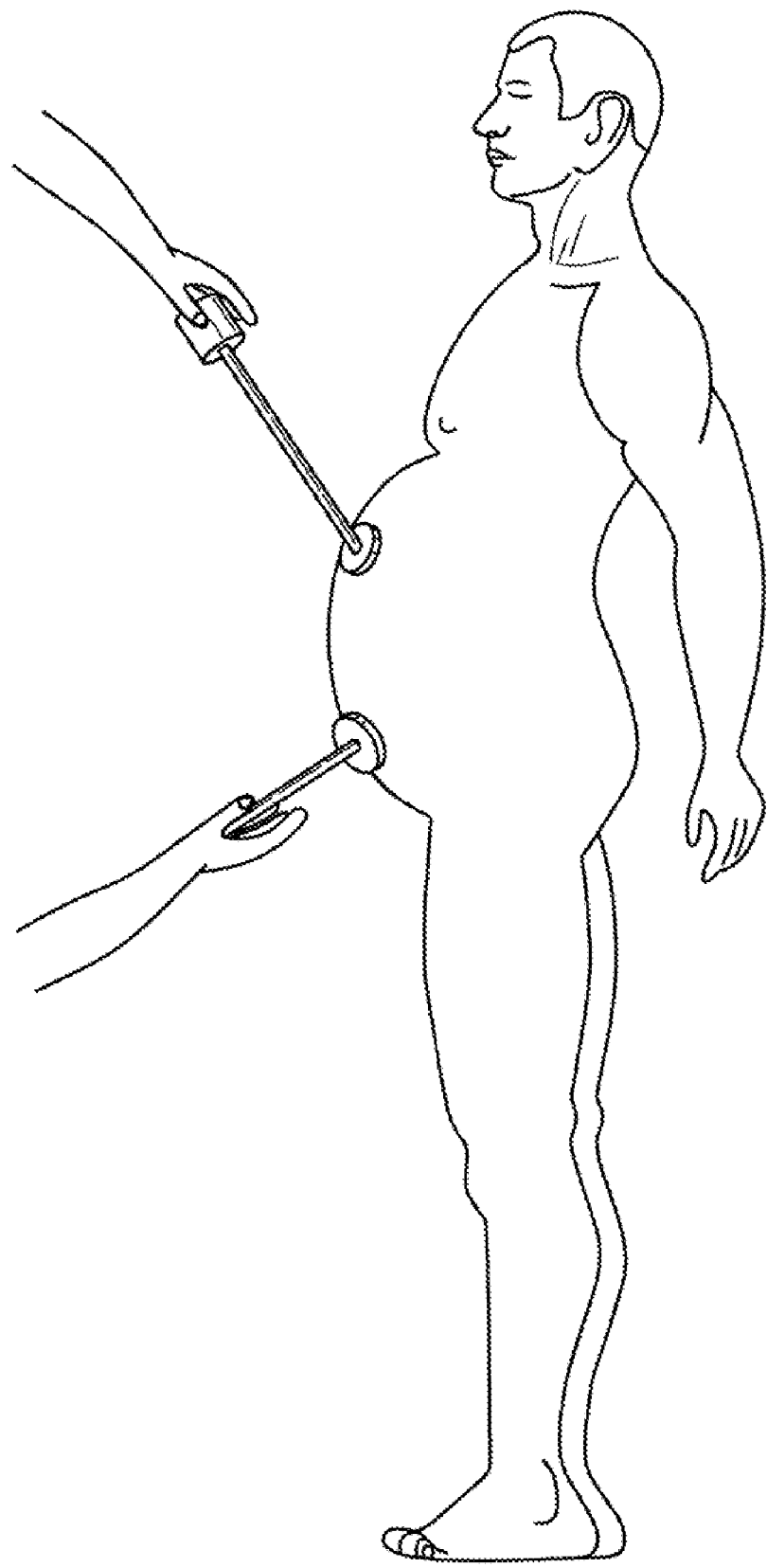
FIG. 1 is a side view of a patient in surgery illustrating an embodiment of the access device positioned on the abdomen and in use.
Figure 2:
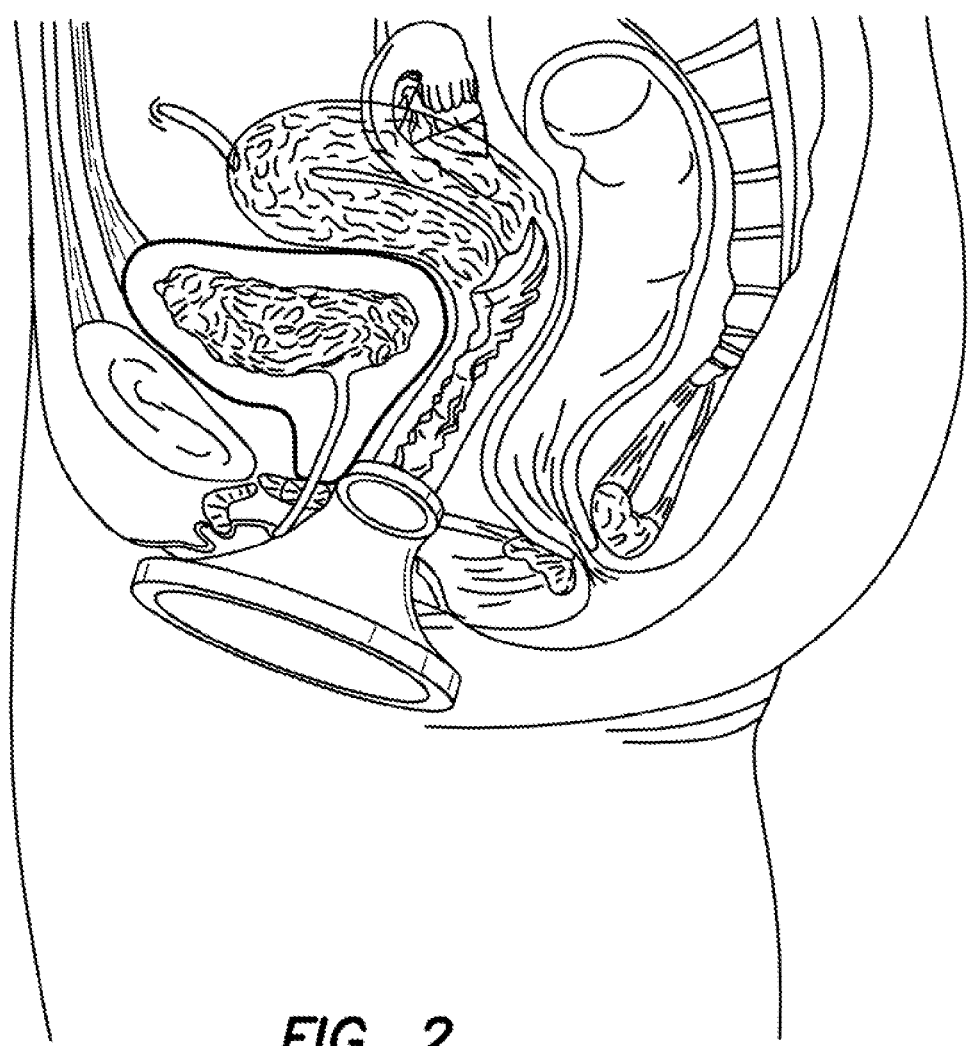
FIG. 2 is a cross-sectional side view illustrating an embodiment of the access device, with the wound retractor retracting the vagina of a patient, and the gel cap sealing the opening of the wound retractor.
Figure 3:
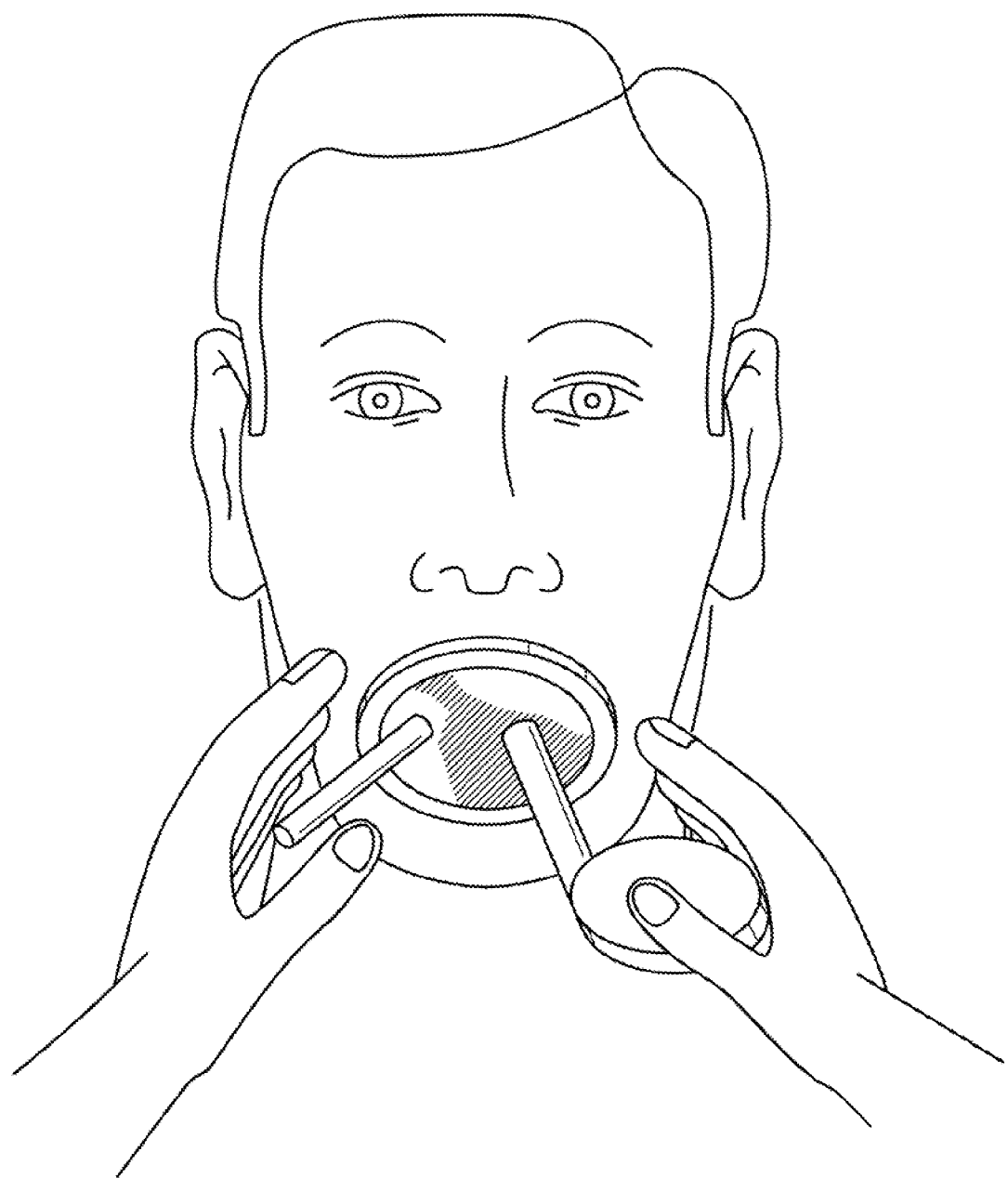
FIG. 3 is a front view illustrating an embodiment of the access device deployed and in use at the mouth of the patient.

Embodiments of the surgical instrument access device system are useful, for example, for single incision, single port, and/or limited port laparoscopic surgical procedures, for example, abdominal (FIG. 1), transvaginal (FIG. 2), transoral (FIG. 3), and transanal (FIG. 4) procedures.

Figure 5:
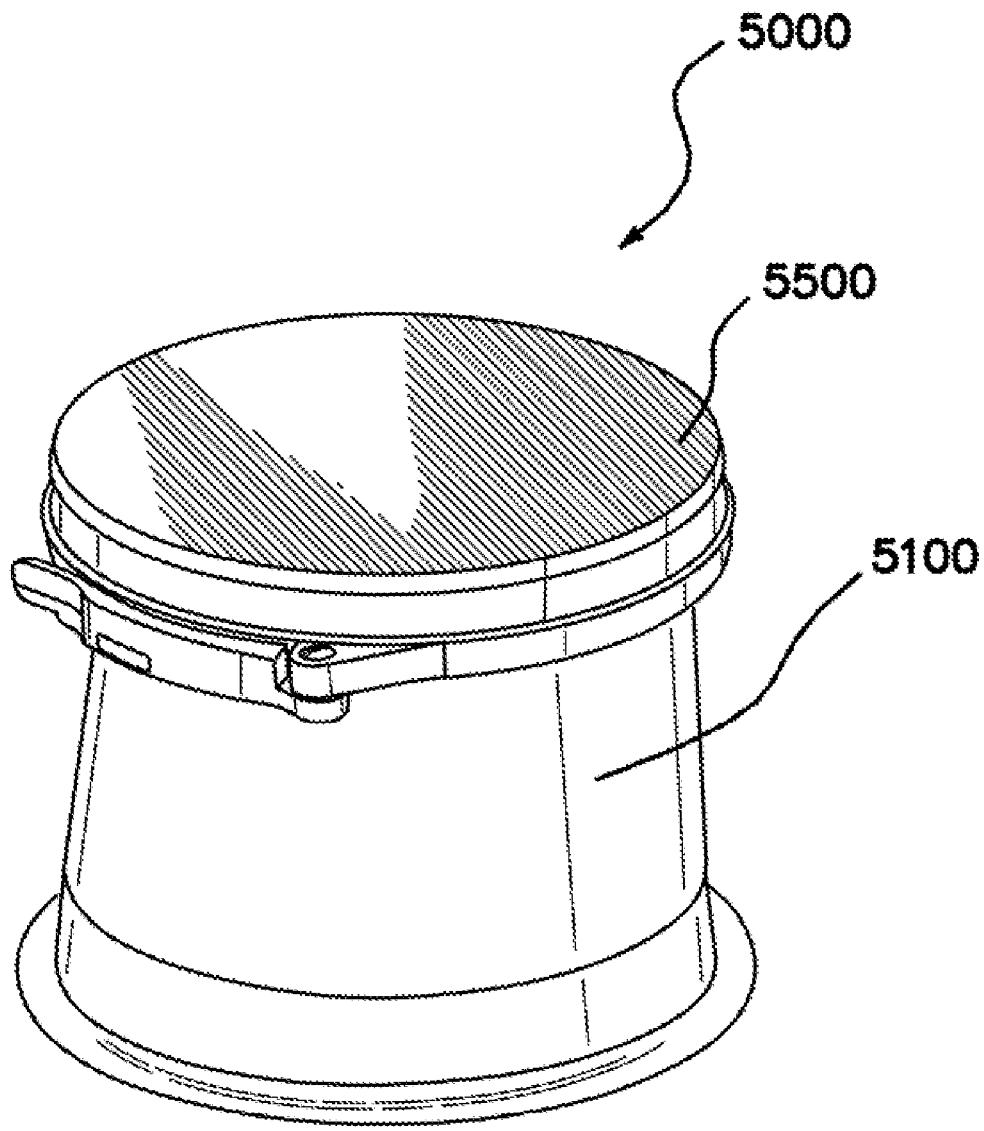
FIG. 5 is a perspective view of an embodiment of an access device comprising a cap and a retractor.

FIG. 5 illustrates a perspective view of an embodiment of an access device system 5000 comprising a retractor 5100 and a cap 5500, which is useful in single port and/or limited port procedures. The retractor or surgical wound retractor 5100 is placed and/or positioned into, across, and/or through a surgical incision and/or body orifice to enlarge, reshape, and/or isolate the incision or body orifice. The cap 5500 provides an artificial body wall through which instruments access the interior of a patient's body, for example, a body cavity. The components of the access device 5000 comprise any suitable biologically compatible materials. Other embodiments of access device systems are described in U.S. Patent Publication No. 2007/0088204 A1, the disclosure of which is incorporated.

Figure 6A:
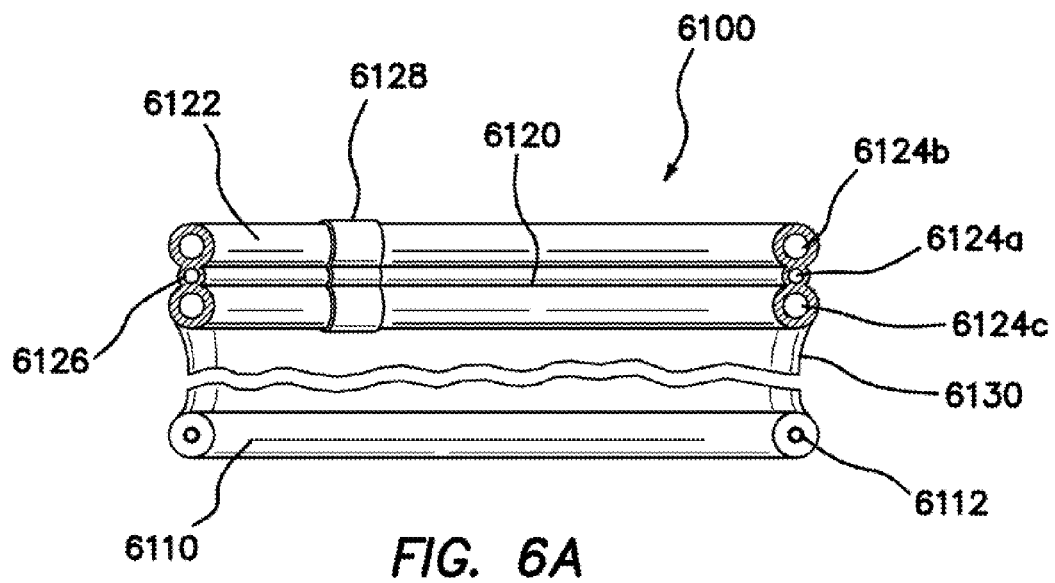
FIG. 6A is a partial side cross section of an embodiment of a retractor.

The embodiment of the retractor 6100 illustrated in a partial side cross section in FIG. 6A comprises an inner or distal ring 6110, an outer or proximal ring 6120, and a sleeve or retraction sheath 6130 extending between and coupling the inner ring 6110 and the outer ring 6120. The sleeve 6130 comprises a flexible membrane, which is substantially cylindrical in the illustrated embodiment. In other embodiments, the sleeve 6130 has another shape, for example, an oval cross section. Embodiments of the sleeve 6130 comprise a flexible, semi-transparent polymer film. Some embodiments of the sleeve 6130 comprise one or more coatings that provide additional functionality, for example, an anti-microbial coating.

Embodiments of the inner ring 6110 are sufficiently flexible and compliant to be compressed and/or deformed for insertion through an incision and/or body orifice. When subsequently released within an associated body cavity, the inner ring 6110 substantially returns to its original shape or footprint. In some embodiments, the inner ring 6110 assumes a substantially circular shape in a relaxed state, for example, when released within a body cavity. In other embodiments, the inner ring 6110 has another shape in the relaxed state, for example, an oval. The inner ring 6110 assumes a different shape when compressed for insertion through an incision or body orifice, for example, a substantially oval shape, a generally linear shape, a tear-drop shape, or another suitable shape. Those skilled in the art will recognize that in other embodiments, the inner ring 6110 in the relaxed state has a shape other than round, for example, oval, elliptical, or D-shaped. In other embodiments, the inner ring 6110 is substantially rigid, that is, non-compliant under the ordinary conditions under which it is used.

Figure 6B:
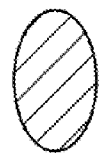
FIGS. 6B-6D illustrate cross sections of embodiments of inner rings.
Figure 6C:
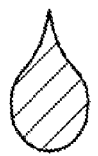
Figure 6D:
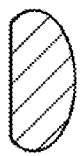

Embodiments of the inner ring 6110 comprise a circular cross section as illustrated in FIG. 6A. In other embodiments, the inner ring 6110 comprises another cross-sectional shape, for example, at least one of oval or elliptical (FIG. 6B), tear-drop shaped (FIG. 6C), and D-shaped (FIG. 6D). Those skilled in the art will understand that other cross sections are used in other embodiments. Some embodiments of the inner ring 6110 comprise at least one notch and/or weak spot, which facilitate folding or deforming the inner ring 6110, thereby facilitating insertion and/or removal of the inner ring 6110.

Some embodiments of the inner ring 6110 comprise one or more lumens extending therethrough. For example, the embodiment of the inner ring 6110 illustrated in FIG. 6A comprises a lumen 6112. Embodiments of the lumen 6112 provide at least one of improved resilience and improved flexibility. In some embodiments a wire is disposed within the lumen 6112, for example, a spring-metal wire, thereby modifying the resilience of the inner ring 6110. In some embodiments, the lumen or lumens 6112 improve the compressibility of the inner ring 6110, thereby facilitating insertion into and/or removal from a body cavity. For example, in some embodiments, the lumen(s) 6112 increase the flexibility of the inner ring 6110, for example, permitting a smaller radius fold and/or a flatter compressed state. In some embodiments, a more flexible inner ring 6110 improves sealing of the retractor to an inner wall of the body cavity. In some embodiments, an inner ring 6110 comprising one or more lumens 6112 compresses to a smaller size and/or cross section than a similar inner ring 6110 without a lumen, for example, by collapsing the lumen(s) 6112 in the compressed state.

In some embodiments, the inner ring 6110 is manufactured as a monolithic ring or toroid. In other embodiments, the inner ring 6110 is manufactured from a generally linear body comprising a first end and a second end, which are brought together to provide a closed form. The first end and second end are then joined using any suitable means or method known in the art, for example, by at least one of adhesively, welding, melting, mechanically, and the like. In some embodiments, the first end and second end of the linear body are joined using a coupler. In some embodiments, the coupler engages the lumen 6112, for example, comprising a first finger and a second finger dimensioned to be received within the lumen 6112 at the first end and the second end of the body, respectively, where the first and second fingers and extend in opposite directions from a common locus of the coupler. In embodiments, the coupler prevents relative rotation between the first end and the second end of the body of the coupler.

Returning to FIG. 6A, the outer ring 6120 includes an outer component 6122 and an inner component. In the illustrated embodiment, the outer component 6122 has a substantially circular footprint and a substantially oval cross section. In other embodiments, the outer component 6122 has another cross-sectional shape, for example, rectangular, hexagonal, octagonal, or another suitable shape. In the illustrated embodiment, a cross-sectional height of the outer component 6122 is larger than a cross-sectional width thereof. In some embodiments, a ratio between the height and width of the cross-section relates to factors including an overall hardness and/or rigidity of the outer component 6122 and a diameter of the outer ring 6120. More particularly, a softer outer component 6122 correlates with a larger ratio between the cross-sectional height and width of the outer component 6122 in some embodiments. Similarly, increasing the diameter of the outer component 6122 increases the ratio between the cross-sectional height and width of the outer component 6122. Embodiments of the outer component 6122 comprise a thermoplastic elastomeric material, such as a thermoplastic polyester elastomer and/or a thermoplastic polyether ester elastomer (HYTREL®, DuPont, Wilmington, Del.) and/or a thermoplastic polyurethane elastomer (PELLETHANE®, Dow Chemical, Midland, Mich.). Embodiments of the outer component 6122 are extruded, injection molded, compression molded, or over-molded. Some embodiments of extruded outer components 6122 have the ends produced thereby heat sealed together.

In the embodiment illustrated in FIG. 6A, the outer component 6122 of the outer ring comprises three lumens 6124—a first or middle lumen 6124a, a second or top lumen 6124b, and third or bottom lumen 6124c—extending circumferentially therethrough. In some embodiments, one or both of the top lumen 6124b and bottom lumen 6124c are optional. The middle lumen 6124a is disposed about at the center of the outer component 6122, substantially at the intersection of the major and minor axes of the oval cross section thereof. The top lumen 6124b is disposed substantially on the major axis, on a first side of the minor axis or above the middle lumen 6124a. The bottom lumen 6124c is disposed substantially on the major axis, on a second side of the minor axis or below the middle lumen 6124a. The middle lumen 6124a has an oval cross-section and is larger than the top lumen 6124b and the bottom lumen 6124c in the illustrated embodiment. The top lumen 6124b and bottom lumen 6124c each has a teardropped cross-section comprising a tapered portion disposed away from the middle lumen 6124a. In other embodiments, each of the lumens 6124 independently has another cross-sectional shape, for example, a generally circular cross section. In some embodiments, the cross-sectional shape of a lumen 6124 reduces contact between the lumen 6124 and an inner component (discussed below) disposed therein, thereby reducing friction and/or drag therebetween. For example, in some embodiments, the lumen 6124 has a polygonal cross section, for example, generally square, rectangular, diamond-shaped, hexagonal, star-shaped, or the like. In some embodiments, a wall of the lumen is textured, thereby reducing contact and friction with an inner component disposed therein.

Some embodiments of the outer component 6122 of the outer ring comprise a split member, such as a substantially straight member having a first end and a second end. The first and second ends of the member are brought proximate each other and coupled together, as will be discussed in more detail below.

Some embodiments of the inner component of the outer ring comprise a generally circular rigid wire 6126. In other embodiments, the rigid wire has another shape, for example, generally oval or elliptical. In the illustrated embodiment, the inner component is disposed in the middle lumen 6124b of the outer component 6122. The wire 6126 of the inner component is not compliant or resilient relative to the body tissue of the surgical incision or natural body orifice. Accordingly, the wire 6126 does not flex, yield, and/or deform relative to the body tissue of the surgical incision or natural body orifice during retraction of the incision or body orifice. In the illustrated embodiment, the rigid wire 6126 defines the peripheral shape or footprint, of the outer ring 6120 of the wound retractor. The rigid wire 6126 serves as an axle, annular axis, or center point for rotating the outer component 6122 of the outer ring during retraction, as discussed in greater detail below. The wire 6126 comprises a suitable material that is significantly harder than the outer component 6122 of the outer ring, for example full hard stainless steel. Some embodiments of the rigid wire of the inner component comprise a split wire 6126 having a first end and a second end. In some embodiments, the first and second ends of the rigid wire 6126 are coupled together using any suitable method, for example, by at least one of welding, using an adhesive, and/or using a mechanical fastener or coupler.

As indicated above, the inner component of the outer ring may comprise a generally circular rigid wire 6126. A diameter of the rigid wire 6126 is from between about 0.25 mm to about 12.7 mm (about 0.01 inch to about 0.5 inch). The diameter of the wire 6126 varies with the wound size and/or the size of the retractor 6100. For example, a larger wound size correlates with a larger wire diameter. In some embodiments, the wire diameter also correlates with the wire material. For example, increasing a hardness of the wire material permits reducing the wire diameter.

Some embodiments of the rigid wire 6126 for the inner component of the outer ring begin as a straight wire. The straight wire is inserted into the middle lumen 6124a of outer component. When the first and second ends of the outer component 6122 of the outer ring are joined, the wire assumes the desired shape, for example, a substantially circular shape or an oval shape, placing the wire 6126 in a preloaded condition under which the wire 6126 has a tendency to straighten. The tendency of the wire 6126 to straighten out helps the outer ring 6120 to maintain the desired shape, for example, circular or oval.

Some embodiments of the outer ring 6120 comprise a single, monolithic coupler 6128 that couples the first and second ends of the outer component 6122 of the outer ring together, and that couples the first and second ends of the wire 6126 of the inner component of the outer ring together. Embodiments of the single, monolithic coupler comprise a polymer, plastic, or other suitable material. In some embodiments, the monolithic coupler comprises of at least one of a thermoplastic elastomer (HYTREL®, DuPont; PELLETHANE®, Dow), acrylonitrile-butadiene-styrene (ABS), polyamide (NYLON®, DuPont), polyether block amide (PEBAX®, Arkema), and high density polyethylene (HDPE).

In some embodiments, the inner ring 6110 and the outer ring 6120 independently have different footprint shapes and/or footprint diameters. An inner ring 6110 with a larger diameter permits a greater retraction force, but is more difficult to insert and remove from a body cavity. An outer ring 6120 with a larger diameter is easier to roll or rotate when retracting, but couple with a larger cap, and consequently, may not be useable in space constrained procedures. Oval or elongated inner rings 6110 and outer rings 6120 reduce the force required to retract long, straight incisions compared with circular versions.

Some embodiments of the outer ring 6120 further comprise one or two split hoops disposed in one or both of the top lumen 6124*b* and the bottom lumen 6124*c*. Split hoops are discussed in greater detail below.

In some embodiments, the inner ring 6110 comprises a material that is softer than the material of the outer component 6122 of the outer ring. In other embodiments, the inner ring 6110 comprises a material of about the same hardness as the material of outer component 6122 of the outer ring, or harder than the material of the outer component 6122 of the outer ring.

Figure 7:
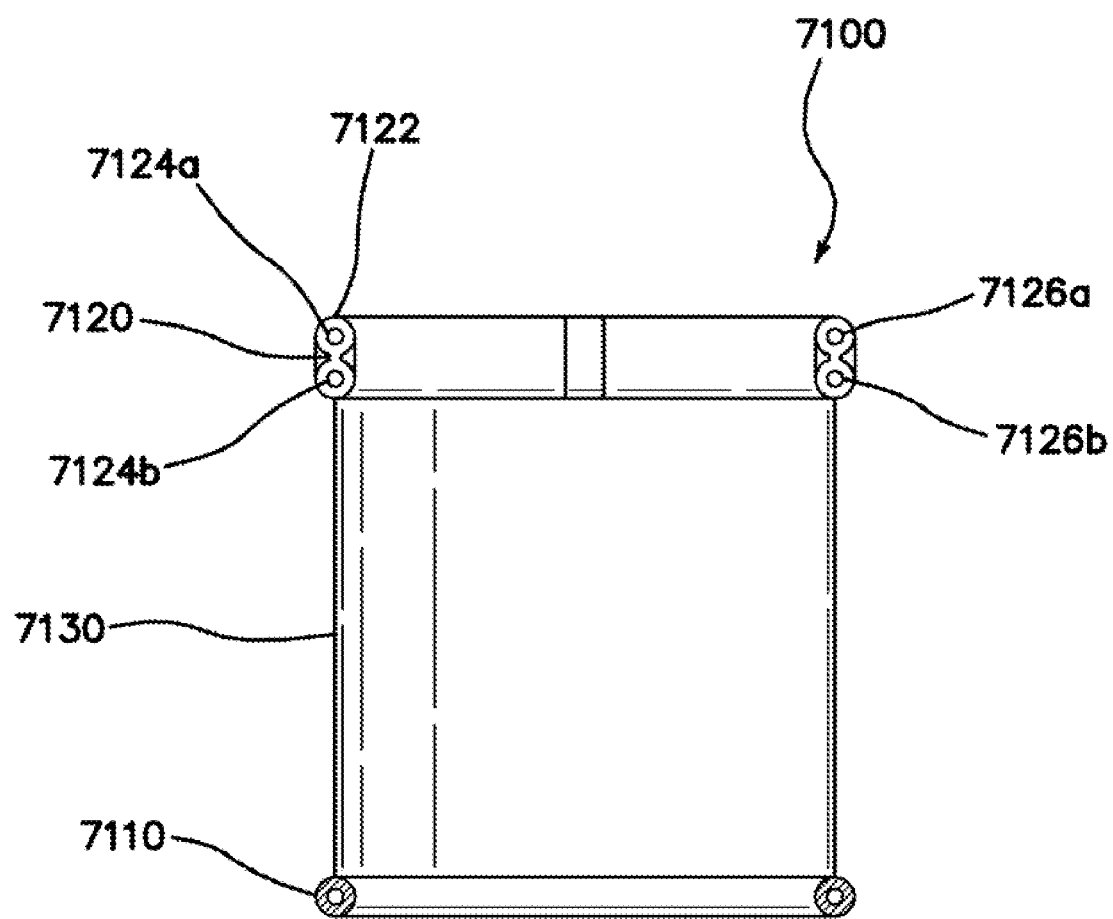
FIG. 7 is a partial side cross section of another embodiment of a retractor.

FIG. 7 illustrates a partial side cross section of another embodiment of a retractor 7100 generally similar to the embodiment 6100 described above. The retractor 7100 comprises an inner ring 7110, an outer ring 7120, and a sleeve 7130 extending between and coupling the inner ring 7110 and the outer ring 7120. In the illustrated embodiment, the outer ring 7120 of the wound retractor includes an outer component 7122 having a substantially oval cross-section including a first lumen 7124*a* and a second lumen 7124*b*. Each of the first 7124*a* and second 7124*b* lumens is positioned substantially along the major axis of the oval cross section with the first lumen 7124*a* positioned on a first side of the minor axis of the oval and the second lumen 7124*b* positioned on a second, opposite side of the minor axis of the oval. The inner component of the outer ring 7120 of the wound retractor includes a first split hoop 7126*a* disposed in the first lumen 7124*a* of the outer component of the outer ring, and a second split hoop 7126*b* disposed in the second lumen 7124*b* of the outer component. In some embodiments, each of the first 7126*a* and second 7126*b* split hoops independently comprises a hoop having a single split about its periphery with the split creating a first end of the split hoop and a second end of the split hoop. In its neutral position, the first and second ends of the respective split hoops substantially abut each other. In some embodiments, the split hoops 7126 are substantially noncompliant under the conditions in which the retractor 7100 is used, for example, as compared to tissues of a body wall under retraction, the outer component 7122 of the outer ring, and the sleeve 7120.

In some embodiments, properties of the retractor 7100 including the retraction force applied by the retractor 7100 and the ease of retracting an opening in a body wall depends at least in part on a spacing between the first 7124*a* and second 7124*b* lumens of the outer component of the outer ring, and a cross-sectional size or diameter of the first 7126*a* and second 7126*b* split hoops of the inner component of the outer ring. During use, the outer ring 7120 of the wound retractor is rolled down the sleeve 7130, thereby placing the split hoop 7126 proximal to the user under tension, opening the split hoop 7126 by creating a space between the first and second ends of the hoop 7124. In contrast, the rolling places the split hoop 7126 distal to the user under compression, forcing the first and second ends thereof together. In this manner, the rigid split hoop 7124 distal to the user serves as an axle or center of rotation for the outer ring 7120. Either or both increasing a distance between the two split hoops 7126 further apart, or increasing the strength of the split hoops 7126, increases the force used in rolling or rotating the outer ring 7120 of the wound retractor. Accordingly, the spacing or distance between the first 7124*a* and second 7124*b* lumens, and the cross-sectional sizes or diameters of the first 7126*a* and second 7126*b* split hoops are selected to balance the force for rotating the outer ring 7120 when retracting a body wall against the tendency of the outer ring to unroll 7120 under the force applied to the outer ring by the retracted body wall.

In some embodiments, the first 7126*a* and second 7126*b* split comprise a metal, for example, full-hard temper wire, stainless steel, piano wire heat treated to a spring temper, or any other suitable metal that produces a substantially noncompliant hoop. In some embodiments, the first 7126*a* and second 7126*b* split hoops comprise a rigid polymeric material fabricated by any suitable material, for example, by molding, machining, and/or and other suitable process known in the art. The substantially noncompliant split hoops 7126 may also comprise any other suitable rigid material known in the art.

In some embodiments, the cross-sectional diameters of the first 7126*a* and second 7126*b* split hoops vary with the cross-sectional dimensions of the outer component 7122 of the outer ring, and with the size and dimensions of the incision or body opening to be retracted. In some embodiments, a wire diameter of from about 2.5 mm to about 3.5 mm, for example, about 3 mm is used in retracting incisions of from about 5 cm to about 9 cm long. In some embodiments, each of the first 7126*a* and second 7126*b* hoops independently comprises a wire of from about 0.25 mm to about 6.35 mm (from about 0.01 inch to about 0.25 inch) in diameter.

The first 7126*a* and second 7126*b* split hoops of the inner component of the outer ring have smaller diameters in their relaxed states than the first lumen 7124*a* and the second lumen 7124*b* in which each is respectively disposed. Accordingly, when the outer ring 7120 is in a relaxed state, each of the split hoops 7126 is under tension, while the outer component 7122 is under compression. Consequently, in some embodiments, the split hoops 7126 hold the outer component 7122 of the outer ring in a closed configuration. In some embodiments, the compressive force of the first 7126*a* and second 7126*b* split hoops also control the orientation of the outer component 7122 in the relaxed state: that is, with the split hoops 7126 substantially one above the other, and/or with the major axis of the cross section of the outer component 7122 substantially parallel to a longitudinal axis of the outer component 7122.

In some embodiments, each split hoop 7126 is fabricated as a circle or other desired shape with the first and second end portions thereof overlapping each other. In some embodiments, dimensions of the first lumen and the second lumen 7124*b* and the composition of outer component 7122 of the outer ring constrain the first and second end portions of each split hoop from overlapping each other when the first split hoop 7126*a* and second split hoop 7126*b* are respectively disposed therein. In some embodiments, the lumens 7124 are dimensioned such that the first and second ends of each split hoop 7126 substantially abut each other when disposed therein. Other embodiments comprise a slight gap between the first and second ends of at least one split hoop 7126 disposed in the lumen 7124. The compressive spring force from the expanded split hoops urges the outer component 7122 to remain in a closed shape. Because the split hoops 7126 are disposed on either side of the minor axis of the cross section of the outer component 7122, the first 7126*a* and second 7126*b* split hoops urge and maintain the configuration of the outer ring 7120 such that the major axis of the cross section of the outer component 7122 remains vertical at 0° and 180° orientations, thereby facilitating the attachment of the cap to the outer ring 7120 of the wound retractor, as discussed below. In some embodiments, the outer ring 7120 is designed with an orientational bias other than vertical, for example, by changing at least one of the relative positions of the lumens 7124, the relative diameters of the lumens 7124, the relative relaxed diameters of the split hoops 7126, the relative cross-sectional diameters of the split hoops 7126, and the relative compositions of the split hoops 7126.

Because each of the first 7126a and second 7126b split hoops has substantially abutting first and second ends when the outer ring 7120 is in a relaxed configuration, each of the split hoops 7126 successively functions as an axle about which the outer component 7122 undergoes a half or 180° rotation in the retraction process. More particularly, as the outer ring 7120 is rolled, the first split hoop 7126a, which is initially above the second split hoop 7126b, is rolled or rotated around and outside the second split hoop 7126b, which serves as an axle or axis for the rotation, with the periphery of the first split hoop 7126a expanding to clear and pass around the second split hoop 7126b, resulting in the first split hoop 7126a below the second split hoop 7126b. On continued rolling of the outer ring 7120, the roles of the first 7126a and second 7126b split hoops are reversed, with the second split hoop 7126b rolling around and outside the first split hoop 7126a with the periphery of the second split hoop 7126b expanding to clear and pass around the first split hoop 7126a, which serves as an axle for the rotation. These steps are repeated until the incision or body opening is retracted to the desired degree.

In some embodiments, the outer ring 7120 of the wound retractor comprises an extruded elastomeric tube with a desired shape, for example, a generally circular or oval ring. In some embodiments, the first 7126a and second 7126b split hoops disposed in the first 7124a and second 7124b lumens of the outer component 7122, respectively, serves as a framework or scaffolding for the outer ring 7120, and consequently, determine the general shape thereof. In some embodiments, one of the first and second ends of the first split hoop 7126a is inserted into the first lumen 7124a of outer component, and one of the first and second ends of the second split hoop 7126b is inserted into the second lumen 7124b of the outer component. Each of the first 7126a and second 7126b split hoops is continually fed into its respective lumens 7124 until each of the split hoops 7126 is substantially entirely within its respective lumen 7124. The outer component 7122 generally assumes the shape of the split hoops 7126 positioned in the first 7124a and second 7124b lumens thereof. Some embodiments further comprise a coupler disposed between the first and second ends of the outer component 7122.

Referring again to the outer component 7122 of the outer ring, a ratio between a cross-sectional height and cross-sectional width thereof creates lock points as the outer component 7122 is rotated around the inner component. As the sleeve 7230 rolls-up around the outer ring 7120 when rotating the outer ring 7120, the lock points reduce or prevent the outer ring 7120 from rotating backwards, thus prevent the sleeve 7230 from unraveling or unrolling from the outer ring 7120. These lock points also provide incremental rotational positions for the outer ring 7120, thereby providing incremental retraction of the wound. Generally symmetrical cross-sectional shapes provide substantially uniform rotational motion and lock points, thereby providing a substantially uniform "snap" feel with each incremental rotation. The lock points also help keep the first, outer component of the second, outer ring from tilting as a result of forces encountered when retracting the surgical incision or body orifice. The illustrated embodiment comprises lock points where the cross-sectional major axis of the outer component 7120 is generally vertical, parallel to the longitudinal axis of the outer component 7120, or at 0° and 180°.

As stated above, embodiments of the outer component 7120 comprise a thermoplastic elastomeric material, such as HYTREL® (DuPont) or PELLETHANE® (Dow). Increasing the hardness of the material of the outer component 7122 increases the force used to rotate the outer ring 7120, as well as the resistance to unlock the outer ring 7120 from each lock point with each rotation of the outer ring 7120. Accordingly, the hardness of the material of the outer component 7122 in conjunction with the cross-sectional height and width of the outer component 7122 are selected to provide suitable or sufficient lock points for the outer ring 7120. For example, increasing the cross-sectional height-to-width ratio of the outer component 7122 permits reducing the material hardness while providing similar lock-point resistance or "snap". Conversely, increasing the material hardness permits reducing the cross-sectional height-to-width ratio of the outer component 7122.

Embodiments of the footprint of the outer ring 7120 are symmetrical or non-symmetrical and can vary in size and shape, such as a circle, ellipse, oval, or any other suitable shape, to conform to a body type, position, or size, thereby increasing or improving working space, or reducing potential interference with other instruments or ports during a laparoscopic procedure.

Reducing the cross-sectional profile or dimension of the outer ring 7120 of the wound retractor increases a range of insertion angles for instruments inserted therethrough. More particularly, one or both of the cross-sectional height and width of the outer ring 7120 may be reduced. The increased insertion-angle range is particularly useful for body orifice retraction, such as rectal or vaginal retraction. Reducing the cross-sectional profile of the outer ring 7120 increases the difficulty of rolling or rotating the outer component 7122 of the outer ring about the inner component of the outer ring 7120 during retraction. Accordingly, in some embodiments, a suitable tool used to facilitate rolling the outer component 7122 about the inner component.

Figure 4:
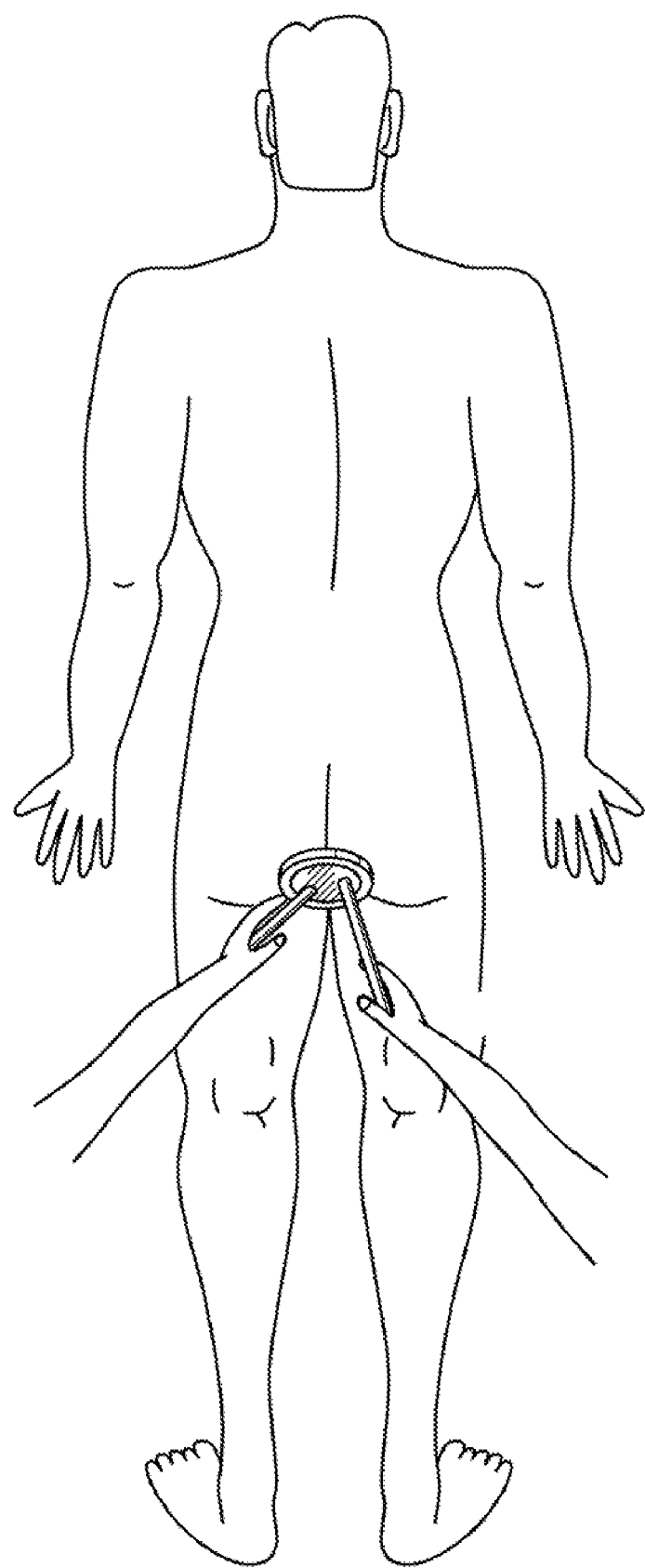
FIG. 4 is a top view illustrated a patient in the prone position with an embodiment of the access device deployed and in use at the anus of the patient.

An embodiment of a procedure for retracting an incision or body orifice is described with reference to the embodiment of the retractor 6100 illustrated in FIG. 6A, although the procedure is applicable to all of the embodiments of the retractor disclosed herein. In use, the surgical wound retractor 6100 is inserted into an incision, such as an incision made in an abdominal wall (FIG. 1), or a body orifice, such as the vagina (FIG. 2), mouth (FIG. 3) or anus (FIG. 4). The inner ring 6110 is folded or compressed into an oval or other suitable shape and urged through the incision or body orifice into an associated body cavity. Once the inner ring 6110 is fully disposed within the associated body cavity, it is allowed to resume its original, relaxed shape, for example, substantially circular, oval, or other original shape. The inner ring 6110 is then pulled upward against the inner surface of the body cavity, for example, by pulling the outer ring 6120 upward.

When the inner ring 6110 is fully in place, the outer ring 6120 is rotated rolled about its annular axis, which is defined by the inner component thereof. As discussed above, in the rolling procedure, the portion of the outer component 6122 distal from the user moves passes through the interior of the annular axis in moving towards the user, while the portion of the outer component 6122 proximal to the user passes around the exterior of the annular axis in moving away from the user. Rolling the outer ring 6120 rolls the sleeve 6130 around the outer ring 6120, reducing the distance between the inner ring 6110 and the outer ring 6120 and tensioning the sleeve 6130 therebetween, thereby retracting the incision or body orifice.

The outer ring 6120 is rolled until a desired state or degree of retraction is attained with the outer ring 6120, with a portion of the sleeve wrapped therearound, substantially in contact with the exterior surface of the body wall. When the outer ring 6120 and portion of the sleeve wrapped therearound is in contact with the exterior surface of the body wall, the outer ring 6120 of the retractor is sufficiently rigid to maintain the desired state or degree of retraction of the incision or body opening, for example, substantially fully retracted. Is some embodiments, the incision or body opening is not fully retracted, and is, instead, only partially retracted, which permits a degree of motion for the retractor 6100 associated cover 5500 (FIG. 5) relative to the incision or opening. Moreover, when the outer ring 6120 with a portion of the sleeve wrapped therearound is in contact with the exterior surface of the body wall, the outer ring 6120 of the wound retractor is noncompliant, that is, not flexible or likely to yield under the forces normally experienced during use of the wound retractor 6100. Accordingly, embodiments of the rigid outer ring 6120 facilitate 360° atraumatic retraction of an incision or body opening. The illustrated wound retractor 6100 is a durable device that provides reliable protection of the incision or body opening during surgery.

As illustrated in FIG. 5, some embodiments of the access device 5000 comprise a cap, cover, or lid 5500 coupled to the outer ring of the retractor 5100, which seals the retractor 5100, for example, for maintaining pneumoperitoneum. In some embodiments, lid 5500 is removable, for example to provide access into the body cavity. Some embodiments of the lid 5500 comprise a transparent or translucent portion, thereby allowing a user to view into the body cavity without removing the lid 5500. As will be described below, one embodiment of a lid 5500 is a gel cap. In some embodiments, a cross-sectional shape of the outer component 6112 (FIG. 6A) of the outer ring of the wound retractor is selected to reduce or prevent the lid 5500 from partial and/or incorrect coupling to the outer ring 6110 (FIG. 6A) of the wound retractor. Such cross-sectional shapes include oval and rectangular, or any other suitable cross-sectional shape that provides the desired functionality, for example, hexagonal, octagonal, and the like. Additionally, depending on the use and on surgeon preference, in some embodiments, each of the inner ring 6110 and outer ring 6120 of the wound retractor includes independently variable design configurations. For example, embodiments of the inner ring 6110 and/or the outer ring 6120 are rigid or flexible, and have footprints, cross-sectional shapes, and/or dimensions dependent on the intended use, for example, circular or oval footprints, diameters dependent on incision or orifice dimensions, or cross-sectional dimensions dependent on retraction force.

Accordingly, embodiments of the wound retractor 6100 enable a surgeon to quickly retract and protectively line a surgical incision or natural body orifice, while easily accommodating variations in the body wall thicknesses between patients. In addition, embodiments of the device 6100 effectively seal around the interior and exterior of the incision or orifice, and allow a sealing cap 5500 (FIG. 5) to be coupled thereto, thereby effectively sealing the body cavity and enabling a surgical procedure to be performed.

Figure 8A:
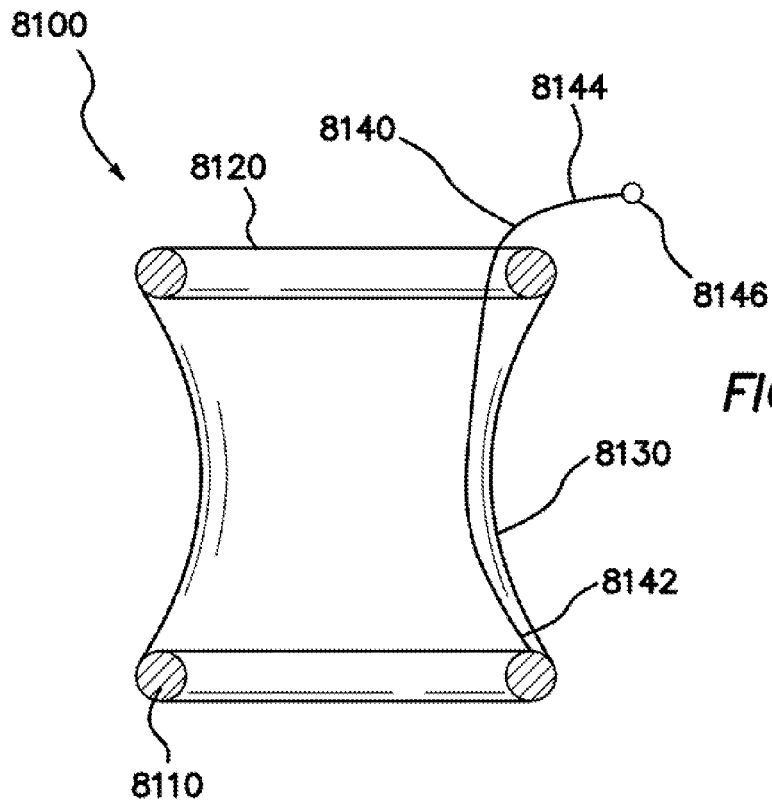
FIG. 8A is a side view of an embodiment of a retractor comprising a tether.
Figure 8B:
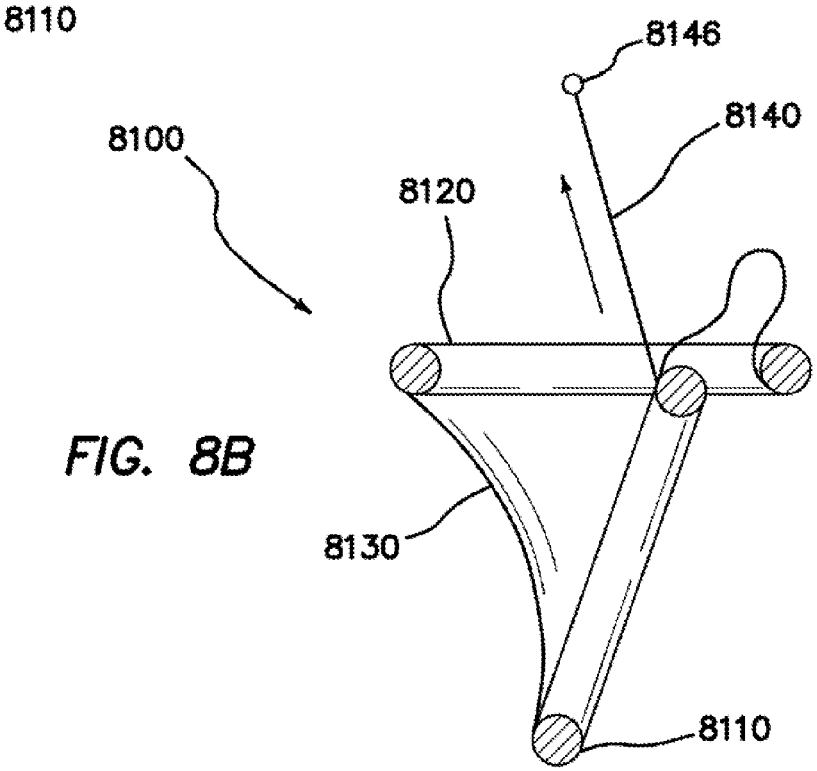
FIG. 8B is a side view of a method for removing the retractor illustrated in FIG. 8A.

FIG. 8A is a partial side cross-sectional view of another embodiment of a retractor 8100 comprising an inner ring 8110, an outer ring 8120, and a flexible sleeve 8130. A tether 8140 comprises a distal end 8142 secured to the inner ring 8110. A proximal end 8144 of the tether extends through the sleeve 8130 and the outer ring 8120, terminating in an optional handle 8146 in the illustrated embodiment. As illustrated in FIG. 8B, in an embodiment of a method for removing the retractor 8100 from a patient, pulling the handle 8146 of the tether draws the inner ring 8110 towards the outer ring 8120. Further pulling the tether 8140 causes the inner ring 8110 to contact the outer ring 8120, thereby deforming the inner ring 8110 as it passes through the outer ring 8120. Embodiments of tethers are also disclosed in U.S. Patent Publication No. 2006/0149137 A1, the disclosure of which is incorporated by reference.

In some embodiments, the tether comprises a fiber, a woven cord, or a braided cord. In some embodiments, the tether 8140 comprises a tube. In some embodiments, the tether 8140 comprises a cord and a tube, for example, disposed within the tube, integrated within a wall of the tube, or secured to an outer wall of the tube. The tether 8140 comprises any suitable material, for example, at least one of a suture material, polymer resin, polyamide (NYLON®, DACRON®), polyester, silk, polyethylene, polyether block amide (PEBAX®), and the like.

In some embodiments, the tether 8140 is releasably secured to an inner wall of the sleeve 8130 such that when the outer ring 8120 is rotated about its annular axis while retracting, the tether 8140 is released from an edge of the sleeve 8130 proximal to the outer ring 8120 as the sleeve 8130 winds therearound.

In some embodiments in which the tether 8140 comprises a tube, the tether further comprises at least one fluid opening through the wall of the tube disposed at or near the distal end 8142 thereof. In some of these embodiments, the tether 8140 is also useful as a gas inlet/outlet, for example, for an insufflation gas. In some procedures, the body wall creates a constriction in the sleeve 8130 when the retractor 8100 is in use. This constriction can restrict gas exchange and/or movement between a volume below the constriction and a volume above the constriction. In particular, the fluid opening at the distal end 8142 of the tether is below the constriction, while a fluid opening disposed at or near the outer ring 8120 or cap or cover 5500 (FIG. 5) is above the constriction. Positioning the fluid opening in the tether 8140 below the constriction facilitates gas injection into and/or venting from the volume below the constriction, and is particularly useful for venting vapors and/or smoke from the body cavity, which are generated, for example, in electrosurgical procedures such as cutting and cauterizing. In some embodiments, a fluid opening at the proximal end 8142 of the tubular tether extends through the gel cap and is fluidly connected to a gas source and/or vacuum source. In other embodiments, the fluid opening at the proximal end 8142 of the tether is fluidly coupled to another gas fitting, for example, disposed on the interior of the gel cap.

Figure 9A:
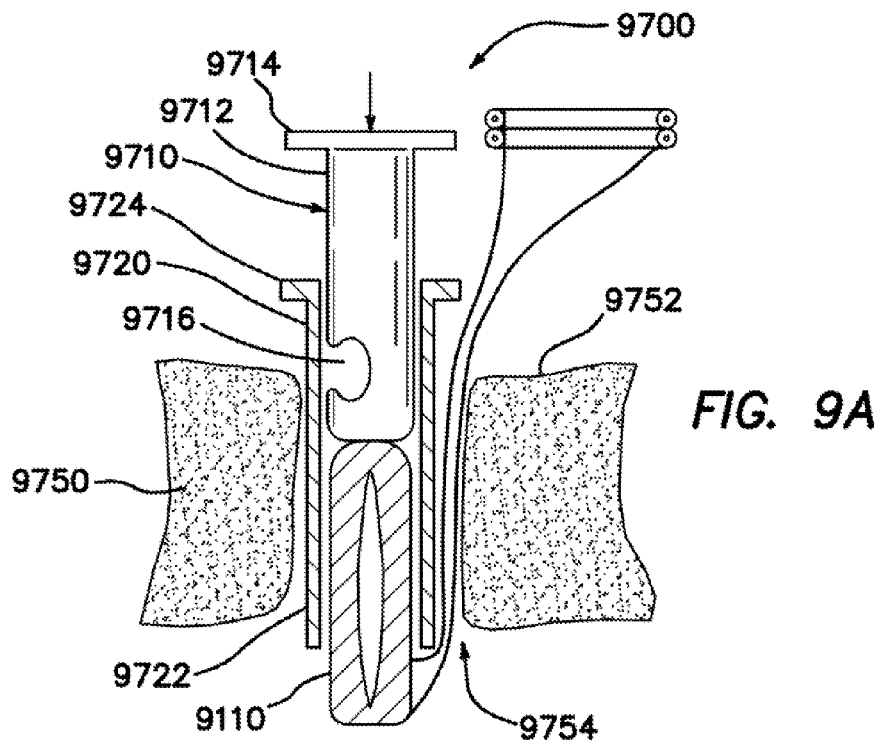
FIG. 9A is a side view of an embodiment of an insertion/removal device for a retractor and a method for inserting a retractor.

FIG. 9A is a side view of an embodiment of an insertion tool 9700 for inserting an inner ring 9110 of a retractor 9100. The insertion tool comprises an obturator 9710 and a cannula 9720. The obturator 9710 comprises an elongate, cylindrical body 9712 comprising a proximal end and a distal end, a handle 9714 at the proximal end of the body 9712, and a hook 9716 at the distal end of the body. The cannula 9720 comprises a tubular body 9722 comprising a proximal end and a distal end, and handle 9724 at the proximal end. The tubular body 9722 is open at both the proximal and distal ends, and is dimensioned to slidably receive the cylindrical body 9712 of the obturator therein. The tubular body 9722 is also dimensioned to receive at least a portion of the inner ring 9110 of a retractor. Other embodiments of insertion and extraction tools are described in U.S. Patent Publication No. 2006/0149137 A1, the disclosure of which is incorporated by reference.

As illustrated in FIG. 9A, the inner ring 9110 is loaded into the distal end of the tubular body 9722 of the cannula, which is then inserted through an opening or incision 9752 in a body wall 9750. The distal end of the obturator 9710 is inserted into and advanced through the proximal end of the tubular body 9722, thereby urging the inner ring 9110 out of the tubular body 9722 and into the body cavity 9754.

Figure 9B:
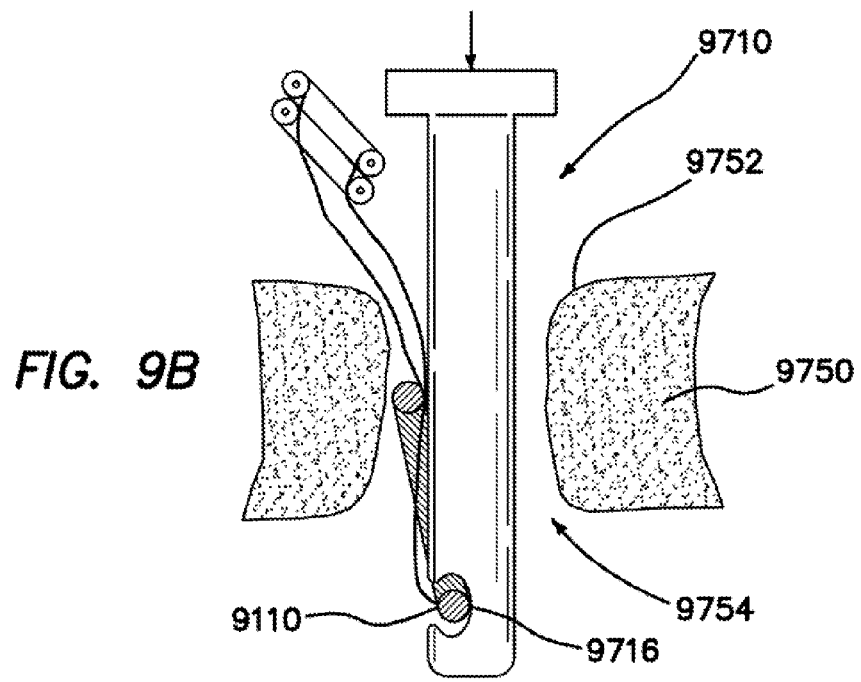
FIG. 9B is a side view of another embodiment of an insertion/removal device for a retractor and a method for inserting a retractor.

FIG. 9B illustrates another embodiment of a method for inserting an inner ring 9110 into a body cavity 9754 through an opening 9752 without using the cannula 9720. In this embodiment, a portion of the inner ring 9110 is captured in the hook 9716 disposed at the distal end of the obturator. The distal end of the obturator 9710 and the captured inner ring 9110 are urged through the opening 9752 and into the body cavity 9754.

Figure 9C:
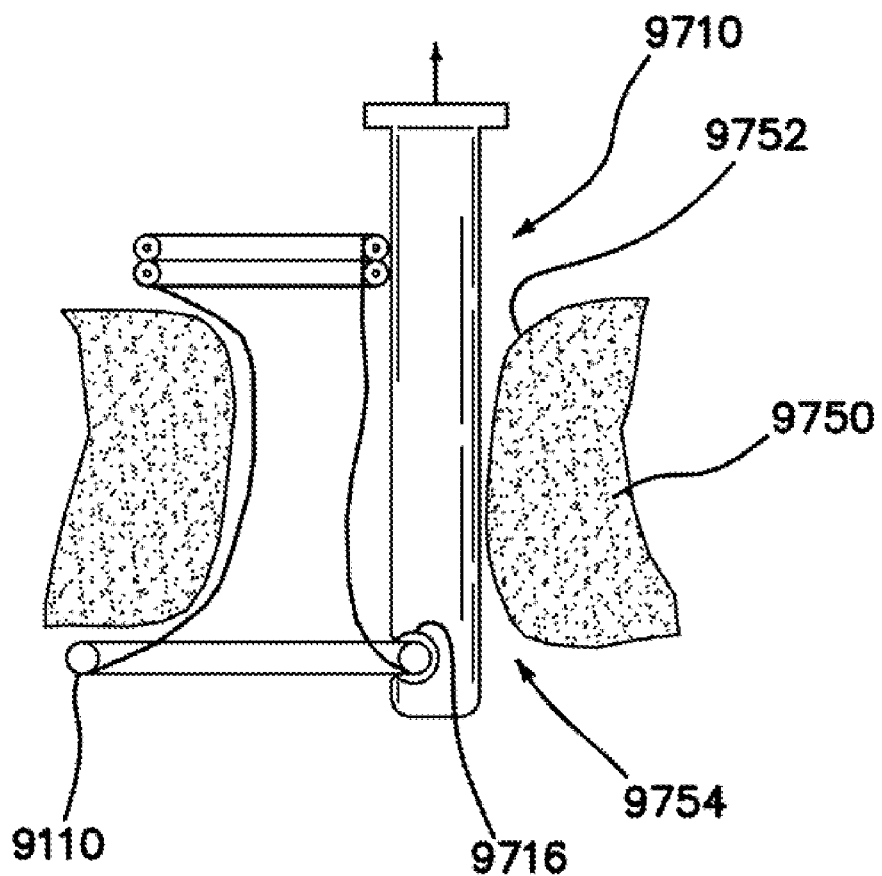
FIG. 9C is a side view of a method for removing a retractor using the device illustrated in FIG. 9B.

FIG. 9C illustrates an embodiment of a method for removing the inner ring 9110 using the hook 9716 of the obturator. The distal end of the obturator 9710 is inserted through the opening 9752 in the body wall between the sleeve 9130 and the body wall 9750. After capturing the inner ring 9110 with the hook 9716, the obturator 9710 and inner ring 9110 are withdrawn through the opening 9752.

FIG. 10A illustrates in perspective an embodiment of a cap or cover 10500, which is a surgical access device that seals the opening between the body cavity and the area outside the body cavity while providing access into the body cavity from outside the body cavity. More particularly, the illustrated cap 10500 releasably and sealingly couples to the outer ring 6120 (FIG. 6A) of the wound retractor. The cap 10500 comprises a cap ring 10510 dimensioned and configured for coupling to the outer ring 6120 of the wound retractor and a pad 10530 coupled to the cap ring 10510. Embodiments of the cap 10500 provide an artificial body wall with consistent properties compared with a natural body wall, for example, thickness, compliance, rigidity, uniformity, and the like.

The illustrated cap or cover 10500 is substantially circular. In other embodiment, the gel cap 10500 has another shape or footprint, for example, oval, elliptical, parabolic, square, rectangular, or another suitable curved or polygonal shape. In some embodiments, the outer ring 6120 of the retractor and cap ring 10510 of the cap have the same general shape or footprint. In other embodiments, the outer ring 6120 of the retractor and cap ring 10501 of the cap have substantially different shapes, for example, a generally circular outer ring 6120 and an oval cap ring 10510. In these embodiments, the outer ring 6120 is distorted or reshaped for coupling to the cap ring 10510, for example, by compressing opposed sides of the outer ring 6120. Non-circular shapes are useful, for example, for procedures in which space is limited. As discussed above, retracting a long, straight incision using an oval or elongated retractor requires less force than a similar procedure using a circular retractor.

In some embodiments, the pad 10530 comprises a gel. In such embodiments, the pad 10530 is referred to as a "gel pad" and the cap 10500 is referred to as a "gel cap". Descriptions of gel pads and gel caps generally apply to embodiments in which the pad 10530 does not comprise gel unless otherwise specified. In some embodiments, the gel pad 10530 does not comprise any preformed access channels therethrough, for example, for instrument access. Instruments may be inserted directly through the gel pad 10530, puncturing the gel pad 10530, and thereby creating access channels or portions in the gel pad 10530. Each access portion forms an instrument seal in the presence of an instrument inserted therethrough and a zero seal in the absence of an instrument inserted therethrough. The gel provides a gas tight seal around a variety of shapes and sizes of instruments inserted therethrough. Some embodiments of the gel pad 10530 also provide trocar access directly therethrough, which also provide instrument access into the body cavity. Embodiments of the gel pad 10530 have a working diameter of from about 40 mm to about 120 mm, which is the diameter of a portion of the gel pad 10530 through which instruments and/or trocars may be inserted. Embodiments of the gel cap 10500 are typically from about 10 mm to 50 mm wider than the working diameter.

Accordingly, embodiments of the gel cap 10500 maintain pneumoperitoneum during multiple instrument exchanges and substantially prevent unintentional loss of pneumoperitoneum. Embodiments of the gel cap 10500 also provide substantially continuous access and visibility during surgery. Embodiments of the gel cap 10500 have a small profile for use in procedures with limited surgical space.

In some embodiments, the gel is an ultragel, which is characterized by an ultimate elongation greater than about 1000 percent and a durometer less than about 5 Shore A. Some embodiments of the ultragel comprising KRATON® and mineral oil exhibit an ultimate elongation exceeding about 1500 percent and improved sealing properties, for example, sealing with instruments of a wider size range than other seal materials. In some embodiments, the seals comprising ultragels also form zero seals when the instrument is removed therefrom. Accordingly, in some embodiments of seals comprising ultragels, a single seal is acts as both the instrument seal as well as the zero seal.

Figure 10B:
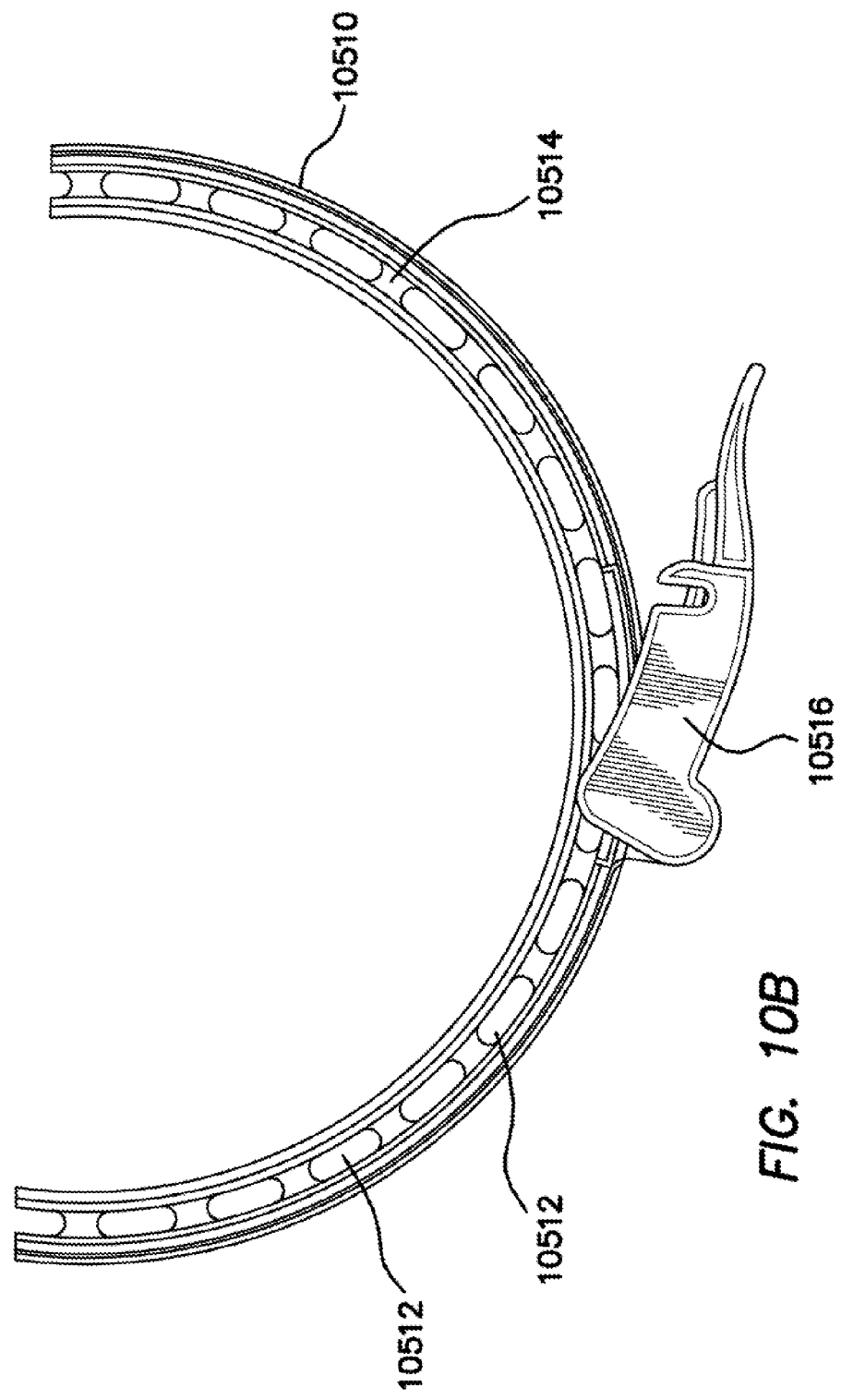
FIG. 10B is a bottom view of an embodiment of a cap ring.

Some embodiments of the cap ring 10510 comprise a substantially cylindrical ring comprising a proximal portion, a distal portion, and a longitudinal axis extending from the proximal portion to distal portions. In other embodiments, the cap ring 10510 has another shape or footprint, for example, oval. As best seen in FIG. 10B, which is a bottom view of a cap ring 10510, in the illustrated embodiment, the proximal portion of the cap ring 10510 comprises a plurality of apertures 10512 distributed about the periphery thereof. The apertures 10512 extend through a wall 10514 at the proximal portion of the cap ring. In other embodiments, the apertures 10512 are disposed in at least one member extending either longitudinally inward or longitudinally outward from the wall 10514 of the cap ring. The gel pad 10530 is disposed at the proximal portion of the cap ring 10510 in the illustrated embodiment, with portions of the gel pad 10530 extending through the apertures 10512, thereby creating an interlocking structure between the cap ring 10510 and the gel pad 10530, mechanically locking the cap ring 10510 and the gel pad 10530 together.

The distal portion of the cap ring 10510 is substantially cylindrical in the illustrated embodiment, and is dimensioned and configured to receive the outer ring 6120 (FIG. 6A) of the wound retractor. The cap ring 10510 comprises a latch mechanism 10516 that removably couples the cap ring 10510 to the outer ring 6120. Those skilled in the art will understand that other mechanisms are also useful for coupling the cap ring 10510 to the outer ring 6120 of the wound retractor, for example, protruding lips, levers, clips, latches, tongues, grooves, screw threads, bayonet mounts, screws, friction fittings, compression fitting, snap caps, and the like. In the illustrated embodiment, when the outer ring 6120 of the wound retractor is received in the distal portion of the cap ring 10510, the outer ring 6120 of the wound retractor contacts and embeds within a portion of the gel pad 10530 disposed at the distal portion of the cap ring 10510, thereby displacing a portion of the gel, and forming a seal between the gel pad 10530, and the outer ring 6120 and sleeve 6130 of the wound retractor. Thus, the distal portion of the gel pad 10530 is in juxtaposition with the incision or body orifice. In other embodiments, the cap ring 10510 is permanently coupled or fixed to the outer ring 6120.

The cap ring 10510 in some embodiments comprises a polymer. Examples of suitable polymers include, at least one of polyethylene (PE), low density polyethylene (LDPE), high density polyethylene (HDPE), ultra high molecular weight polyethylene (UHMWPE), polycarbonate, thermoplastic elastomers (DYNAFLEX®, GLS Corp.; KRATON®, Kraton Polymers), polyphenylene oxide (PPO), polystyrene, and the like. The polymer component of the cap ring is fabricated by any suitable method, including injection molding, melt casting, blow molding, and the like.

Some embodiments of a process in which the gel pad 10530 is cast in the cap ring 10510 are include steps performed at temperatures above about 130° C. over several hours, for example, from about three (3) to about four (4) hours. Accordingly, in some of these embodiments, the cap ring 10510 does not deform under these conditions.

Some embodiments of the gel pad 10530 comprise an elastomeric gel. Examples of such gels are described in U.S. patent application Ser. No. 10/381,220, filed Mar. 20, 2003, the disclosure of which is hereby incorporated by reference as if set forth in full herein. Embodiments of the gel are prepared by mixing at least one triblock copolymer with a solvent that dissolves the midblocks of the triblock copolymer. The mixture is typically a slurry. The endblocks typically comprise a thermoplastic material, such as styrene, while the midblocks typically comprise a thermoset elastomer such as, ethylene/butylene, isoprene, or butadiene. Examples of the triblock copolymer include styrene-ethylene/butylene-styrene (SEBS), styrene-isoprene-styrene (SIS), and styrene-butadiene-styrene (SBS). In some embodiments, the solvent is an oil, for example, mineral oil. Upon heating a mixture or slurry of the triblock copolymer, the midblocks dissolve in the mineral oil, thereby forming a network of the insoluble endblocks. The resulting network has enhanced elastomeric properties compared with the parent copolymer. In some embodiments, the triblock copolymer used is KRATON® G1651, which has a styrene to rubber ratio of 33/67. Once formed, the gel is substantially permanent and, by the nature of the endblocks, processable as a thermoplastic elastomer henceforward. The mixture or slurry has a minimum temperature at which it becomes a gel, which is referred to as the minimum gelling temperature (MGT). This temperature typically corresponds to the glass transition temperature of the thermoplastic endblock plus a few degrees. For example, the MGT for a mixture of KRATON® G1651 and mineral oil is about 120° C. When the slurry reaches the MGT and the transformation to a gel state takes place, the gel becomes more transparent, thereby providing a visual endpoint confirming the complete transformation of the slurry to the gel state, whereupon the gel may be cooled. Some embodiments of the gel comprise a diblock copolymer, either instead of or in addition to the triblock copolymer. Embodiments of the diblock copolymer comprise a thermoplastic first endblock, for example, styrene, and a thermoset elastomeric second endblock, for example, ethylene/butylene, isoprene, or butadiene. An example of a suitable diblock copolymer is styrene-ethylene/butylene (SEB).

For a given mass of slurry to form a complete gel, the entire mass of the slurry is heated to or above the MGT and held at or above the MGT for a sufficient time for the end blocks to form a network or matrix of interconnections. The slurry will continue to form a gel at temperatures between the MGT and temperatures at which the components of the slurry/gel begin to decompose and/or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel depends on the speed with which the entire mass of slurry reaches the MGT. Also, at temperatures higher than the MGT, the end block networks distribute and form more rapidly, thereby speeding the gel formation.

The various base gel formulas may also be mixed or alloyed with one another to provide gels with a variety of intermediate properties. For example, KRATON® G1701X is a mixture of seventy percent (70%) SEB and thirty percent (30%) SEBS, with an overall styrene to rubber ratio of 28/72. Those skilled in the art will appreciate that an almost unlimited number of combinations, alloys, and styrene to rubber ratios can be formulated, each providing and embodiment exhibiting one or more advantages, for example, low durometer, high elongation, and good tear strength.

Some embodiments of the gel material further comprise a polymer that, with a foaming agent, improves the sealing properties of the gel, for example, silicone, soft urethanes, and even harder plastics. Examples of suitable silicones include those used for electronic encapsulation. Examples of suitable harder plastics include polyvinylchloride (PVC), isoprene, KRATON® neat, and other KRATON®/oil mixtures. In the KRATON®/oil mixture, suitable oils include vegetable oils, petroleum oils, and silicone oils, as well as mineral oil.

Some embodiments of the gel comprise one or more additives that provide one or more desirable properties, for example, at least one of enhanced lubricity, improved appearance, and wound protection. Additives are incorporated directly into the gel and/or applied as a surface treatment. In some embodiments, other compounds are added to the gel to modify its physical properties and/or to assist in subsequent modification of the surface by providing bonding sites and/or surface charges. Additionally, oil-based colorants are added to the slurry to create gels of different colors in some embodiments.

Some embodiments of the gel pad 10530 comprise a layer of polyethylene on at least one surface. Polyethylene is dissolved in mineral oil and the solution applied to one or more surfaces of the gel pad 10530. The mineral oil does not evaporate, but instead, absorbs into the gel pad over time, leaving behind the polyethylene as a layer on the surface of the gel pad.

In some embodiments, the triblock copolymer/solvent mixture/slurry used to manufacture the gel pad 10530 comprises about ninety percent (90%) by weight of mineral oil and about ten percent (10%) by weight of KRATON® G1651. From a thermodynamic standpoint, this mixture behaves similarly to mineral oil. Because mineral oil has a relatively high heat capacity, transforming 0.45 kg (1 pound) of the slurry into a homogenous gel at about 130° C. may take from about three (3) to about four (4) hours. Once formed, the gel can be cooled as quickly as practicable with no apparent deleterious effects on the gel. In some embodiments, the gel is cooled by cold-water immersion. In other embodiments, the gel is air-cooled. Those skilled in the art will recognize that other cooling techniques are used in other embodiments.

Certain properties of the KRATON®/oil gel will vary with the weight ratio of the components. In general, a higher proportion of mineral oil results in a softer gel, while a higher proportion of KRATON® results in a firmer gel. A too-soft gel exhibits excessive tenting or doming of the gel cap 10500 during surgery when a patient's body cavity is insufflated. Some embodiments of gels that are too soft also do provide an adequate instrument seal and/or zero seal. The gel should be sufficiently soft to provide an adequate seal both in the presence of an instrument and in the absence of an instrument, however.

On prolonged or extended sitting or standing, the copolymer, such as KRATON®, and the solvent, such as mineral oil, in the slurry may separate. The slurry may be mixed to greater homogeneity, for example, with a high shear mixer. Mixing the slurry may introduce or add air to the slurry, however. To remove air from the slurry, the slurry may be degassed. In some embodiments, the slurry is degassed under a vacuum, for example, within a vacuum chamber. In some embodiments, the applied vacuum is about 0.79 meters (about 29.9 inches) of mercury, or about one (1) atmosphere. Optionally, stirring or mixing the slurry under vacuum facilitates removal of the air. During degassing under vacuum, the slurry typically expands, then bubbles, and then reduces in volume. The vacuum is typically discontinued when the bubbling substantially ceases. Degassing the slurry in a vacuum chamber reduces the volume of the slurry by about ten percent (10%). Degassing the slurry also reduces oxidation of the finished gel in some embodiments.

Degassing the slurry tends to result in a firmer gel. A gel made from a degassed slurry comprising about 91.6% by weight of mineral oil and about 8.4% by weight of KRATON® G1651, an eleven-to-one ratio, has about the same firmness as a gel made from a slurry that is not degassed and that comprises about ninety percent (90%) by weight of mineral oil and about ten percent (10%) by weight of KRATON® G1651, a nine-to-one ratio.

Because mineral oil typically has a lower density than KRATON®, the two components will separate after mixing, with the less dense mineral oil rising to the top of the container. This phase separation typically occurs when transforming a static slurry into a gel over several hours. Consequently, the resulting gel is non-homogeneous, with a higher concentration of mineral oil at the top and a lower concentration at the bottom. The speed of separation is a function of the depth or head height of the slurry being heated. Factors relevant to the relative homogeneity of the gel include the mass of slurry, the head height, the temperature at which the gel sets, and the speed at which the energy is transferred to the gel.

The gel pad 10530 or gel cap 10500 are gamma sterilized in some embodiments, which is relatively and/or comparatively simpler to qualify compared with other sterilization process, for example, versus ethylene oxide. Gamma sterilization can cause large bubbles to form in the gel pad, however, which are cosmetic and/or aesthetic issues in the sterilized devices. Because bubbles typically comprise greater than ninety-nine percent (99%) room air, the dissolved air is advantageously removed from the slurry prior to transforming the slurry into a gel. For example, the slurry may be degassed under vacuum, as described above, then gelled by heating. Some bubbles may still form in the gel during gamma sterilization, but typically disappear over a period of from about twenty-four (24) hours to about seventy-two (72) hours. Typically, mineral oil at room temperature has about ten percent (10%) dissolved gas. As discussed above, removing air from the gel makes the gel firmer. This effect is counterbalanced by a softening of the gel by the gamma radiation during gamma sterilization, however.

In some embodiments in which the gel pad 10530 is gamma sterilized, the gel comprises about ninety percent (90%) mineral oil by weight and about ten percent (10%) KRATON® by weight. As stated above, degassing the slurry makes the gel firmer. The counteracting softening by the gamma radiation, however, results in a gel with substantially the same firmness as a gel comprising about ninety percent (90%) mineral oil by weight and about ten percent (10%) KRATON® by weight that is not degassed and gamma sterilized.

In some embodiments, the gel pad 10530 is coupled to, attached to, formed with, or integrated with the cap ring 10510 to provide a gas-tight seal between the cap ring 10510 and the sleeve 6130 (FIG. 6A). The gel pad 10530 covers and seals the entire opening in the cap ring 10510, as well as covering substantially the entire wound or orifice opening. As stated above, the gel pad 10530 provides a gas tight seal around a variety of shapes and sizes of instruments inserted therethrough.

Embodiments in which a gel pad support structure of the cap ring 10510 comprises a thermoplastic elastomer, for example, DYNAFLEX® or KRATON®, and the gel pad 10530 comprises a similar thermoplastic elastomer, for example, KRATON®, exhibit improved adhesion between the gel pad 10530 and the cap ring 10510. The polystyrene component of KRATON® in the gel pad 10530 improves adhesion with polyphenylene oxide (PPO), polystyrene, and other similar polymers.

In some embodiments of cap rings 10510 comprising polycarbonate, the polycarbonate component of the cap ring 10510 does not bond with the gel pad 10530 at 130° C., which is a typical manufacturing temperature for a gel pad 10530 comprising KRATON®. Raising the temperature to about 150° C. for a few minutes during casting, however, bonds the gel pad 10530 to the cap ring 10510. It is believed that heating the gel pad 10530 and cap ring 10510 to a temperature at which both the polystyrene component of the gel and the polycarbonate are simultaneously above their melt points allows bonds to form therebetween. In other embodiments, the uncured gel and the cap ring 10510 are heated to near or at the glass transition temperature of the polycarbonate in the cap ring 10510, thereby bonding the gel pad 10530 to the cap ring 10510.

In some embodiments, the gel comprises mineral oil and the cap ring 10510 comprises a polymer that dissolves in mineral oil under the manufacturing conditions, for example, polyethylene (PE), low density polyethylene (LDPE), high density polyethylene (HDPE), and ultra high molecular weight polyethylene (UHMWPE). Using polyethylene (PE) as an example, PE has a higher molecular weight than mineral oil and dissolves in mineral oil at the temperatures used to cast the gel pad 10530. As such, as a portion of the PE in the cap ring 10510 dissolves in the mineral oil in the gel pad 10530 at the processing temperatures, for example, above about 130° C., a bond between the PE in the cap ring 10510 and gel pad 10530 is formed.

In an embodiment of a method for manufacturing a gel cap, the cap ring 10510 is placed into a mold that together with the cap ring 10510 includes a negative space in the desired shape of the gel pad and uncured gel is added to the mold. Sufficient uncured gel is then added to the mold to cover and fill the apertures 10512. The uncured gel flows through, fills, and remains within the apertures. Also, in some embodiments, the mold is filled with sufficient uncured gel to extend into the distal portion of the cap ring 10510. After the gel cures, the gel in the apertures connects and couples the gel on a first side of each aperture 10512 to the gel on a second side of the aperture, thereby mechanically locking the gel pad 10530 to the cap ring 10510.

Some embodiments include another method for coupling the gel pad 10530 to the cap ring 10510, either in addition to or instead of the mechanical interlocking discussed above. Such methods are useful, for example, for coupling separately formed gel pads or gel slugs 10530 and cap rings 10510. Some embodiments use a glue or adhesive to couple the gel pad 10530 to the cap ring 10510, for example, cyanoacrylate (SUPERGLUE® or KRAZY GLUE®). The glue is believed to bond to either the rubber or the styrene component of the triblock copolymer with a bond is frequently stronger than the gel material itself. Some embodiments use solvent welding in which a solvent dissolves a plastic in the cap ring 10510 and the polystyrene in the gel pad 10530. The solvent is applied to the gel pad 10530 and cap ring 10510 by any suitable method, for example, by spraying and/or by dipping. In effect, the solvent melts both the plastic of the cap ring 10510 as well as the polystyrene in the gel pad 10530, thereby forming a bond between the two, which remains after the solvent evaporates.

In an embodiment for manufacturing a gel cap 10500, the gel pad 10530 is cast into the cap ring 10510 to form the gel cap 10500. The cap ring 10510 is positioned in or placed into a mold cavity of a casting mold. Embodiments of the mold cavity include support for the annular walls of the cap ring 10510. Embodiments of the mold comprise a material with sufficient heat dissipation properties, for example, at least one of aluminum, copper, and brass. Those skilled in the art will recognize that other mold materials with lower heat dissipation properties will produce acceptable parts in some embodiments. Furthermore, some embodiments of the mold comprise active cooling elements, for examples, channels through which coolants are pumped.

The mold cavity and cap ring 10510 assembly is then filled with a desired amount of the triblock copolymer/mineral oil slurry such that the slurry contacts the cap ring 10510. In some embodiments, the slurry is preheated, for example, to about 52° C. (125° F.), which facilitates a complete filling of the mold cavity by the slurry, thereby reducing the probability of voids in the gel. Preheating the slurry to a temperature below the MGT reduces the viscosity of the slurry and allows the slurry to flow more easily. As stated above, some embodiments of the slurry are degassed in a vacuum before casting. In some embodiments, the slurry is also degassed after it is filled in the mold cavity to remove any air that may have been introduced during the filling of the mold cavity, as well as to facilitate flow of the slurry into voids in the mold. The mold, cap ring, and slurry are heated, for example, in an oven, until the slurry reaches a temperature of about 150° C. As stated above, the slurry turns into gel at about 120° C.; however, at about 150° C., the gel bonds to a polycarbonate cap ring 10510. Depending on the material used in the cap ring 10510, bonding may take place at a temperature other than about 150° C. In embodiments in which the cap ring 10510 is comprises a material with a lower melting point than the MGT, for example 120° C., the gel pad 10530 is molded separately as a gel slug, which is then bonded to the cap ring 10510 as discussed above.

When the transformation of the slurry into a gel is complete, for example, when the temperature of the gel pad reaches about 150° C., the gel cap 10500 is cooled, for example, by air-cooling, cold-water immersion, or another suitable method. At 150° C. the gel pad 10530 is soft and easily distorted. Distortions in the gel pad 10530 present during cooling would be set after cooling. Accordingly, in some embodiments, the gel cap 10500 is cooled within the mold, thereby reducing the likelihood of distorting the gel pad 10530. Factors affecting the cooling time include the size and configuration of the mold, the quantity of gel, temperature and quantity of cooling medium, the properties of the cooling medium, and the mold material. As an example, the cooling time for a particular gel cap 10500 may be about two (2) hours for air cooling and about fifteen (15) minutes for water cooling. Whether cooling with air or water, the final properties of the gel are substantially the same. The gel cap 10500 is typically cooled to about ambient room temperature, but may be cooled to a lower temperature if desired. At about 0° C., the gel hardens, which is useful, for example, in secondary operations such as when coupling separately manufactured gel pads 10530 and cap rings 10510. The gel cap 10500 may be removed from the mold at any time after the gel has set.

When removed from the mold, the gel pad 10530 typically has a tacky surface. Coating the gel pad 10530 with a powder, such as cornstarch, substantially reduces or eliminates the tackiness of the cured gel pad 10530.

As stated above, in some embodiments, the gel pad 10530 is molded separately from the cap ring 10510, and coupled to the cap ring 10510 in a secondary operation, for example, bonding. In some embodiments, the gel pad 10530 is molded as a gel slug with an outer perimeter smaller than the perimeter of the inner cylindrical wall of the cap ring 10510 and a height greater than the height of the cap ring 10510. Because the gel pad 10530 is molded separate from the cap ring 10510, the slurry need only be heated to the MGT, for example, about 120° C., to complete the transformation of the slurry into a gel, whereupon the gel becomes substantially transparent. As discussed above, the gel slug may be cooled, for example, to about 0° C., then placed within the inner cylindrical wall of the cap ring 10510.

In some embodiments, the gel slug is coupled to the cap ring 10510 through compression molding, in which the gel slug is compressed longitudinally, thereby expanding the outer perimeter of the gel slug and compressing the gel slug against the inner cylindrical wall of the cap ring 10510. The compressed gel slug and cap ring 10510 are then heated to a sufficient temperature for the polystyrene in the gel and the polymer of the cap ring 10510 to form bonds therebetween. Molding the gel slug separately from the cap ring 10510 followed by heat bonding the gel slug to the cap ring is especially useful in embodiments in which the cap ring 10510 comprises a material with a melting temperature lower than the MGT of the gel. In such situations, the gel slug can be molded separately and heat bonded to the cap ring 10510 without melting the cap ring 10510.

Some embodiments of the pad comprises another flexible, elastomeric material, either in place of or in addition to the gel, for example, at least one of rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (Neoprene®), perfluoroelastomer (Kalrez®), and the like. Some embodiments comprise a composite, for example, a multilayer structure and/or a plurality of sheets of one or more polymer materials. For example, some embodiments comprise outer surfaces and/or sheets providing desirable functionality, for example, mechanical strength, abrasion resistance, antimicrobial properties, and the like. Embodiments of the pad or artificial body wall permit translating and/or pivoting an instrument or trocar extending therethrough.

An embodiment of a method for retracting an incision or body orifice using the retractor 6100 is discussed in detail above. The method results in the outer ring 6120 of the retractor with a portion of the sleeve 6130 wrapped therearound substantially in contact with the exterior surface of the body wall. The gel cap 10510 is then coupled to the outer ring 6120 of the wound retractor, thereby sealing the opening between the body cavity and the area outside the body cavity and allowing the surgeon to insufflate the body cavity.

As discussed above, embodiments of the gel cap 10500 comprise no preformed access channels in the gel pad 10530. In use, instruments may be inserted directly through the gel pad 10530, thereby creating access channels through the gel pad 10530. Each access channel created in the gel cap forms an instrument seal in the presence of an instrument passing therethrough because the gel provides a gas tight seal around a variety of shapes and sizes of instruments. When the instrument is removed from the gel pad 10530, the channel created in the gel pad by the instrument closes to form a zero seal.

Some embodiments of the gel pad 10530, however, are damaged by repeated insertion and removal of instruments through an access channel, for example, exhibiting shredding, flaking, or the like. The damage can degrade the instrument seal or the zero seal of the affected access channel. Shreds or particles of the damaged gel can also fall into the body cavity. Accordingly, some embodiments use access devices such as trocars inserted through the gel pad 10530 for instrument access, in particular, where an access channel experiences repeated instrument manipulation, for example, insertion, removal, advancement, retraction, rotation and/or other manipulation. Each trocar inserted through the gel pad 10530 permits repeated introduction, removal, and/or manipulation of instruments therethrough without damaging the gel. Because the trocar itself is typically not extensively manipulated during a procedure, the access channel through which the trocar extends is not subject to damage, thereby maintaining the integrity of the gel pad 10530. Embodiments of the trocar are designed to withstand extensive instrument manipulation without failure under ordinary conditions.

Because the gel cap 10500 initially comprises no access channels, the surgeon is at liberty to determine the placement of instruments therethrough. Moreover, the surgeon has unlimited flexibility in the placement and repositioning of ports within the area of the gel cap 10500, as well as the option of selecting different trocar sizes for different clinical procedures. Being detachable, the gel cap 10500 allows for the removal of large specimens. Once removed, the gel cap 10500 can be re-coupled to the outer ring 6120 of the wound retractor, thereby restoring the seal and allow the surgeon to re-insufflate the body cavity.

Moreover, embodiments of the gel are deformable without losing physical integrity, and while maintaining substantially gas tight instrument seals with any instruments extending therethrough, as well as gas tight zero seals for any access channels without any instruments extending therethrough. Accordingly, embodiments of the gel cap 10500 permit both translational or positional, and angular or pivotal "float" or degrees of freedom for the instruments passing through the gel pad 10530. This float permits instrument motion both relative to the cap ring 10510 as well as relative to other instruments. In contrast, other single or limited port systems do not exhibit one or both translational or angular float for instruments.

Figure 11A:
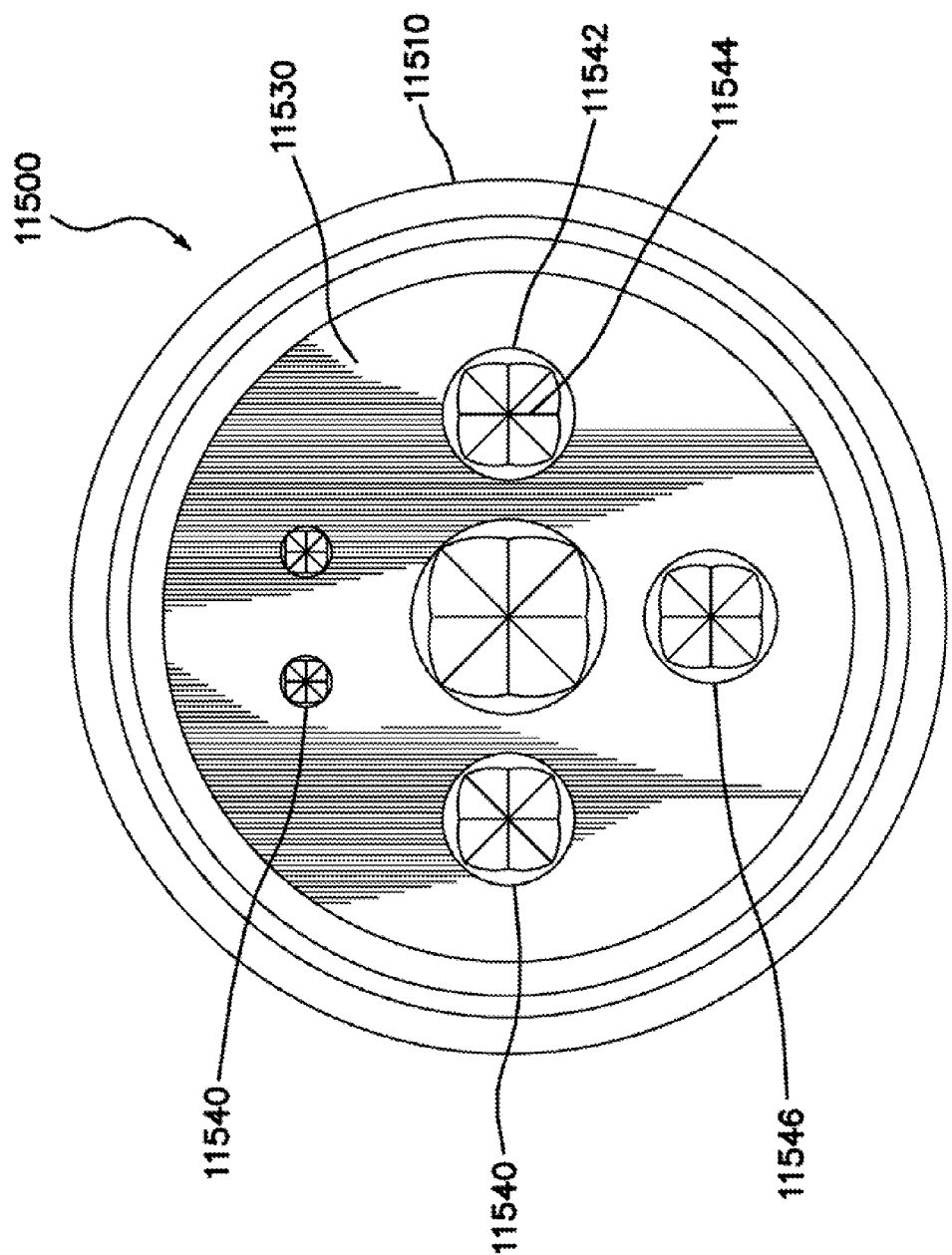
FIG. 11A is a top view of an embodiment of a gel cap comprising a plurality of access ports embedded in the gel pad.
Figure 11B:
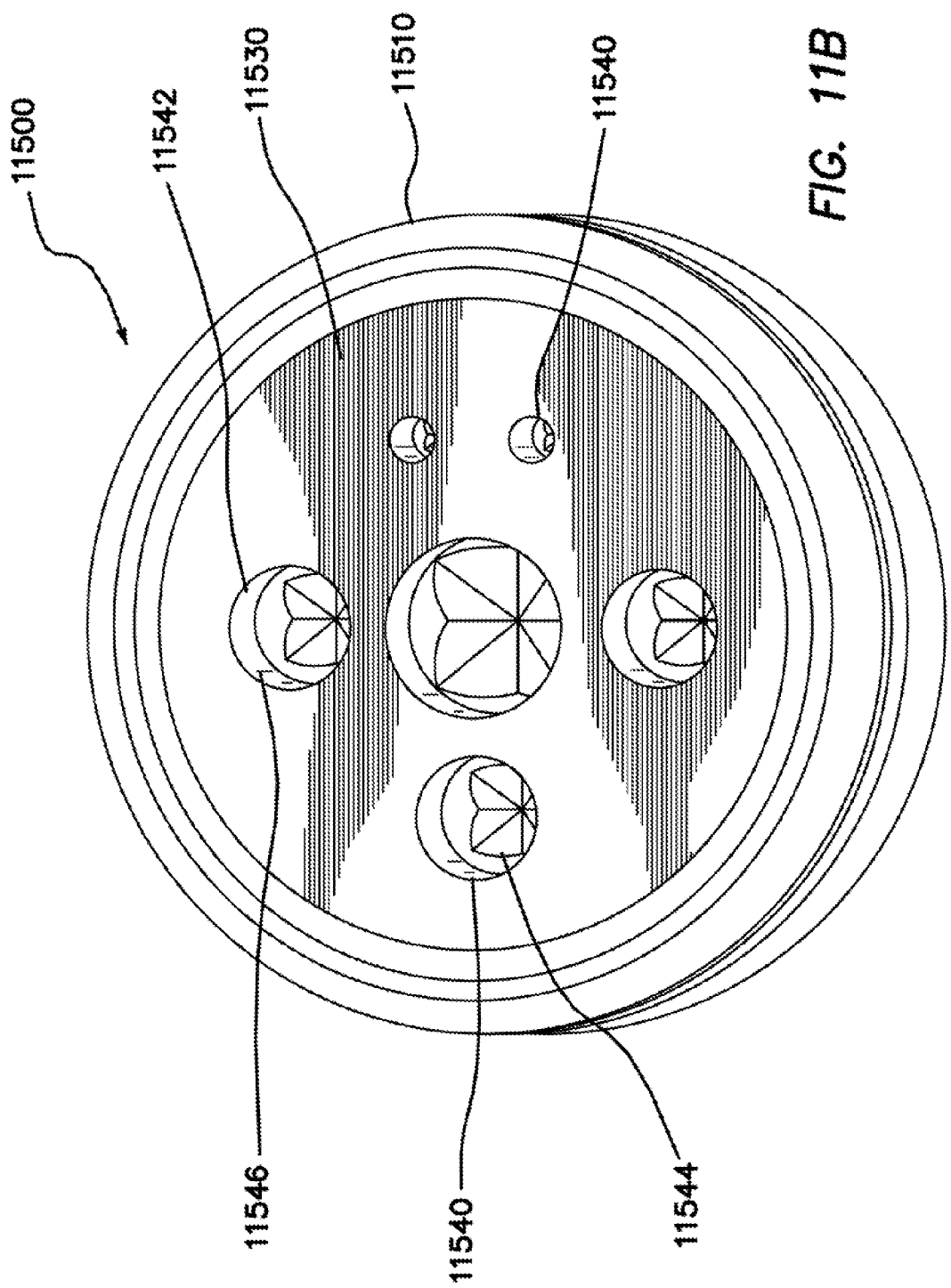
FIG. 11B is a top perspective view of the gel cap illustrated in FIG. 11A.

FIG. 11A is a top view of an embodiment of a gel cap 11500 comprising a plurality of access ports, seals, or sealing valves disposed in the gel pad. FIG. 11B is a perspective top view of the gel cap 11500 mounted on a retractor. FIG. 11C is a perspective bottom view of the gel cap 11500 mounted on a retractor. The gel cap 11500 comprises a cap ring 11510 and a gel pad 11530, which are generally similar to the cap ring and gel pad of the embodiment described above.

The gel cap 11500 further comprises a plurality of access ports 11540, at least a portion of which is disposed within or embedded within the gel pad 11530. In the illustrated embodiment, the access ports 11540 have a low profile, that is, do not protrude or protrude minimally above the proximal surface of the gel pad 11530 and/or below the distal surface of the gel pad 11530. Accordingly, the lengths of the access ports 11540 are similar to the thickness of the gel pad 11530, which is shorter than a length of a typical trocar inserted in the gel pad 11530, which comprises a seal assembly positioned above the gel pad 10530, and a cannula extending through the gel pad 11530. The reduced length of the access port 11540 allows increased angular or pivotal motion for instruments extending therethrough, and also permits the use of curved and/or angled instruments. In the illustrated embodiment, the access ports 11540 are substantially permanent or non-removable under the conditions under which the gel cap 11500 is used. Trocars can also be inserted through the gel pad 11530 if additional ports are desired.

Each port 11540 comprises longitudinal axis extending from a proximal side to a distal side of the gel pad 11530, a first seal 11542 disposed at the proximal side of the gel pad 11530, and a second seal 11544 disposed distal to the first seal 11542. A sight of each of the ports or seals 11540 has an aperture through the gel pad 11530 and coincides with the longitudinal axis. In the illustrated embodiment, the first seal 11542 forms an instrument seal with an instrument extending therethrough and the second seal 11544 forms a zero seal in the absence of an instrument extending therethrough.

In the illustrated embodiment, the first seal 11542 comprises a septum seal. Each septum seal comprises an aperture 11546 therethrough that is slightly smaller than a cross-section of the smallest instrument to be inserted therethrough. The aperture 11546 of the septum seal is substantially aligned with the aperture through the gel pad and the longitudinal axis of the port 11540. When an instrument is inserted through the aperture 11546 of the septum seal, the aperture 11546 expands and engages the outer surface of the instrument, thereby forming a seal therewith. The septum seal comprises an elastomeric material that biases the aperture against an instrument is inserted therethrough. Those skilled in the art will understand that other types of instrument seals are used in other embodiments.

In the illustrated embodiment, the second seal 11544 comprises a double-duckbill valve, which functions as a zero-closure seal that provides a zero seal in the absence of an instrument inserted therethrough. Those skilled in the art will understand that the second seal comprises another type of seal, for example, a duckbill valve, a flap valve, and the like. The double-duckbill valve comprises as elastomeric material. In some embodiments, each of the first seal 11542 and the second seal 11544 independently comprise an elastomeric material, for example, at least one of rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (Neoprene®), perfluoroelastomer (Kalrez®), and the like.

Figure 11D:
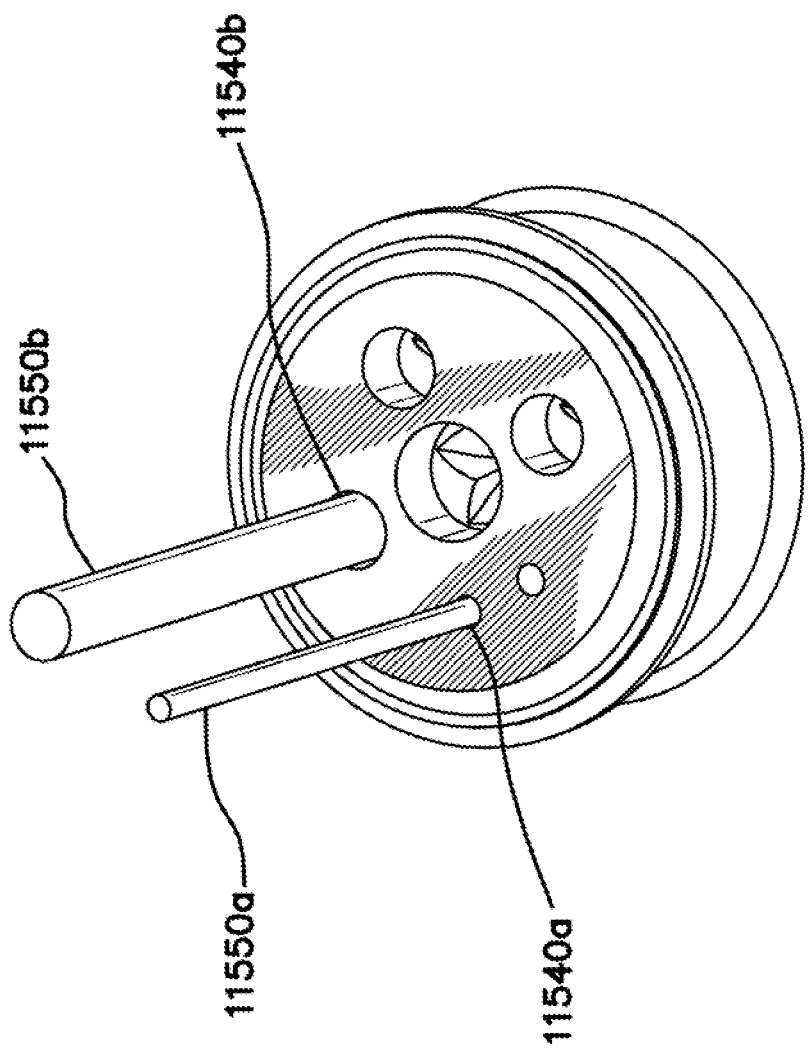
FIG. 11D is a top perspective view of the gel cap illustrated in FIG. 11A with instruments inserted through two of the access ports.
Figure 11E:
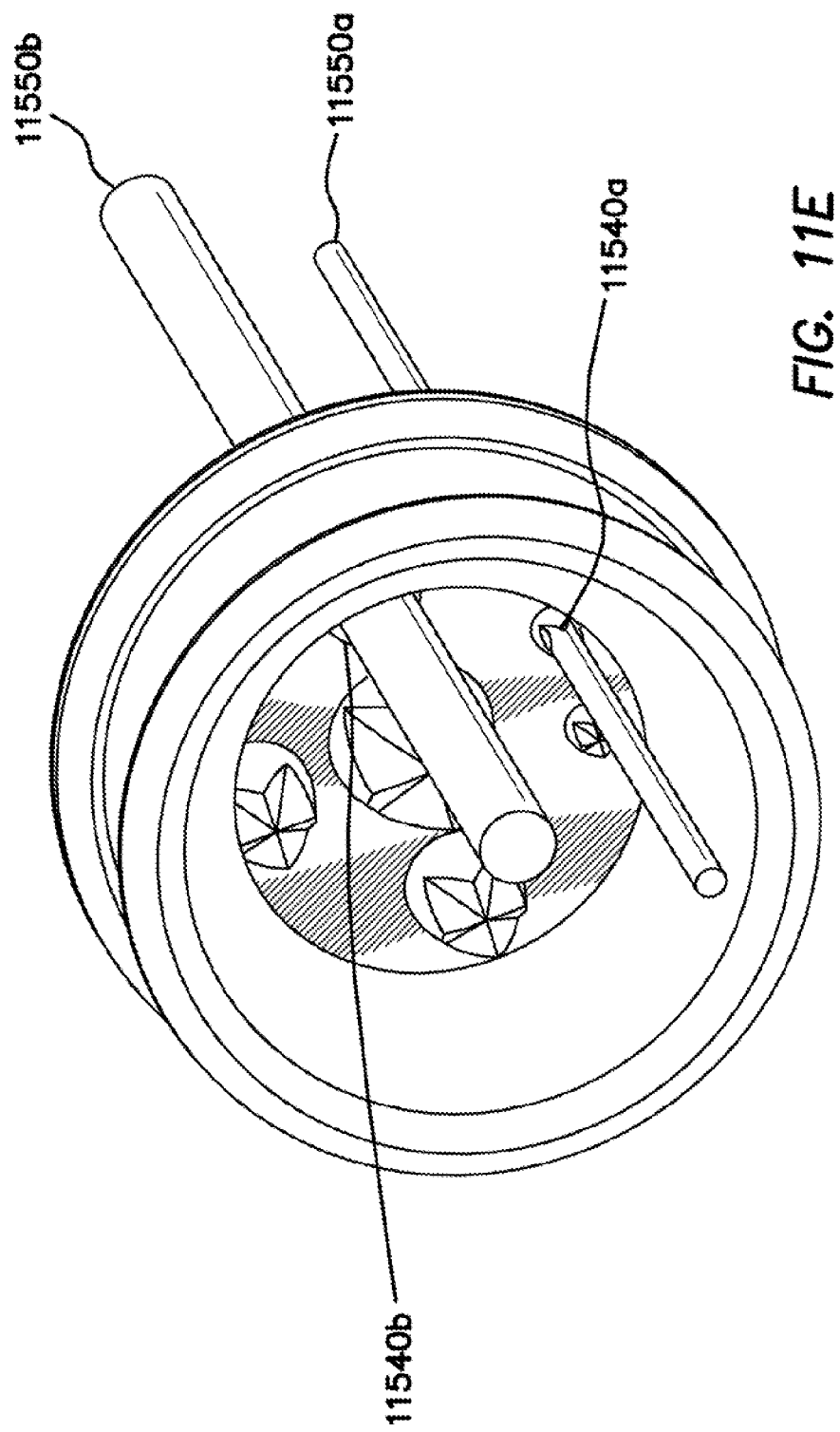
FIG. 11E is a bottom perspective view of the gel cap and instruments illustrated in FIG. 11D.
Figure 11F:
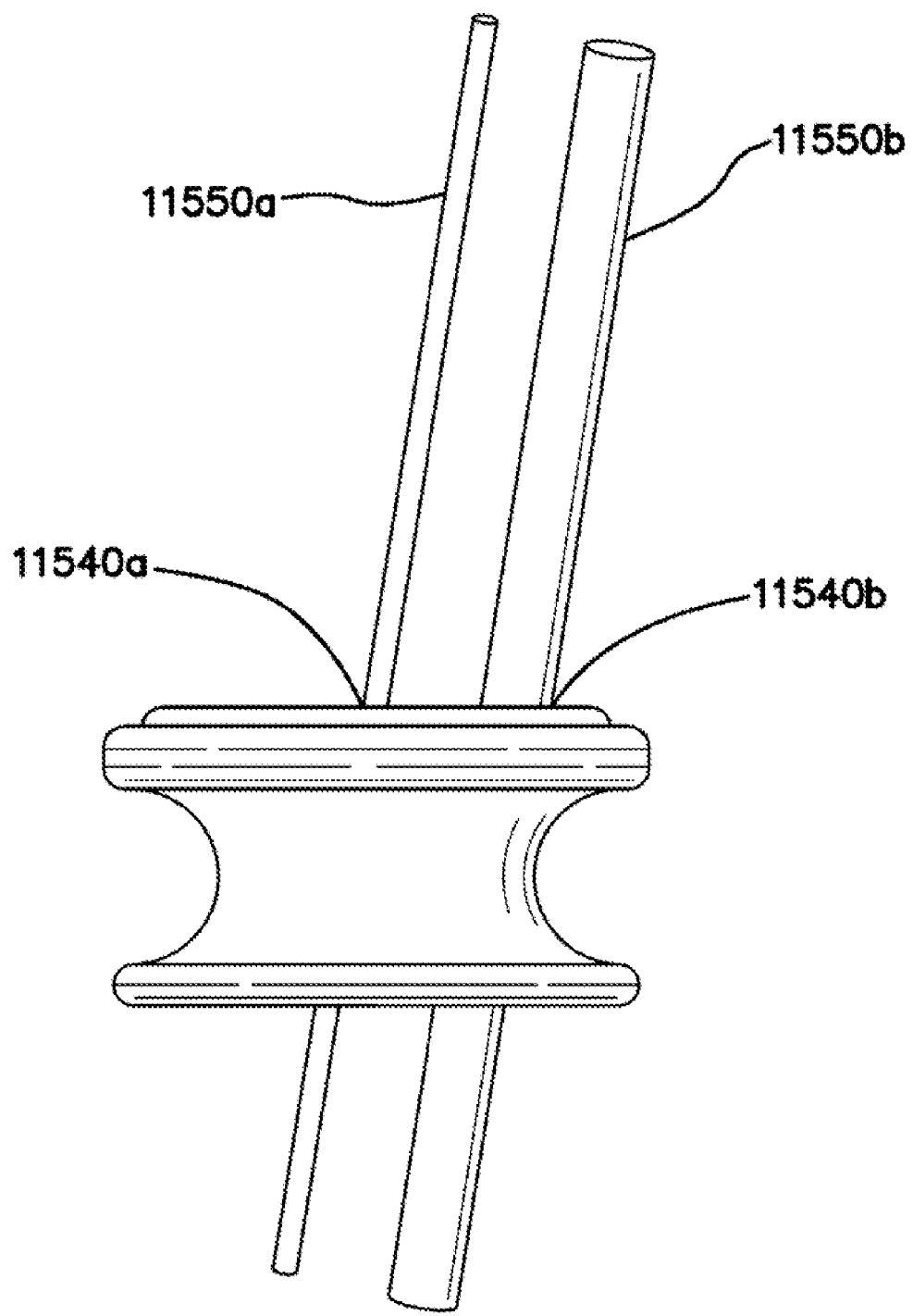
FIG. 11F is a side view of the gel cap and instruments illustrated in FIG. 11D.

Thus, during use, the septum seal provides an instrument seal in the presence of an instrument inserted therethrough, and the duckbill valve provides a zero seal in the absence of an instrument inserted therethrough. The illustrated embodiment comprises ports or seals 11540 in the gel pad of different sizes. Each size of port 11540 sealing accommodates a different range of instrument sizes inserted therethrough. The size of a port is typically given as the diameter of the largest instrument that the port will accommodate, for example, 5 mm, 11 mm, or 12 mm. FIGS. 11D, 11E, and 11F are a perspective top view, a perspective bottom view, and a side view of a thinner instrument 11550*a* and a thicker instrument 11550*b* inserted through a smaller port 11540*a* and a larger port 11540*b*, respectively, of the embodiment of the gel cap 11500 illustrated in FIGS. 11A-11C.

Figure 11G:
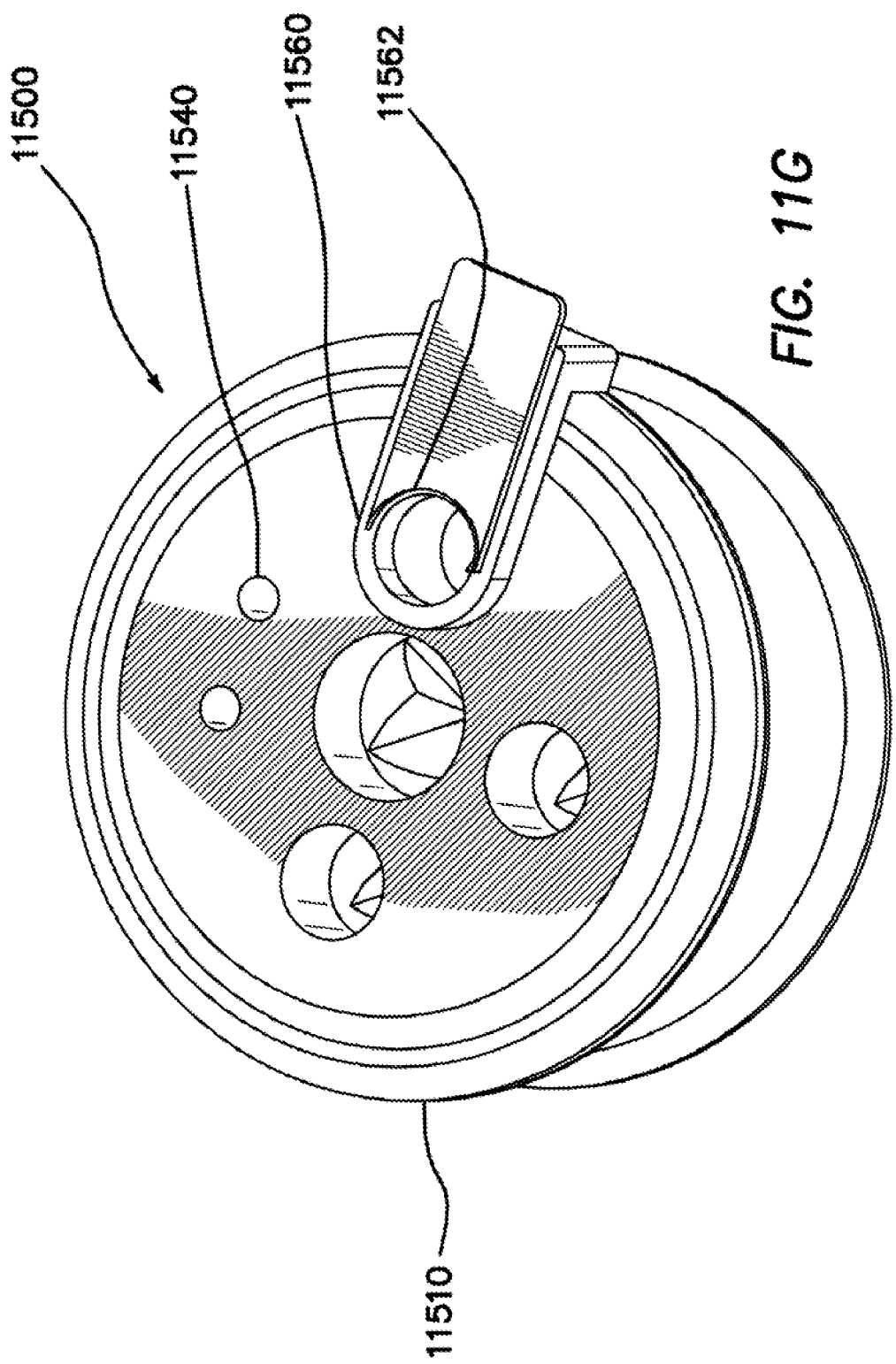
FIG. 11G is a top perspective view of an embodiment of gel cap comprising a fixed camera or laparoscope port.

FIG. 11G is a top perspective view of an embodiment of a gel cap 11500 further comprising a fixed port position, for example, for a camera or a laparoscope. The fixed port 11560 comprises a lock mechanism 11562 that maintaining the position of a camera or laparoscope inserted therethrough. In some embodiments, one of the ports 11540 further comprises a stopcock and/or gas fitting used as a gas inlet and/or outlet port for insufflating, depressurizing, and/or venting the body cavity of gas. In some embodiments, a gas inlet/outlet port is disposed on the cap ring 11510.

Figure 12:
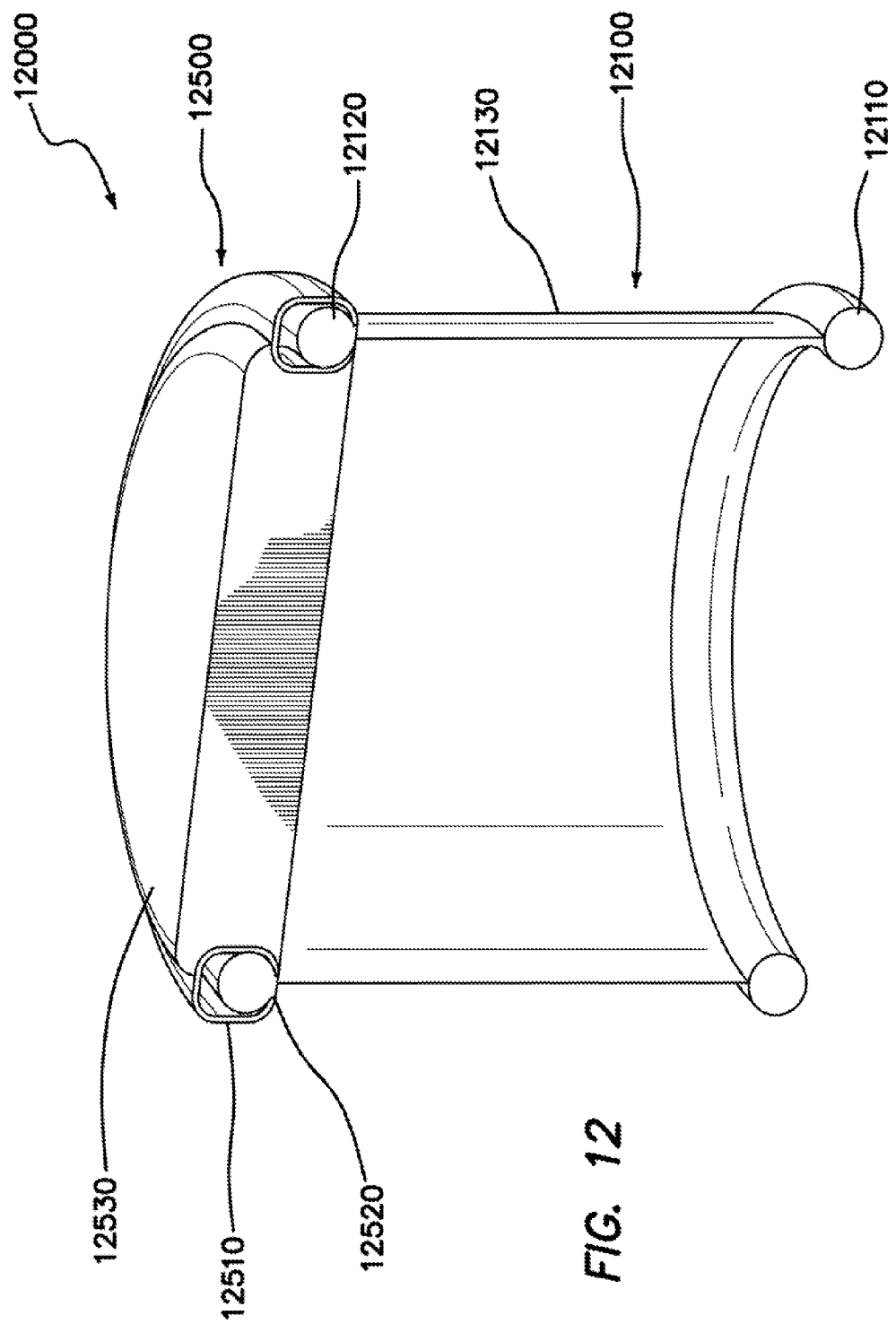
FIG. 12 is a cutaway perspective view of an embodiment of an access device system comprising a gel cap that snap fits to a retractor.

FIG. 12 is a cutaway perspective view of an embodiment of an access device system 12000 comprising retractor 12100 and a cap or cover 12500, which are similar to embodiments of retractors and gel caps described above. The retractor 12100 comprises an inner ring 12110, an outer ring 12120, and a sleeve 12130 extending between the inner ring 12110 and the outer ring 12120. In the illustrated embodiment, the cap 12500 is a gel cap comprising a proximal side, a distal side, a cap ring 12510, and a gel pad 12530. In the illustrated embodiment, the cap ring 12510 comprises a tubular ring dimensioned to receive the outer ring 12120 of the retractor therewithin. The distal side of the cap ring 12510 comprises an annular slot 12520, which is sufficiently radially deformable for the outer ring 12120 to reversibly pass therethrough. Accordingly, the illustrated embodiment of the cap ring 12510 secures the cap 12500 to the outer ring 12120 with a snap or friction fit.

Figure 13:
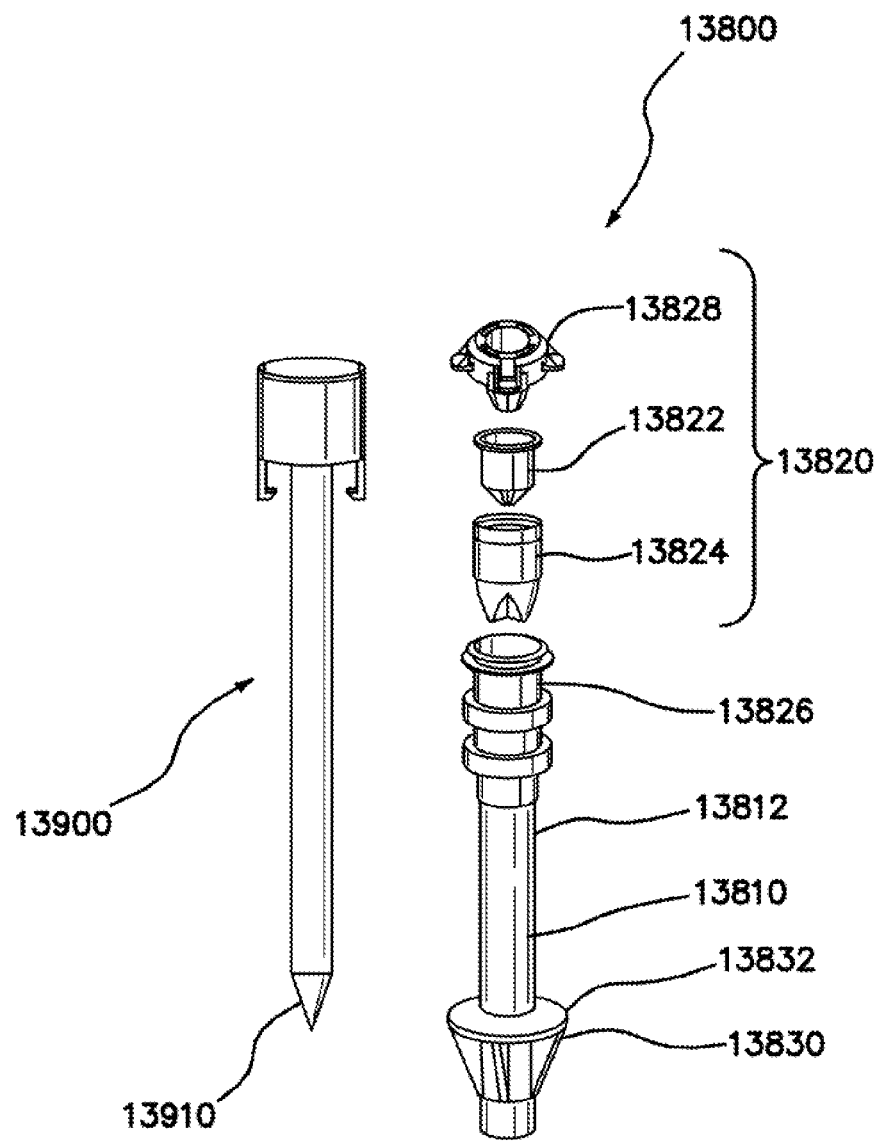
FIG. 13 is an exploded view of an embodiment of a trocar.

FIG. 13 is an exploded view of an embodiment of a trocar 13800 and optional obturator 13900, which is a component of some embodiments of the access device system. In the illustrated embodiment, the obturator 13900 comprises a pointed, puncture tip 13910. In embodiments in which the trocar 13800 and obturator 13900 are inserted through a gel pad 10530 rather than a body wall, potential damage to underlying tissue by contact with the tip 13910 is reduced because the gel pad 10530 serves as an artificial body wall that is spaced from the underlying tissue as discussed above. In other embodiments, the obturator tip 13910 has another shape, for example, blunt and/or bladeless, which, for example, reduces the likelihood of damage to other components of the access system, for example, a retraction sheath of a retractor.

The trocar 13800 comprises a proximal end, a distal end, and a longitudinal axis. The trocar 13800 comprises a cannula 13810 extending along the longitudinal axis. A trocar seal 13820 is disposed at the proximal end of the cannula 13810. A retainer 13830 is disposed at the distal end or tip of the cannula 13810. In the illustrated embodiment, the distal end or tip of the cannula 13810 is not angled. Other embodiments comprise an angled distal end or tip of the cannula 13810. The illustrated embodiment of the trocar 13800 does not comprise an insufflation gas inlet. Consequently, the trocar 13800 is typically used in procedures in which a body cavity is not insufflated, or in which insufflation is provided through another device. Other embodiments of trocars are disclosed in U.S. patent application Ser. No. 11/677,994, filed Feb. 22, 2007, the disclosure of which is incorporated by reference.

The cannula 13810 comprises an elongate, tubular cannula body 13812 dimensioned to accommodate an instrument or instruments received therethrough. In the illustrated embodiment, the cannula body 13812 is a substantially cylindrical tube, and extends through the gel pad 10530 in use. In the illustrated embodiment, the cannula body 13812 extends from the proximal end of the cannula 13810 to which the trocar seal 13820 is coupled, and which has a larger outer diameter than the cannula body 13812.

In some embodiments, the cannula 13810 is comparatively short because the cannula body 13812 need only traverse the gel pad 10530 (FIG. 10A), which has a known and consistent thickness, rather than a body wall. Accordingly, some embodiments of the cannula body 13812 are not more than about 2-times longer, about 1.5-times longer, about 1.2-times longer, or about 1.1-times longer than the thickness of the gel pad. In some embodiments, the cannula body 13812 is less than about 20 mm, about 10 mm, or about 5 mm longer than the thickness of the gel pad. In some embodiments, the cannula body 13812 is about as long as the gel pad is thick. In other embodiments, the cannula body 13812 has a different length, for example, a length typical for a cannula used for traversing a body wall. Shorter length cannula bodies permit increased angular degrees of freedom for instruments passing therethrough. Embodiments of shorter cannula bodies also accommodate curved instruments. The cannula 13810 comprises any suitable biocompatible material. In some embodiments, the cannula 13810 comprises a flexible material.

The illustrated trocar seal 13820 comprises an instrument or septum seal 13822 and a zero seal 13824. The instrument seal 13822 seals instruments passing therethrough, thereby maintaining pneumoperitoneum. The zero seal 13824 provides a seal when no instrument passes through the trocar seal 13820. The instrument seal 13822 and zero seal 13824 are received in a housing 13826 disposed at the proximal end of the cannula 13810 and secured therein by a seal cover 13828.

The retainer 13830 is disposed at or near the distal end of the cannula 13810. In the illustrated embodiment, the distal end of the cannula 13810 is generally perpendicular to the longitudinal axis thereof, or not angled. Other embodiments comprise an angled distal end or tip. In some embodiments, the retainer 13830 and cannula 13810 are integrated, while in other embodiments, the retainer 13830 and cannula 13810 are not integrated. In the illustrated embodiment, the proximal end of the retainer 13830 comprises a flange 13832 that is generally flat and perpendicular to the longitudinal axis, while the distal end is tapered, narrowing toward the distal end of the cannula 13810. The flange 13832 reduces the likelihood of accidental or inadvertent removal of the trocar 13800 from the gel pad. Some embodiments of the proximal face of the flange 13832 comprise additional anchoring features, for example, at least one of barbs, spikes, ridges, texturing, and the like, which are configured to penetrate or bite into a distal face of the gel pad 10530. In some embodiments, a diameter of the flange 13832 is from about 1.5 to about 2.5 times wider, or from about 2 to about 2.2 times wider than an outer diameter of the cannula body 13812. Some embodiments of the trocar 13800 are 5-mm trocars, in which the outer diameter of the cannula body 13812 is from about 7 mm to about 8 mm.

The tapered end of the retainer 13830 facilitates insertion of the trocar 13800 through the gel pad, either by itself, or when assembled with the obturator 13900 extending therethrough. For example, in some embodiments, the retainer 13830 is inserted through a preformed opening in the gel pad 10530. Because embodiments of the gel material of the gel pad 10530 have high elongation values, as discussed above, the retainer 13830 is insertable through a relatively small opening in the gel pad 10530, yet resists inadvertent removal, as discussed above.

In some embodiments in which the retainer 13830 and cannula 13810 are not integrated, that is, are separate components, the retainer 13830 is secured to the cannula 13810 after the cannula 13810 is inserted through the gel pad. In some embodiments, the cannula 13810 and retainer 13830 are secured mechanically, for example, using latches, screw threads, clips, lock rings, ratchets, and the like. In some embodiments, the cannula 13810 and retainer 13830 are secured adhesively. In some embodiments, the position of the retainer 13830 is adjustable, for example, to accommodate gel pads of different thicknesses. In some embodiments, the cannula 13810 and/or retainer 13830 is secured to the gel pad, for example, adhesively.

Figure 14A:
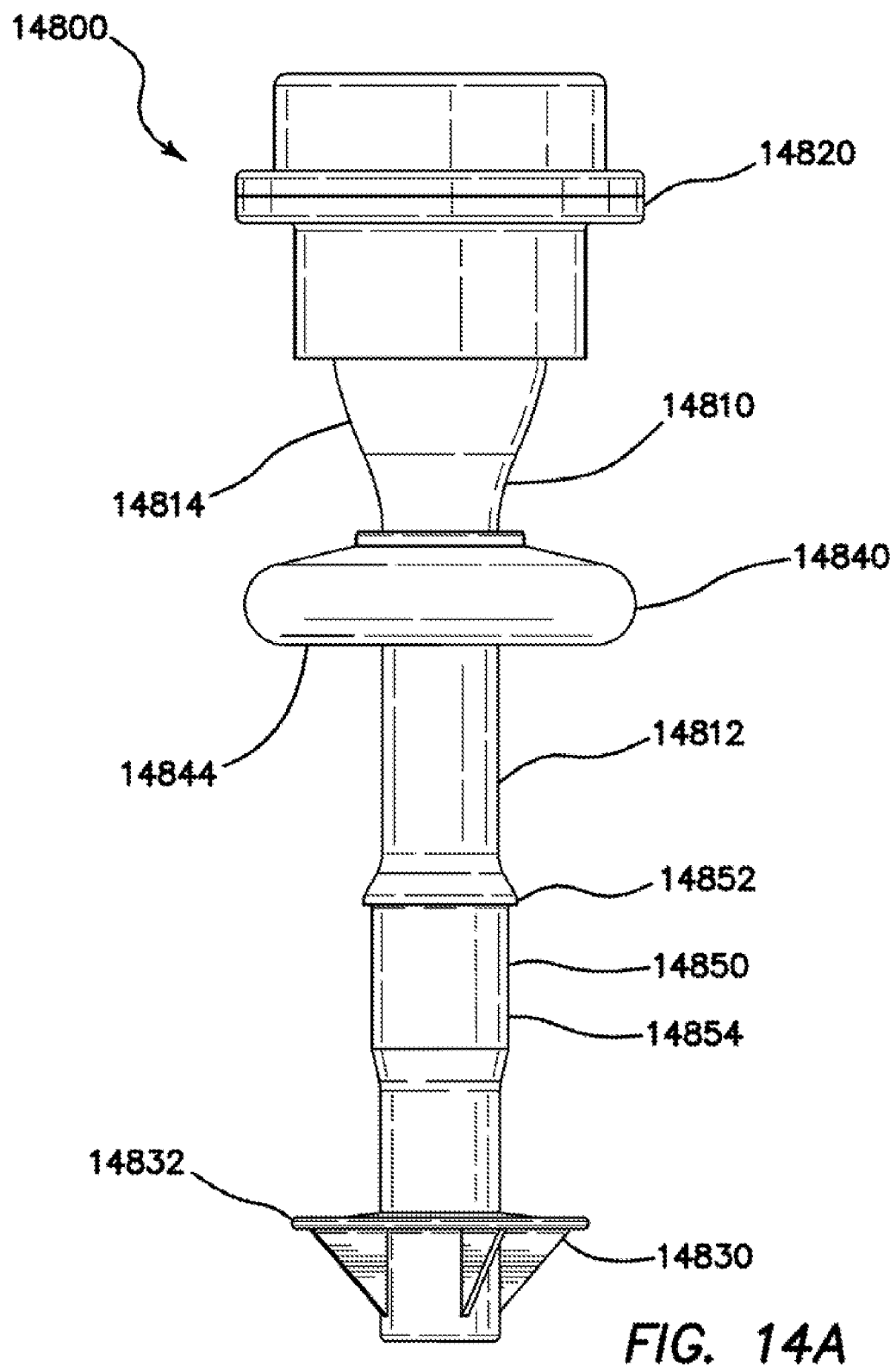
FIGS. 14A and 14B are side views of an embodiment of a trocar comprising a fixation cannula in an insertion configuration and a fixation configuration, respectively.

FIG. 14A is a side view of another embodiment of a trocar 14800 that is suitable as a component of a single-port surgical access system described above, for example, comprising a gel pad 10530 and retractor. Some embodiments of the access system comprise a plurality of trocars 14800. The trocar 14800 is generally similar to the trocar 13800 described above, and comprises a cannula 14810, a trocar seal assembly 14820, and a retainer 14830, which are generally similar to the corresponding features described above. The illustrated embodiment of the trocar 14800 further comprises a bolster 14840 and a locking component 14850. The illustrated embodiment of the cannula 14810 is also referred to as a "fixation cannula" as will become apparent from the discussion below.

In the illustrated embodiment, the bolster 14840 comprises a torus or doughnut. A cannula body 14812 extends through an opening in the bolster 14840. A diameter of the opening of the bolster 14840 is sufficiently larger than an outer diameter of the cannula body 14812 to permit free movement along the cannula body 14812. The illustrated embodiment of the bolster 14840 comprises a deformable material, for example, a polymer resin and/or elastomer, as will be described in greater detail below. Examples of suitable materials include rubber, natural rubber, synthetic rubber, polyisoprene, styrene-butadiene rubber, silicone rubber, ethylene-propylene copolymer, ethylene-propylene-diene monomer rubber, polybutadiene, polychloroprene, polyurethane, and the like. Some embodiments of the bolster 14840 comprise a lubricious layer or coating in an area or region that contacts the cannula 14810, which facilitates movement along the cannula 14810.

An outer diameter of some embodiments of the bolster 14840 is from about 0.8 to about 2 times, or from about 1 to about 1.5 times a diameter of a flange 14832 of the retainer 14830. A thickness of the bolster is from about 3 mm (0.12 inch) to about 10 mm (0.4 inch), or from about 4 mm (0.16 inch) to about 6 mm (0.24 inch). In some embodiments, a distal face 14844 of the bolster is concave, thereby providing additional clamping or fixation force on the gel pad 10530, as well as conforming to gel pads 10530 with different and/or non-uniform thicknesses. The particular dimensions of the bolster 14830 are selected based on the properties of the bolster material and the gel material, and the dimensions of the cannula body 14812, the locking component 14850, and the gel pad 10530.

The locking component 14850 is disposed on the cannula body 14812 proximal of the retainer 14830, and comprises a lip 14852 proximal of an enlarged section 14854. The lip 14852 extends radially from the cannula body 14812 with a diameter greater than the diameter of the opening of the bolster 14840. The elastomeric material of the bolster 14840 permits the bolster 14840 to be urged over and past the lip 14852. In the illustrated embodiment, the lip 14852 comprises a ratchet dimensioned to facilitate the bolster 14840 sliding distally and to resist the bolster 14840 from sliding proximally. Also, in the illustrated embodiment, the lip 14852 is a continuous structure encircling the cannula body 14812. In other embodiments, the lip 14852 comprises a plurality of structures disposed around the cannula body 14812.

The enlarged section 14854 is generally cylindrical with a diameter that is about the same as or slightly larger than the diameter of the opening in the bolster 14840, thereby frictionally engaging the bolster 14840 thereto. In the illustrated embodiment, the enlarged section 14854 is longer than a thickness of the bolster 14840. In the illustrated embodiment, the enlarged section 14854 does not extend to or contact the flange 14832 of the retainer 14830, thereby not reducing a surface area of a proximal face thereof, and thereby improving the removal resistance thereof. In other embodiments, the enlarged section 14854 extends to the retainer 14830. Other embodiments do not comprise an enlarged section.

A distance between a distal end of the lip 14852 and a proximal face of the flange 14832 is equal to or slightly less than a sum of a thickness of the bolster 14840 and the gel pad 10530. In some embodiments, the gel pad is from about 5 mm (about 0.4 inch) to about 30 mm (about 1.2 inch) thick, or from about 13 mm (about 0.5 inch) to about 25 mm (about 1 inch) thick.

Figure 14B:
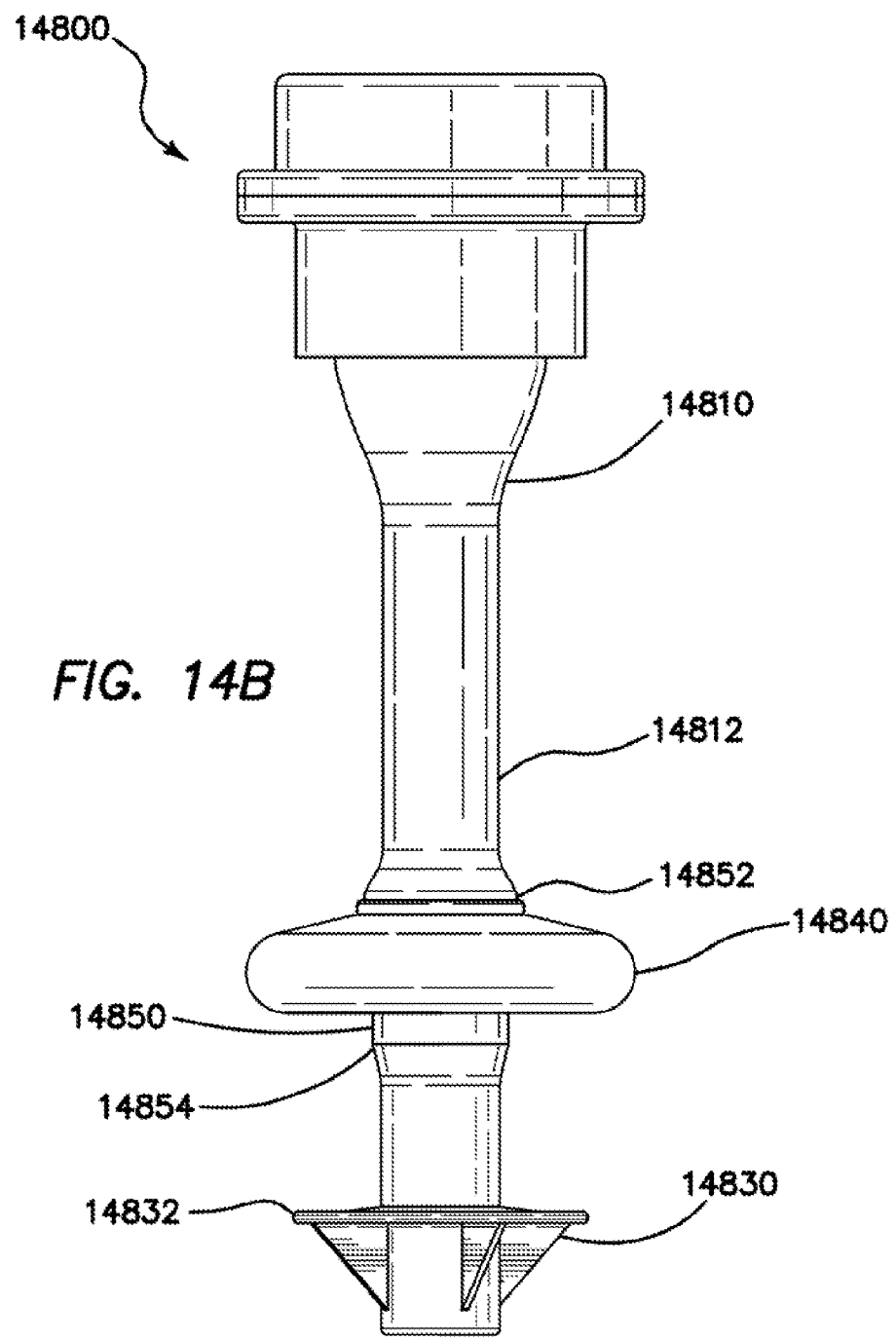

The trocar 14800 has at least two configurations: a first or insertion configuration illustrated in FIG. 14A, and a second or fixation configuration illustrated in FIG. 14B.

In an embodiment of a method for using the trocar 14800, the trocar 14800 is placed in the insertion configuration in which the bolster 14840 is first positioned on the cannula body 14812. The trocar 14800 is placed in the artificial body wall either before the artificial body wall is coupled to a patient's body and/or after coupling thereto.

In the embodiment illustrated in FIG. 14A, the bolster 14840 is positioned at the proximal end of the cannula body 14812, where the bolster 14840 frictionally engages a distal portion of a cannula bell 14814, which is an enlarged portion at the proximal end of the cannula 14810 to which the seal assembly 14820 couples.

The distal end of the trocar 14800 is positioned on, then the retainer 14830 inserted through an artificial body wall, for example, a gel pad 10530. In some embodiments, an obturator 13900 (FIG. 13) is first inserted through the seal assembly 14820 at the proximal end of the trocar with the tip 13910 extending from the distal end thereof before this step. In other embodiments, an opening is first made in the artificial body wall using another instrument. In other embodiments, the distal end of the trocar 14800 is forced through the artificial body wall, generating an opening in the process.

The trocar 14800 is then converted into the fixation configuration illustrated in FIG. 14B by sliding the bolster 14840 down the cannula body 14812, and over the lip 14852 onto the enlarged section 14852. In the illustrated configuration, the artificial body wall is captured and compressed between the flange 14830 of the retainer and the bolster 14840. The lip 14852 locks the bolster 14840 in place, preventing it from moving proximally, thereby fixing or locking the trocar 14800 to the artificial body wall.

In the fixation configuration, the trocar 14800 fixed relative to a local portion of the artificial body wall to which it is engaged. As discussed above, however, embodiments of artificial body walls exhibit high elongations. Accordingly, the trocar 14800 is translatable and/or pivotable relative to an original position and orientation by deforming the artificial body wall.

In embodiments using an obturator 13910, the obturator is withdrawn. The trocar 14800 serves as an access port for one or more instruments during a surgical procedure.

If desired, the trocar 14800 is removed from the artificial body wall, for example, by first disengaging the bolster 14840 from the locking component 14850, then pulling the retainer 14830 from the artificial body wall. In some embodiments, the trocar 14800 and artificial body wall are not disengaged and are disposed of as a unit. In some embodiments, the bolster 14840 is not disengagable from the locking component 14850.

Figure 15:
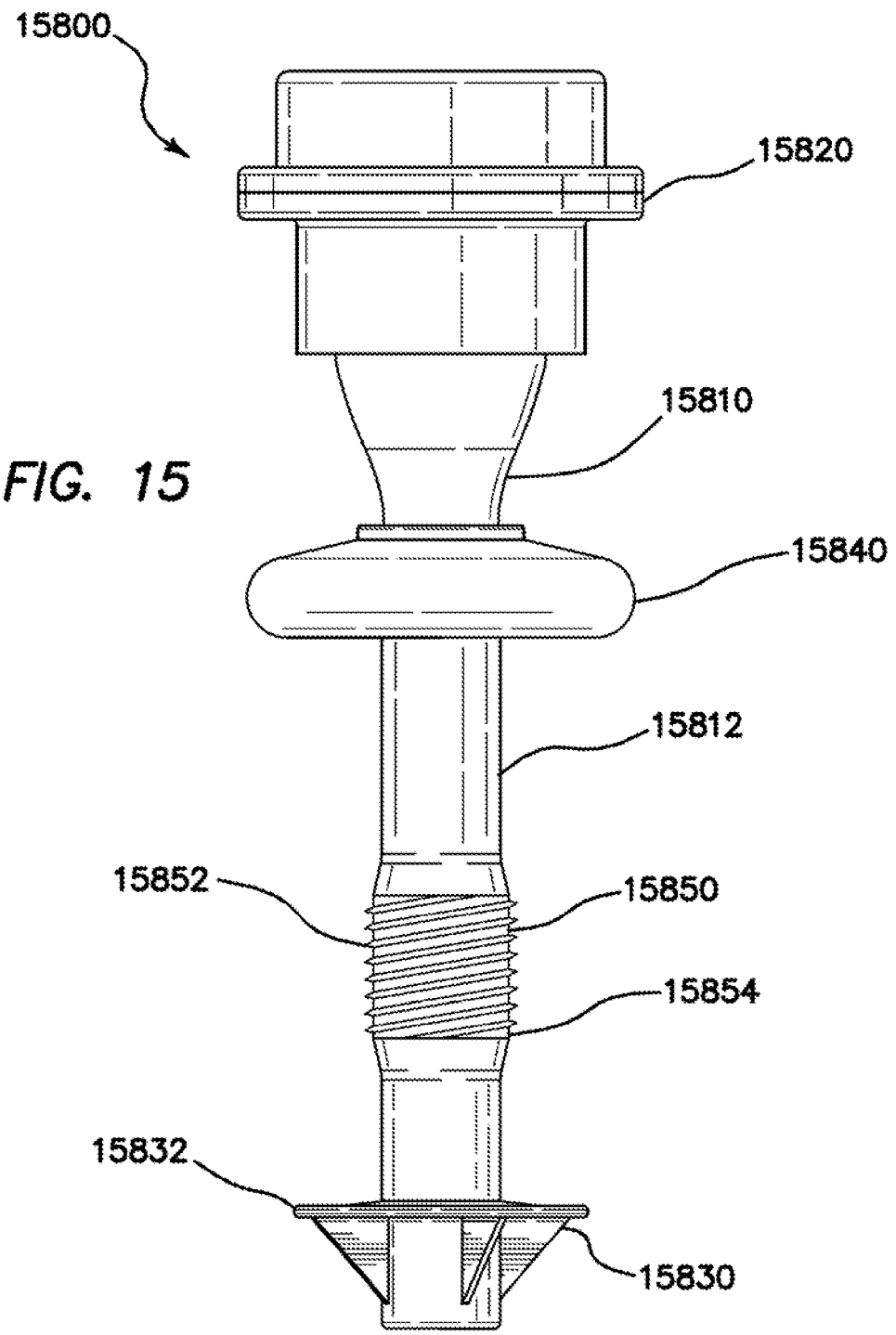
FIG. 15 is a side view of another embodiment of a trocar comprising a fixation cannula.

FIG. 15 is a side view of another embodiment of a retention trocar 15000, which is generally similar to the embodiment illustrated in FIGS. 14A and 14B and described above. The trocar 15000 comprises an elongate, tubular cannula 15810 comprising a proximal end, a distal end, and a cannula body 15812; a seal assembly 15820 coupled to the proximal end of the cannula 15810; a retainer 15830 disposed at the distal end of the cannula 15810; a bolster 14840 through which the cannula body 15812 extends; and a locking component 15850 disposed on the cannula body proximal of the retainer 15830.

In the illustrated embodiment, the locking component 15850 comprises an enlarged section 15854 on which are disposed screw threads 15852. The bolster 15840 comprises matching threads. Consequently, the bolster 15840 is threadably engagable to the locking component 15850. The threading also permits adjusting the relative positions of the bolster 15840 and a flange 15832 of the retainer in the fixation configuration of the trocar 15800, thereby permitting fixation to an artificial body wall with a non-uniform thickness and/or to artificial body walls of different thicknesses.

Figures 16A, 16B:
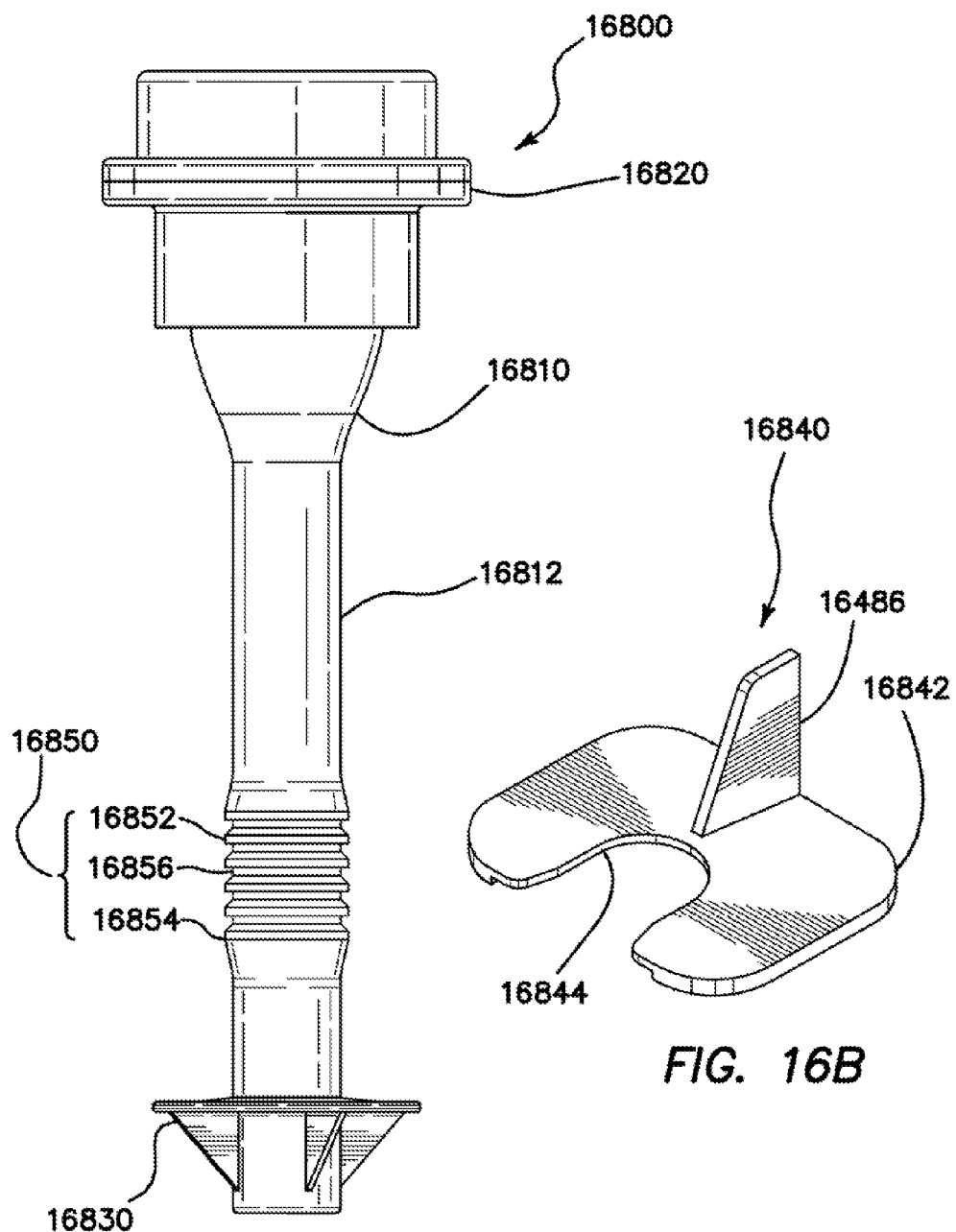
FIG. 16A is a side view of another embodiment of a trocar comprising a fixation cannula.
FIG. 16B is a perspective view of an embodiment of a bolster suitable for use with the trocar illustrated in FIG. 16A.

FIG. 16A is a side view of another embodiment of a trocar 16800. FIG. 16B is a perspective view of an embodiment of a bolster 16840 usable with the trocar 16800. The combination of the trocar 16800 and bolster 16840 are generally similar to the embodiments of trocars illustrated in FIGS. 14A, 14B, and 15. The trocar 16800 comprises an elongate, tubular fixation cannula 16810 comprising a proximal end, a distal end, and a cannula body 16812; a seal assembly 16820 coupled to the proximal end of the cannula 16810; a retainer 16830 disposed at the distal end of the cannula 16810; and a locking component 16850 disposed on the cannula body proximal of the retainer 16830.

In the illustrated embodiment, the locking component 16850 comprises an enlarged section 16854 comprising a plurality of annular rings 16852 extending radially from the cannula body 16812, which define a plurality of annular slots 16856. In the illustrated embodiment, a proximal edge of each ring 16856 is beveled; however, some embodiments do not comprise a beveled edge.

FIG. 16B illustrates an embodiment of a bolster 16840 in the form of a clip comprising a flattened body 16842 comprising a cut-out 16844 comprising a semicircular portion. The cut-out 16844 is dimensioned to engage the slots 16856. A thickness of the body 16842 at the cut-out 16844 is also dimensioned to engage the slots 16856. The bolster 16840 comprises a grip 16846 extending vertically from the body 16842, which provides a user grip for installing and/or adjusting the bolster 16840. In other embodiments, the cut-out 16844 has another shape, for example, polygonal, rectangular, a portion of a hexagon, and the like.

In use, the retainer 16830 of the trocar is inserted through an artificial body wall as discussed above, and fixed therein by engaging the bolster 16840 in a slot 16856 providing a desired fixation force. The degree of fixation is adjustable by selecting a different slot.

In some embodiments, the bolster cut-out 16844 engages a plurality of slots, thereby providing additional stability in the fixation configuration. Other embodiments comprise a bolster through with the cannula body 16812 extends, similar to the embodiments discussed above. In some of these embodiments, the locking component 16850 serves as a ratchet. The bolster comprises one or more pawls, which are optionally disengagable, thereby enhancing adjustability.

Figures 17A, 17B:
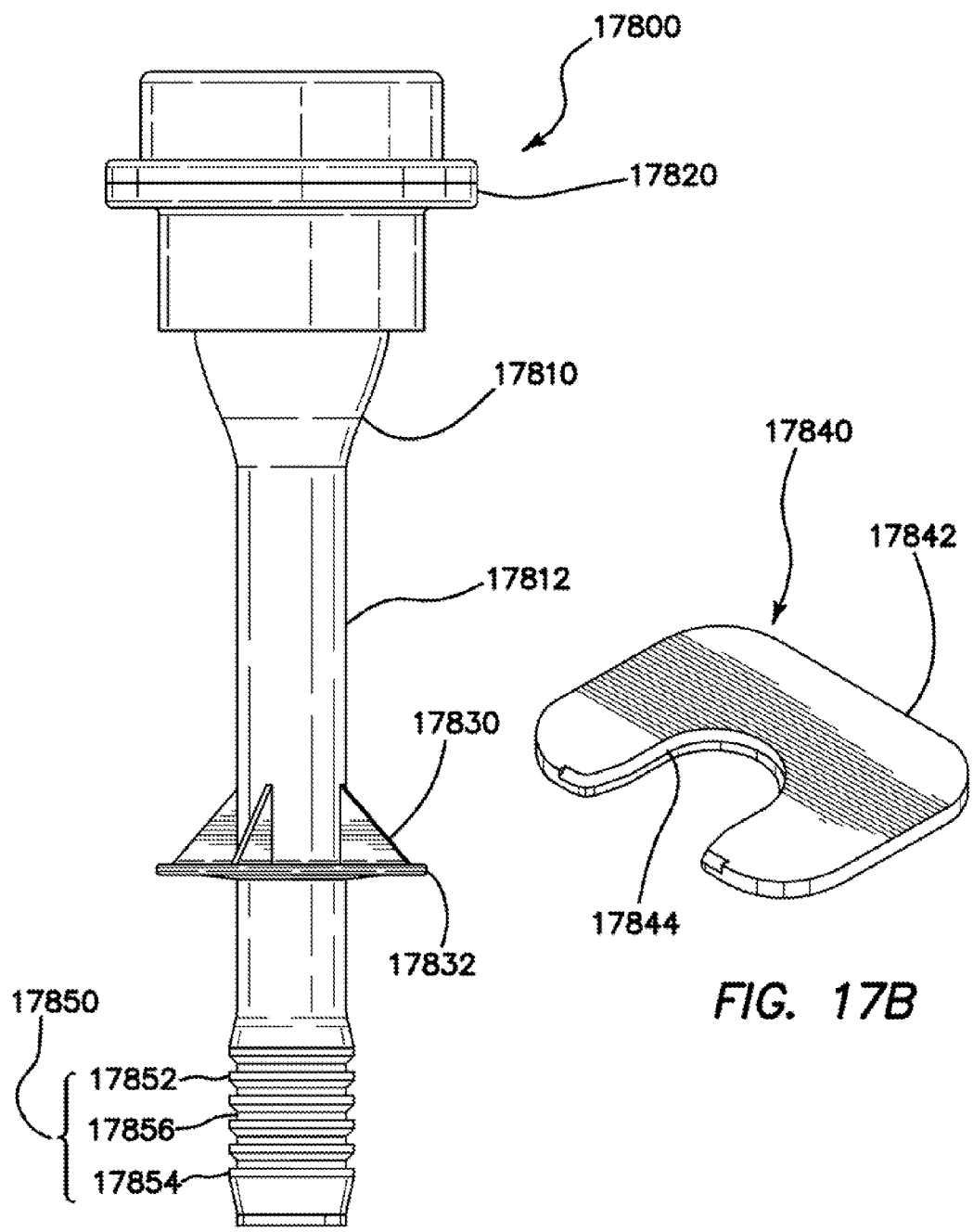
FIG. 17A is a side view of another embodiment of a trocar comprising a fixation cannula.
FIG. 17B is a perspective view of an embodiment of a bolster suitable for use with the trocar illustrated in FIG. 17A.

FIG. 17A illustrates a side view of an embodiment of a trocar 17800 comprising a fixation cannula and FIG. 17B is a perspective view of an embodiment of a bolster. The embodiments illustrated in FIGS. 17A and 17B are generally similar to the embodiments of trocars illustrated in FIGS. 14A-16B and described above.

The trocar 17800 comprises an elongate, tubular fixation cannula 17810 comprising a proximal end, a distal end, and a cannula body 17812; a seal assembly 17820 coupled to the proximal end of the cannula 17810; a retainer 17830 disposed on the cannula body 17812; and a locking component 17850 disposed at the distal end of the cannula 17810. The illustrated embodiment of the trocar 17800 is similar to the embodiment illustrated in FIG. 16A with the positions of the retainer 17830 and the locking component 17850 reversed. In the illustrated embodiment, a flange 17832 of the retainer faces distally.

The locking component 17850 comprises an enlarged section 17854 comprising a plurality of annular rings 17852 extending radially from the cannula body 17812, which define a plurality of annular slots 17856.

FIG. 17B illustrates an embodiment of a bolster 17840 in the form of a clip comprising a flattened body 17842 comprising a cut-out 17844 comprising a semicircular portion. The cut-out 17844 is dimensioned to engage slots 17856 in the locking component. A thickness of the body 17842 at the cut-out 17844 is also dimensioned to engage the slots 17856. The illustrated embodiment of the bolster does not comprise a grip; however, other embodiments comprise a grip.

In some embodiments for using the embodiment of the trocar 17800, the cannula 17810 is fixed to an artificial body wall before the artificial body wall is coupled to a patient's body. For example, in some embodiments, one or more trocars 17800 are fixed on a gel pad 10530 (FIG. 10A) of a gel cap 10500 before the gel cap 10500 is coupled to a retractor 7100 (FIG. 7).

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A surgical access system comprising a trocar comprising: a fixation cannula comprising a tubular cannula body comprising a proximal end, a distal end, a longitudinal axis extending from the proximal end to the distal end; and a cannula wall defining a cannula lumen; a seal assembly coupled to the proximal end of the cannula body; a retainer extending from the cannula body; a locking component disposed on the cannula body and spaced from the retainer; and a bolster engagable to the locking component, wherein the trocar has an insertion configuration in which the bolster is not engaged to the locking component, the trocar has a fixation configuration in which the bolster is engaged to the locking component, an artificial body wall, wherein the artificial body wall comprises a gel pad, wherein the gel pad is coupled to a cap ring, thereby defining a gel cap; an adjustable wound retractor, wherein the adjustable wound retractor is couplable to the gel cap, and in the fixation configuration, the retainer and the bolster are dimensioned and configured to capture the artificial body wall therebetween, thereby fixing the cannula to the artificial body wall.

2. The surgical access system of claim 1, wherein the trocar is a 5-mm trocar.

3. The surgical access system of claim 1, wherein the cannula comprises at least one of polycarbonate and polyester.

4. The surgical access system of claim 1, wherein the seal assembly comprises a septum valve and a duckbill valve.

5. The surgical access system of claim 1, wherein the retainer is disposed at the distal end of the cannula body and the locking component is proximal of the retainer.

6. The surgical access system of claim 1, wherein the retainer comprises a radially extending flange.

7. The surgical access system of claim 6, wherein a diameter of the retainer flange is from about 1.5 to about 2.5 times wider than an outer diameter of the cannula body.

8. The surgical access system of claim 1, wherein a distal end of the retainer tapers.

9. The surgical access system of claim 1, wherein the locking component comprises an enlarged section.

10. The surgical access system of claim 1, wherein the locking component comprises a circumferential lip.

11. The surgical access system of claim 1, wherein the bolster comprises an elastomeric material.

12. The surgical access system of claim 1, wherein the bolster comprises a torus comprising an opening through with the cannula body extends.

13. The surgical access system of claim 1, wherein a diameter of the bolster is from about 0.8 to about 2 times a diameter of a flange.

14. The surgical access system of claim 1, wherein in the fixation configuration, the locking component resists disengagement of the bolster.

15. The surgical access system of claim 1, wherein in the fixation configuration, a distance between the retainer and the bolster is adjustable.

16. The surgical access system of claim 1, further comprising an obturator.

17. A surgical access system comprising:
an adjustable wound retractor comprising:
an proximal ring, distal ring, and a flexible, tubular retraction sheath extending between the proximal ring and the distal ring,
wherein the proximal ring is rotatable around an annular axis thereof, thereby adjusting a length of the retraction sheath between the proximal ring and the distal ring;
a gel cap comprising a cap ring and a gel pad coupled with the cap ring, wherein the cap ring is engagable with the proximal ring; and
a trocar comprising:
a fixation cannula comprising a tubular cannula body comprising a proximal end, a distal end, a longitudinal axis extending from the proximal end to the distal end; and a cannula wall defining a cannula lumen;
a seal assembly coupled to the proximal end of the cannula body;
a retainer extending from the cannula body;
a locking component disposed on the cannula body and spaced from the retainer; and
a bolster engagable to the locking component,
wherein
the trocar has an insertion configuration in which the bolster is not engaged to the locking component,
the trocar has a fixation configuration in which the bolster is engaged to the locking component, and
in the fixation configuration, the retainer and the bolster are dimensioned and configured to capture the gel pad therebetween, thereby fixing the cannula to the gel pad.

18. The surgical access system of claim 17 wherein the locking component has a lip with a distal end and the retainer has a proximal face with a distance between the distal end of the lip to the proximal face of the retainer being equal to a sum of a thickness of the bolster and the gel pad.

19. The surgical access system of claim 18 wherein the lip locks the bolster in place preventing it from moving proximally and locks the trocar to the gel pad.

20. The surgical access system of claim 18 wherein the locking component comprises an enlarged section having a diameter greater than an outer diameter of the cannula and smaller than a diameter of the retainer and a diameter of the distal end of the lip.

21. The surgical access system of claim 20 wherein the enlarged section is longer than the thickness of the bolster and does not extend to the retainer.

22. The surgical access system of claim 20 wherein the enlarged section has a smooth outer surface.

23. The surgical access system of claim 17 wherein the bolster is not disengagable from the locking component.

* * * * *